(12) United States Patent
Mori et al.

(10) Patent No.: US 8,557,068 B2
(45) Date of Patent: Oct. 15, 2013

(54) METHOD FOR MANUFACTURING AN ABSORBENT BODY OF A BODY FLUID ABSORBING ARTICLE

(75) Inventors: Yosuke Mori, Iyomishima (JP); Kazunori Ito, Niihama (JP)

(73) Assignee: Daio Paper Corporation, Iyomishima-shi, Ehime (JP)

( * ) Notice: Subject to any disclaimer, the term of this patent is extended or adjusted under 35 U.S.C. 154(b) by 1 day.

(21) Appl. No.: 12/803,996

(22) Filed: Jul. 12, 2010

(65) Prior Publication Data

US 2010/0326580 A1     Dec. 30, 2010

Related U.S. Application Data

(62) Division of application No. 10/433,725, filed as application No. PCT/JP01/10740 on Jul. 12, 2001, now abandoned.

(30) Foreign Application Priority Data

Dec. 8, 2000 (JP) .................................. 2000-374191
Jan. 15, 2001 (JP) .................................. 2001-006360

(51) Int. Cl.
*B27N 3/04* (2006.01)

(52) U.S. Cl.
USPC .......................................... 156/62.8; 156/253

(58) Field of Classification Search
None
See application file for complete search history.

(56) References Cited

U.S. PATENT DOCUMENTS

| | | | |
|---|---|---|---|
| 3,692,622 A | 9/1972 | Dunning | |
| 4,102,340 A | 7/1978 | Mesek et al. | |
| 4,141,772 A * | 2/1979 | Buell | 156/227 |
| 4,354,901 A | 10/1982 | Kopolow | |
| 4,388,056 A * | 6/1983 | Lee et al. | 425/83.1 |
| 4,559,050 A | 12/1985 | Iskra | |
| 4,596,567 A | 6/1986 | Iskra | |
| 4,610,678 A | 9/1986 | Weisman et al. | |
| 4,654,039 A | 3/1987 | Brandt et al. | |

(Continued)

FOREIGN PATENT DOCUMENTS

| | | |
|---|---|---|
| EP | 0122042 A1 | 10/1984 |
| EP | 304319 A2 | 2/1989 |

(Continued)

OTHER PUBLICATIONS http://www.answers.com/topic/mesh-scale, no date.*

(Continued)

*Primary Examiner* — Barbara J Musser
(74) *Attorney, Agent, or Firm* — Holtz Holtz Goodman & Chick PC

(57) ABSTRACT

A method for manufacturing an absorbent body of a body fluid absorbing article. The absorbent body includes an air laid absorbent fiber having a dispersed and thin layer of a mixed absorbent fiber and super absorbent polymer. The method involves using multiple stages having multiple dispersing chutes and pressing rolls spaced out in a transfer direction to accumulate and form the absorbent fiber and the super absorbent polymer while disentangling and mixing the absorbent fiber and the super absorbent polymer in accordance with an air laying method in which the absorbent fiber and the super absorbent polymer are conveyed in an air flow and injected by the dispersing chutes to provide the dispersed layer of the mixed absorbent fiber and super absorbent polymer, and thin the air laid absorbent fiber, by pressurization, by using the pressing rolls to thin the dispersed layer.

3 Claims, 59 Drawing Sheets

(56) References Cited

U.S. PATENT DOCUMENTS

| | | | |
|---|---|---|---|
| 4,673,402 A | 6/1987 | Weisman et al. | |
| 4,761,258 A * | 8/1988 | Enloe | 264/518 |
| 4,859,388 A * | 8/1989 | Peterson et al. | 264/121 |
| 4,908,175 A | 3/1990 | Angstadt | |
| 4,988,345 A | 1/1991 | Reising | |
| 5,149,335 A | 9/1992 | Kellenberger et al. | |
| 5,171,237 A | 12/1992 | Poccia et al. | |
| 5,180,622 A | 1/1993 | Berg et al. | |
| 5,188,624 A * | 2/1993 | Young et al. | 604/378 |
| 5,242,435 A | 9/1993 | Murji et al. | |
| 5,246,429 A | 9/1993 | Poccia et al. | |
| 5,350,370 A | 9/1994 | Jackson et al. | |
| 5,368,918 A | 11/1994 | Harada et al. | |
| 5,387,385 A | 2/1995 | Murji et al. | |
| 5,397,316 A | 3/1995 | LaVon et al. | |
| 5,415,649 A | 5/1995 | Watanabe et al. | |
| 5,419,956 A | 5/1995 | Roe | |
| 5,422,169 A | 6/1995 | Roe | |
| 5,462,972 A | 10/1995 | Smith et al. | |
| 5,490,846 A | 2/1996 | Ellis et al. | |
| 5,516,569 A | 5/1996 | Veith et al. | |
| 5,562,646 A | 10/1996 | Goldman et al. | |
| 5,593,400 A | 1/1997 | O'Leary | |
| 5,599,335 A | 2/1997 | Goldman et al. | |
| 5,601,542 A | 2/1997 | Melius et al. | |
| H1639 H | 3/1997 | Crainic | |
| 5,609,727 A * | 3/1997 | Hansen et al. | 162/184 |
| 5,611,790 A | 3/1997 | Osborn, III et al. | |
| 5,649,918 A | 7/1997 | Schleinz | |
| 5,669,894 A | 9/1997 | Goldman et al. | |
| 5,681,300 A | 10/1997 | Ahr et al. | |
| 5,702,382 A | 12/1997 | Osborn, III et al. | |
| 5,800,419 A | 9/1998 | Soga et al. | |
| 5,821,179 A * | 10/1998 | Masaki et al. | 442/375 |
| 5,836,931 A | 11/1998 | Toyoda et al. | |
| 5,846,365 A | 12/1998 | Kline et al. | |
| 5,919,411 A | 7/1999 | Rezai et al. | |
| 5,925,026 A | 7/1999 | Arteman et al. | |
| 6,102,900 A | 8/2000 | Roessler et al. | |
| 6,140,551 A | 10/2000 | Niemeyer et al. | |
| 6,203,654 B1 | 3/2001 | McFall et al. | |
| 6,287,286 B1 * | 9/2001 | Akin et al. | 604/385.01 |
| 6,364,863 B1 | 4/2002 | Yamamoto et al. | |
| 6,479,061 B2 | 11/2002 | Fontenot et al. | |
| 6,485,667 B1 * | 11/2002 | Tan | 264/510 |
| 6,710,222 B2 | 3/2004 | Shimada et al. | |
| 7,005,558 B1 | 2/2006 | Johansson et al. | |
| 2002/0173764 A1 | 11/2002 | Takino et al. | |
| 2003/0129914 A1 | 7/2003 | Ranganathan et al. | |
| 2003/0139726 A1 | 7/2003 | Gibbs | |
| 2004/0030317 A1 | 2/2004 | Torigoshi | |
| 2004/0230184 A1 | 11/2004 | Babusik et al. | |
| 2006/0173433 A1 | 8/2006 | Laumer et al. | |

FOREIGN PATENT DOCUMENTS

| | | |
|---|---|---|
| EP | 0 339 461 A1 | 11/1989 |
| EP | 0 359 501 A2 | 3/1990 |
| EP | 0 293 208 B1 | 7/1991 |
| EP | 0 443 627 A2 | 8/1991 |
| EP | 0 478 150 A2 | 4/1992 |
| EP | 0 494 112 A2 | 7/1992 |
| EP | 0 672 774 A2 | 9/1995 |
| EP | 700 672 A1 | 3/1996 |
| EP | 0 813 848 A1 | 12/1997 |
| EP | 591 168 B1 | 8/1999 |
| EP | 0 703 764 B1 | 9/1999 |
| EP | 0700627 B1 | 3/2000 |
| EP | 1219274 A1 | 7/2002 |
| JP | 63-309606 A | 12/1988 |
| JP | 9-501590 A | 2/1997 |
| JP | 9-191908 A | 7/1997 |
| JP | 9-313536 A | 12/1997 |
| JP | 10-57120 A | 3/1998 |
| JP | 10-76589 A | 3/1998 |
| JP | 10-265582 A1 | 10/1998 |
| JP | 11-28355 A | 2/1999 |
| JP | 11-107007 A | 4/1999 |
| JP | 11-318982 A | 11/1999 |
| JP | 2000-107 A | 1/2000 |
| JP | 2000-15093 A | 1/2000 |
| JP | 2000-503243 A | 3/2000 |
| JP | 2000-201975 A | 7/2000 |
| JP | 2000-262559 A | 9/2000 |
| JP | 2002336303 | 5/2001 |
| WO | WO 91/15177 A1 | 10/1991 |
| WO | WO 92/11831 | 7/1992 |
| WO | WO 93/01786 A1 | 2/1993 |
| WO | WO 95/00091 A1 | 1/1995 |
| WO | WO 95/05140 A1 | 2/1995 |
| WO | WO 98/51250 A1 | 11/1998 |
| WO | WO 99/17695 A1 | 4/1999 |
| WO | WO 99/25281 A1 | 5/1999 |
| WO | WO 99/42067 A1 | 8/1999 |
| WO | WO 99/42068 A1 | 8/1999 |

OTHER PUBLICATIONS

STIC Search Report—p. 2; Knaebel, A., Determination of the elastic modulus of superabsorbent gel beads, 1997, Universite Louis Pateur, abstract.

STIC Search Report—p. 3; Nisato, G., Swelling Equilibrium Properties of Partially Charged Gels: Effect of Salt on the Shear Modulus, (1996), Strasbourg, Universite Louis Pasteur; Polymer Gels and Netwroks; abstract.

STIC Search Report—p. 5: Aridall Superabsorbents Available in the UK, Anon., (1987), Nonwovens Rep. Int. No. 189, Jan. 1987, pp. 9-10, abstract.

STIC Search Report—p. 7: Rebre, S.R.; Collette, C., Superabsorbent Polymers With a New Structure and Their Performance in Hygienic Applications, (1993), Conference Publication, Nonwoven Ab, Hygiene Products, Geneva, Switzerland, abstract.

STIC Search Report—p. 8: Bucholz, Fredric L., Keeping Dry With Superabsorbent Polymers (1994), Chemtech v 24 n 9, Sep. 1994 pp. 38-43, Coden: CHTEDD ISSN: 0009-2703, abstract.

STIC Search Report—p. 11: Permeable Superabsorbents: Function and Importance for the Application in Diapers, Anon, (1999), The Absorber v 6 n 9 pp. 3-4, abstract.

English-language translation of the Notification of Reason for Refusal dated Nov. 7, 2008 for Japanese patent application No. 2001-006360.

Notice of opposition to counterpart European Patent No. 1350497 (Application No. 01999338.5), dated Feb. 17, 2012 (and English translation thereof).

Notice of opposition to counterpart European Patent No. 1350497 (Application No. 01999338.5), dated Feb. 14, 2012 (in English).

Notice of opposition to counterpart European Patent No. 1350497 (Application No. 01999338.5), dated Feb. 13, 2012.

Entscheidung zu (Revocation of European Patent) EP 1 618 240 (in English).

American Standard ASTM Designation D5729-97—Standard Test Method for Thickness of Nonwoven Fabrics (in English).

Entscheidung (Decision of the Technical Board of Appeal) T0252/02 (in English).

EDANA 30.5-99 (Thickness—Recommended Test Method: Nonwovens Thickness) (in English).

EDANA 30.4-89 (Thickness—Recommended Test Method: Nonwovens Thickness) (in English).

Declaration of Karl Karlsson in opposition against European Patent No. 1350497 (in English).

ASTM D 5736-95 (2001), "Standard Test Method of Highloft Nonwoven Fabrics".

Summons to attend oral proceedings mailed Jun. 3, 2013 in European application 01999338.5.

* cited by examiner

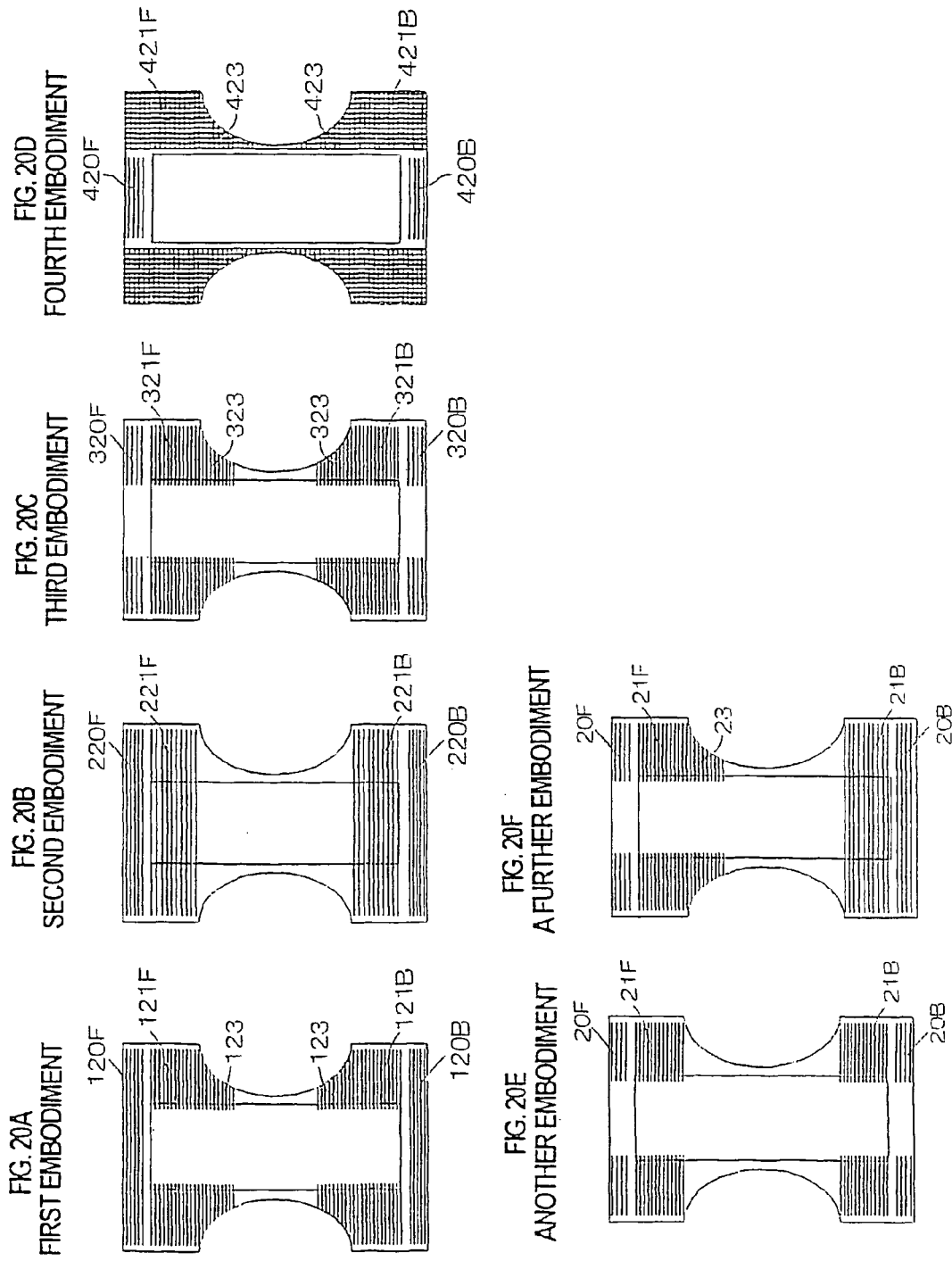

FIG. 21A  FRONT
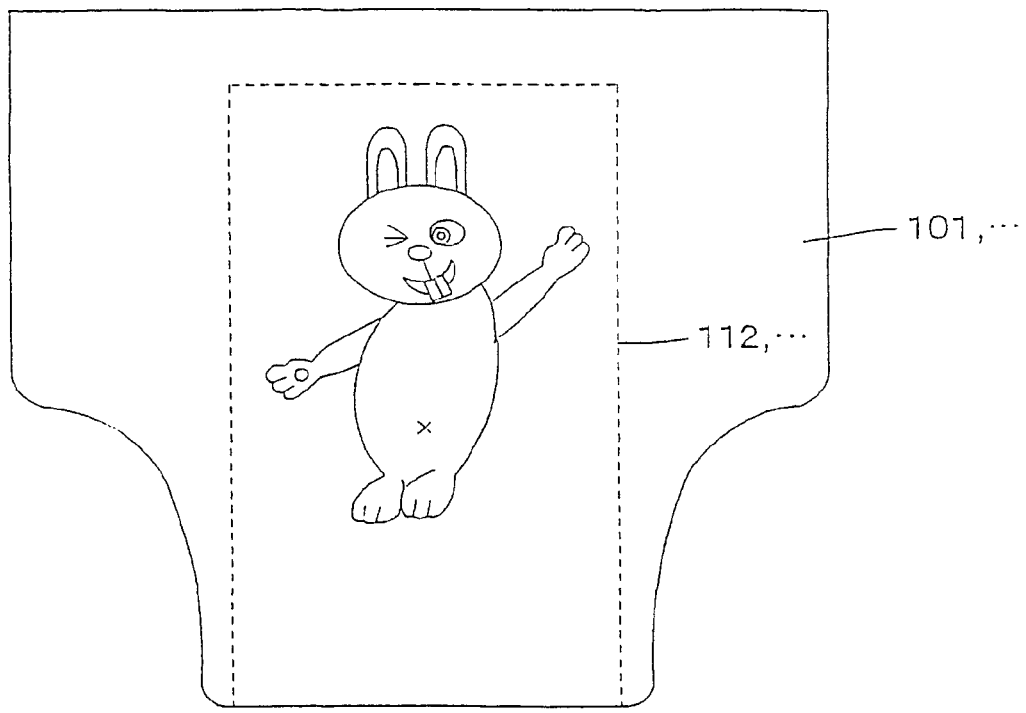
FIG. 21B  BACK
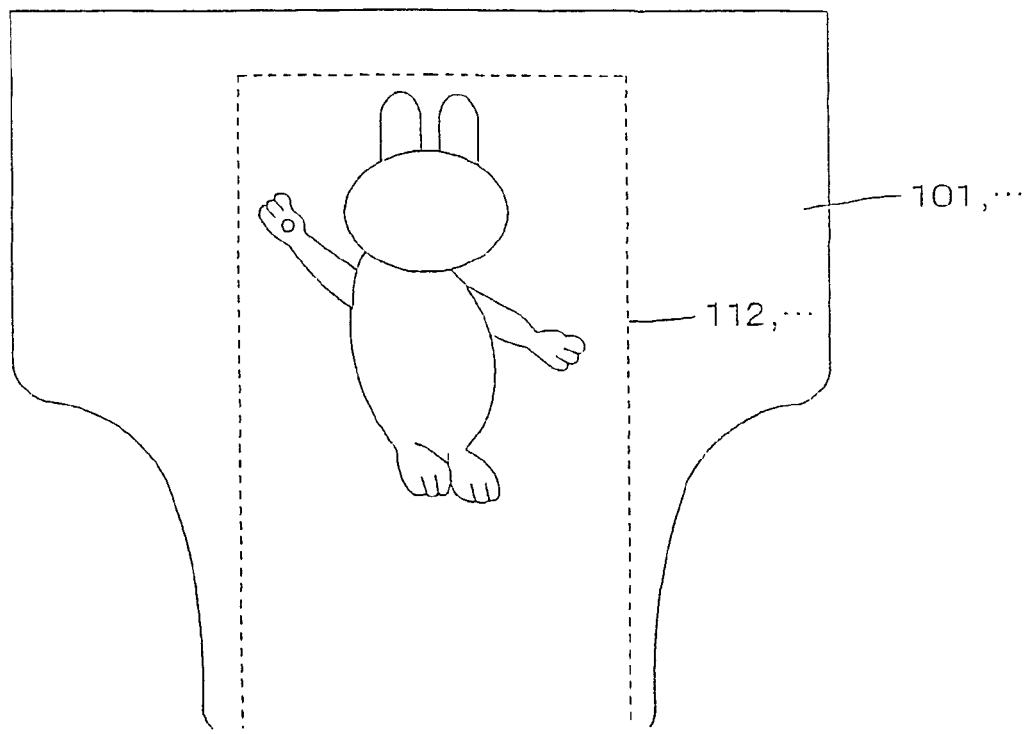

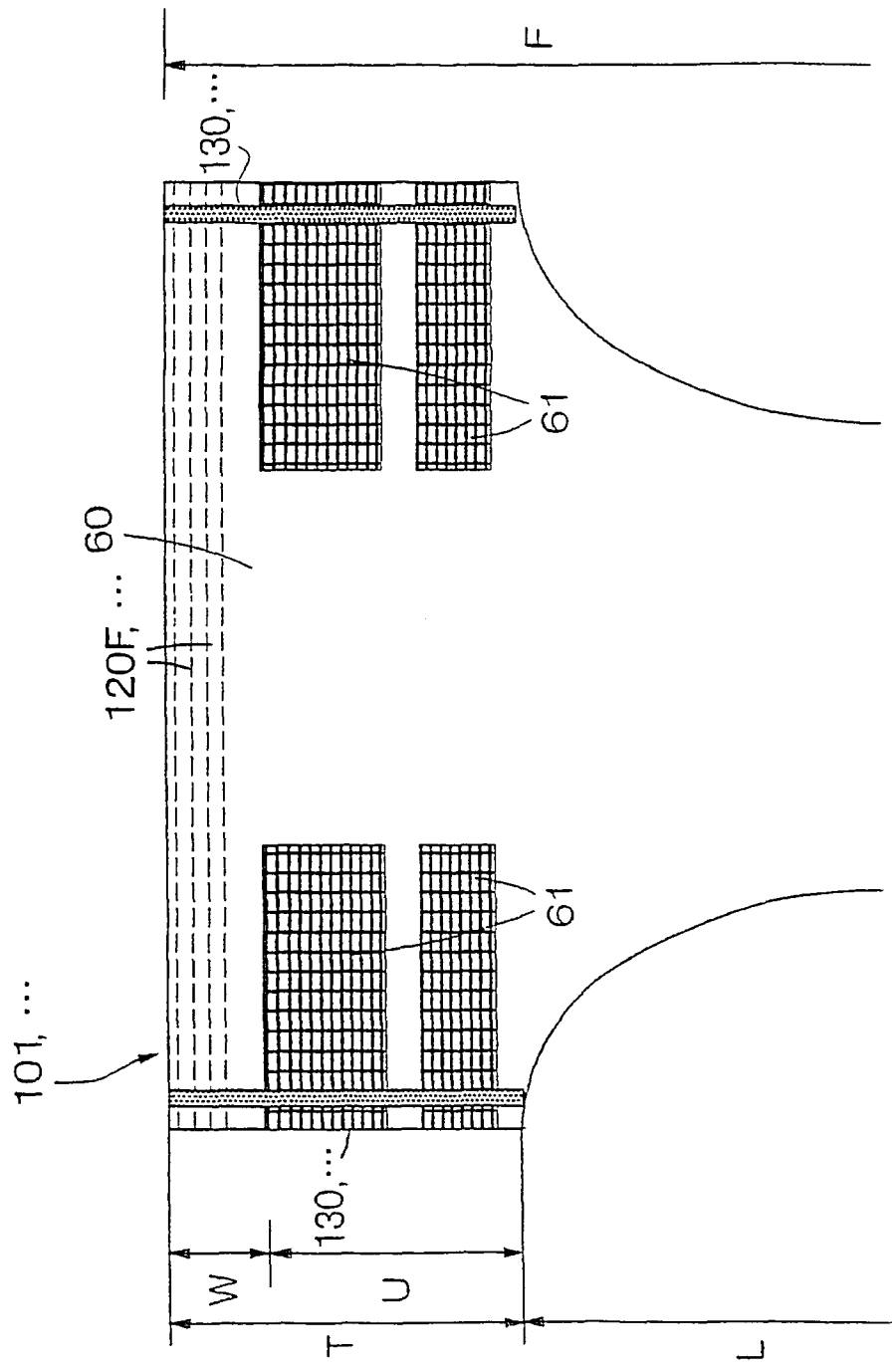

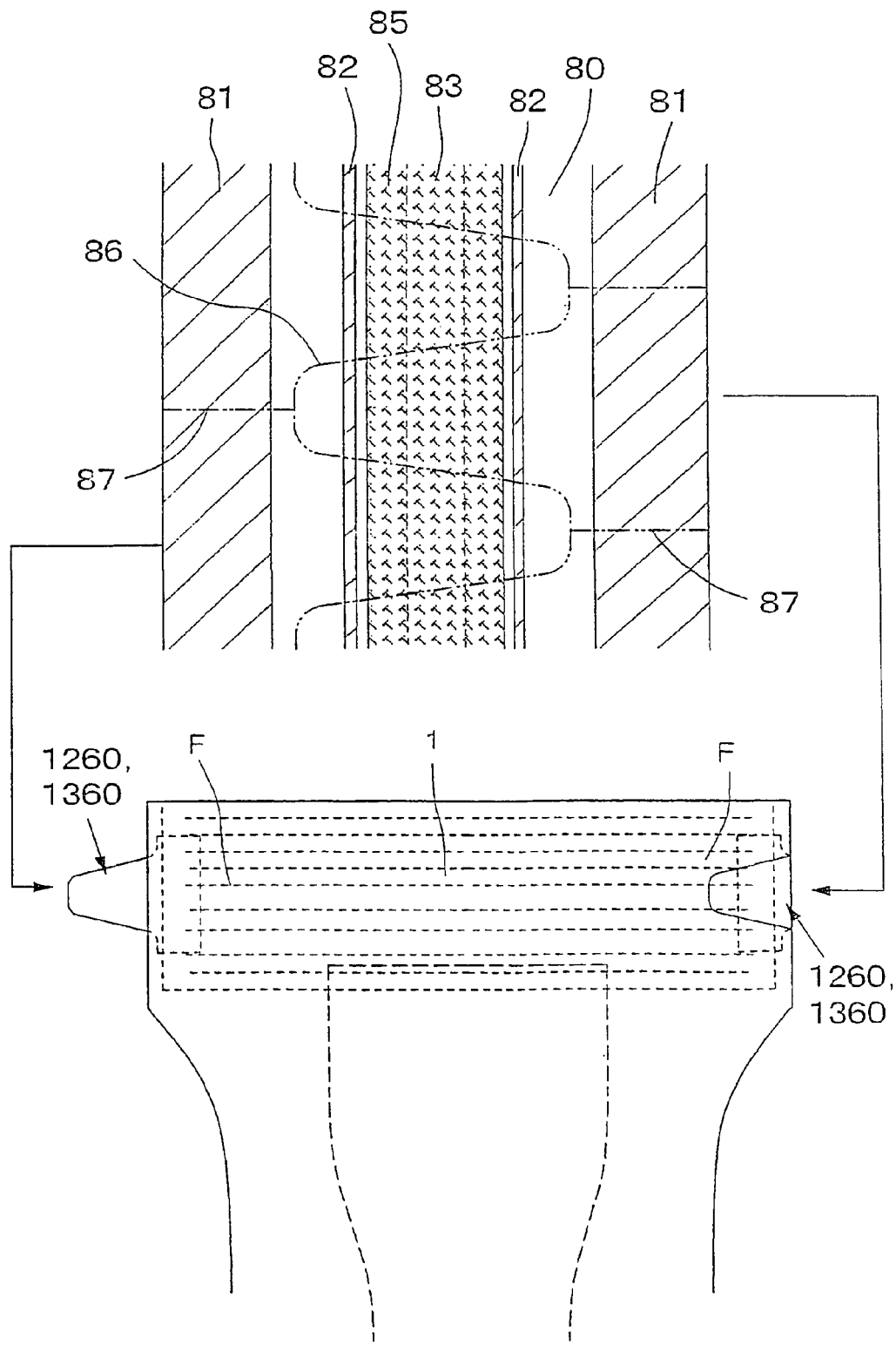

FIG. 59
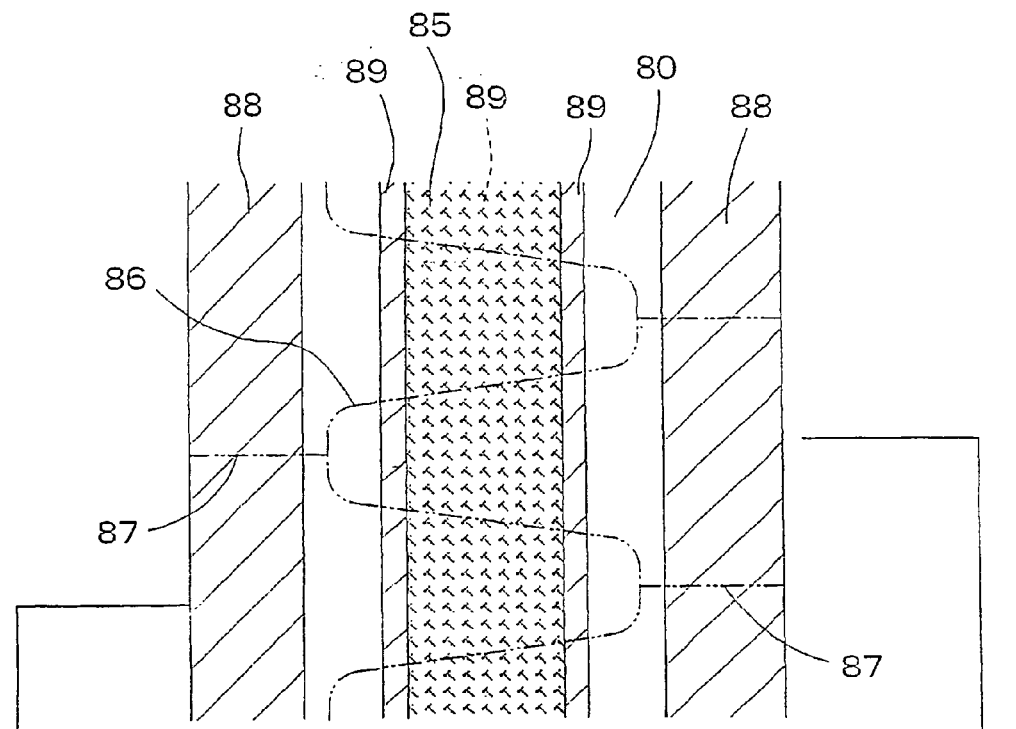
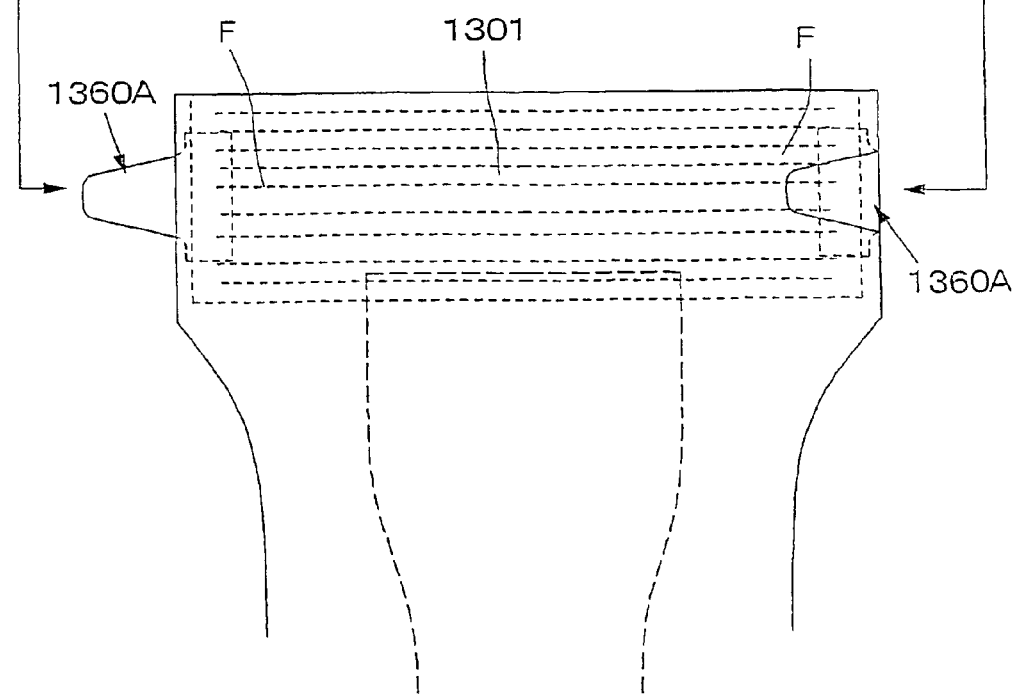

METHOD FOR MANUFACTURING AN ABSORBENT BODY OF A BODY FLUID ABSORBING ARTICLE

CROSS-REFERENCE TO RELATED APPLICATIONS

This application is a Divisional application of application Ser. No. 10/433,725, filed Jun. 3, 2003 now abandoned, which is a United States national phase application of International application PCT/JP01/10740 filed Jul. 12, 2001. The entire contents of each of application Ser. No. 10/433,725 and International application PCT/JP01/10740 are hereby incorporated by reference herein.

The present invention relates to an absorbent body which comprises a super absorbent polymer and absorbent fibers and has been thinned by pressing. More particularly, the present invention relates to an absorbent body which comprises a sufficient absorbing performance and flexibility, fits the motions of a human body and is excellent in wearability while a further thinning is promoted, to a method for manufacturing the absorbent body, to absorbent articles, such as disposable diapers which are called paper diapers, sanitary napkins, incontinence pads, medical pads and the like, which comprise the absorbent body, and to a disposable diaper having a mechanical fastening tape.

BACKGROUND ART

Various improvements have been steadily provided and accumulated for an absorbent body using a high absorbent polymer since body fluid absorbent articles such as disposable diapers, sanitary napkins and incontinence pads were marketed.

A super absorbent polymer (also called SAP or a highly absorbent resin) absorbs water and swells up to be a gel if the polymer contacts with water, has characteristics such that syneresis does not occur although some pressure is applied to the gel once water is absorbed therein and the like, and exerts a phenomenal water absorbing performance which reaches several ten times to several thousand times as much as the volume of the gel itself and the like, as it has been publicly known.

Although the simple substance of a super absorbent polymer exerts the absorbing performance as described above, the polymer can not exert the absorbing performance unless the polymer is placed in a wet state to some extent and since the water absorption rate is low, in an absorbent body, the polymer is mixed, for example, in the form of granular powder, crushed powder or pellets in absorbent fibers such as crushed pulps, rayon and the like.

Since in recent years, this kind of absorbent articles have problems such that it is inconvenient to carry them due to their volumes, storability is bad, a fitting property to a human body is bad, and the like, and a higher efficiency of distribution and resources-saving are required, thinning and densification have been promoted by performing press working on articles.

However, since for an absorbent body thinned by pressurization, the volume density of the absorbent body (crushed pulp and the like) extremely increases, the absorbing performance (absorption amount, absorption rate, transparency of solution) may deteriorate.

Therefore, although a number of basis weights are normally arranged so as not to allow the absorbing performance to drop while performing thinning and densification on an absorbent body, an extreme thinning cannot be promoted in this case. If the density of the high absorbent polymer becomes excessively high by thinning, there occurs so-called "gel blocking" that voids between swollen absorbent polymer particles become extremely small, thus a desired absorbing performance cannot be expressed. As a result, observed is a phenomenon that bonding between absorbent polymer particles inhibits the permeation of urine and the urine whose permeation is inhibited backflows and is discharged.

On the other hand, since an absorbent body thinned by pressurization is hardened by an increase in the volume density, if this absorbent body is applied to an absorbent article which is used in contact with a human body, there occurs a problem such that a user does not feel comfortable about the existence of a hard material, that wrinkles are largely formed in it, and the like, and thereby a leakage is likely to take place.

Therefore, the major object of the present invention is to provide an absorbent body capable of exerting an absorbing performance equivalent to an absorbent body in earlier technology, which is not thinned, while thinning is promoted and a method for manufacturing the same and an absorbent article.

Another object of the present invention is to provide an absorbent article capable of exerting an absorbing performance equivalent an absorbent article in earlier technology, which is not thinned, while thinning is promoted, and an absorbent article provided with a sufficient flexibility.

In addition, as shown FIG. 60, marketed is a disposable diaper where fastening tapes 3 and 3 are attached to both flaps F and F on the back side B respectively and when wearing the disposable diaper, the diaper is fastened in place at a predetermined region on the external surface of the belly side A. These fastening tapes 3 and 3 can be used when a disposable diaper is fastened in place with a carrion side rounded inwardly to dispose the disposable diaper after use.

The first prior example of this fastening tape 3 is an adhesive tape type. As shown in FIG. 61, there is one such that an adhesive portion 4 is formed on the entire inner surface of the extended portion from the side edge to the outside of a flap F, and fastening is performed directly on the external side of the belly side A or on an adhered tape 2 which is called a so-called front target tape fixed at the external side of the belly side A with the adhesion of the adhesive portion 4. A peeling tape 6 to redouble and temporarily hold the extended portion of the fastening tape 3 as a chain double-dashed line arrow shown in the figure is provided on the inner surface of the flap F. A tab tape 5 having a color which can distinguish the surroundings at the top portion of the adhesive portion 4 in the illustration example.

In the first prior example, if affixing is repeatedly performed on an adhered tape 2, the deterioration of an adhesion is observed. In addition, if the adhesive portion 4 is allowed by mistake to contact with a region other than the adhered tape 2, namely, a non-woven fabric surface, the adhesion deteriorates as the fibers of the non-woven fabric are attached to the adhesive portion, and it can be no longer used for fastening thereafter.

On the other hand, in a disposable diaper used recently, marketed is a disposable diaper where fastening is performed by a mechanical engagement with a surface fastener tape comprising a hook portion and a hook receptacle portion in place of an adhesive type-fastening tape, and thereby the above-mentioned problem is solved. Particularly, in a disposable diaper for adult, this tendency is strong from the viewpoint of facts that a high fastening strength is required and the like. As shown in FIG. 62, as the concrete example of the surface fastener type as the second prior example, there is one such that a hook portion 7 is provided on the inner side of the portion extended from the edge side to the outside of a flap F, a peeling tape 8 having a hook receptacle portion on the inner side of the flap F is provided and a hook portion 7 with a product unused is temporarily fixed at the peeling tape 8 in place. In addition, there is another one such that no peeling tape 8 is provided and a hook portion 7 is allowed to be tangled with the inner non-woven fabric of the flap portion F and is temporarily fixed in place.

However, since in the first prior example, a peeling tape is indispensable as described above, there is a problem such that a cost was increased by a portion of the arrangement of the peeling tape.

On the contrary to this, in the second prior example, the surface fastener-type fastening tape is excellent in repeatable detachability.

Therefore, since in each prior example, a non-air permeable adhered tape is provided on the surface of the fastening region on a belly side, it has problems such that this inhibits the air permeability on the belly side and the appearance is not neat.

In addition, although the inventors have considered an engagement where a direct entanglement with a back sheet is performed without using an adhered tape, the inventors have encountered a problem such that there is no mark of a region to which an engagement portion is to be fastened.

Accordingly, another object according to the present invention is to form a marked portion (target) on the external surface of a region to which the engagement portion is to be fastened although an adhered tape is not used. Moreover, another object is to provide a form where the appearance may not deteriorate although a distortion processed portion is formed in a large area. Furthermore, another object is to enable a user to engage and fix a fastening tape at a free position without paying a care to the engagement position of the fastening tape as a result. Moreover, another object is to provide a form where a cottony state can be prevented although the repeatable engagement and fixation of a fastening tape is performed when the external surface of a belly side is formed with a non-woven fabric. Further, other objects may be estimated from the descriptions below.

DISCLOSURE OF THE INVENTION

In order to solve the above-mentioned objects, in accordance with a first aspect of the present invention, the absorbent body contains a super absorbent polymer and an absorbent fiber and is thinned by pressurization, wherein the super absorbent polymer has a gel elastic modulus of not less than 2,000 N/m$^2$ according to a gel elastic modulus test and has an artificial urine absorption amount of not less than 32 cc/g according to an absorption test under pressure at 20 g/cm$^2$, and a ratio of the super absorbent polymer to a total weight of the super absorbent polymer and the absorbent fiber is not less than 40 wt %.

In case of a super absorbent polymer with a low gel elastic modulus and a low, artificial urine absorption amount under pressure, if the content is set in a range of 40 to 80 wt %, an absorption amount decreases due to the densification of the structure and gel blocking. On the other hand, if the content of a super absorbent polymer is set in less than 40 wt %, an absorption amount lowers due to its low content although the densification of the structure and the affection of gel blocking can be reduced.

Therefore, if a super absorbent polymer having a gel elastic modulus and an artificial urine absorption amount under pressure that are not less than a predetermined value is used according to the present invention, although its content is large, it is hardly affected by the densification according to pressurization since an artificial urine absorption amount under pressure is basically large, when thinning by pressurization is performed, and moreover, gel blocking is hardly generated due to its high gel elastic modulus. Therefore, an absorbing performance equivalent to that of in earlier technology, which is not thinned, can be exerted while thinning by pressurization is promoted.

In addition, an absorption test under pressure and a gel elastic modulus test referred to in the present invention will be explained in the later-described Examples.

It is preferred that for the super absorbent polymer of the absorbent body, an absorption rate of artificial urine of 30 cc according to an absorption rate test is not more than 60 sec./g.

In the present invention, although the content of a super absorbent polymer can be made to be not less than 40 wt % without reducing an absorption amount as described above, the rate of absorption rate as an absorbent body lowers since the content of the absorbent fiber having a high absorption rate lowers in this case. Therefore, particularly, the more the content of the super absorbent polymer is increased, it is desirable to prevent the absorption rate as an absorbent body from lowering by using the super absorbent polymer having a high absorption rate. In addition, the absorption rate test referred to in the present invention will be explained in the later-described Examples.

It is preferred that for the super absorbent polymer of the absorbent body, a value according to a gel permeability rate test is not more than 100 sec. per a permeation amount of 50 cc and not more than 300 sec. per a permeation amount of 100 cc.

By allowing the range to be kept as above, liquid can be smoothly permeated, and the absorbing performance which an absorbent-body inherently has can be sufficiently exerted. In addition, a gel permeability rate test referred to in the present invention will be explained in the later-described Examples.

Preferably, the super absorbent polymer of the absorbent body is particles of super absorbent polymer in which a number of particles having a particle diameter of not more than 250 μm is not more than 20% to a number of whole particles.

By allowing the scope to be kept as above, the voids of particles when the particles absorb liquid and are swollen hardly become smaller, and the liquid can be smoothly permeated. Thereby, the absorbing performance which the absorbent body inherently has can be fully exerted.

Thinning by pressurization can be performed on the absorbent body so as to allow a density to be not less than 300 kg/m$^3$.

Although the above higher density is promoted, in case of the present invention, the characteristics of the afore-mentioned super absorbent polymer can equalize the absorbing performance with that of in earlier technology, which is not thinned.

For the absorbent body, a value measured in a stiffness test can be not more than 10 mm.

By allowing the scope to be kept as above, flexibility is fully provided while thinning is promoted, and the absorbent body fits the motion of a human body, and the absorbent body excellent in wearing property can be obtained. In addition, a stiffness test referred to in the present invention will be explained later.

The absorbent body can be an air laid absorbent body obtained by accumulating and forming the absorbent fiber and the super absorbent polymer while disentangling and mixing them according to an air laying method, and performing thinning by pressurization.

Even in the air laid absorbent body where the absorbent fiber and the super absorbent polymer are evenly mixed according to the air laying method, the above-mentioned cause and effect can be expressed.

In accordance with a second aspect of the present invention, a method for manufacturing an absorbent body is that an absorbent fiber and a super absorbent polymer are accumulated and formed while they are disentangled and mixed according to an air laying method and thinning by pressurization thereby to obtain the absorbent body, wherein the super absorbent polymer has a gel elastic modulus of not less than $2,000\ N/m^2$ according to a gel elastic modulus test and an artificial urine absorption amount of not less than 32 cc/g according to an absorption test under pressure at 20 $g/cm^2$.

With the manufacturing method, an absorbent body where the super absorbent polymer and absorbent fiber are evenly mixed can be manufactured at a high efficiency. In addition, the absorbent body manufactured by this method can express the same cause and effect as in the absorbent body according to the afore-mentioned present invention.

In accordance with a third aspect of the present invention, the absorbent article comprises any one of the above-mentioned absorbent bodies.

The absorbent body according to the present invention can be preferably used as the absorbing elements of absorbent articles such as disposable diapers, sanitary napkins, incontinence pads, medical pads and the like, and the afore-mentioned cause and effect can be expressed in this case.

In the absorbent article, no elastic member may be located inwardly from a portion corresponding to a vicinity of a side edge of the absorbent body.

Although this kind of absorbent article, among them, a disposable diaper is provided with an elastic member to aim at increasing a fitting property or the like, a constitution that no elastic member is located inwardly from a portion corresponding to the vicinity of the side edge of the absorbent body allows the absorbent body to be hardly shrinkable, thereby the thinness of the article can be kept as it stands.

In accordance with a fourth aspect of the present invention, the disposable diaper in which their both side edge portions at a front side and a back side of an external sheet are bonded thereby forming a waist opening portion and right and left leg opening portions in a use state, comprises the above-described absorbent body in a center portion thereof, wherein the disposable diaper is formed so as to allow side ends of a crotch-portion of the external sheet to be located within 5 mm from side ends of a crotch portion of the absorbent body.

If a thinned absorbent body according to the present invention is adopted in a disposable diaper particularly, the voluminous feeling and swelling feeling of the disposable diaper (particularly, of the crotch portion) are reduced due to its thinness and the appearance is very neat. In addition, by forming the diaper so as to allow the side ends of the crotch portion of the external sheet to be located within 5 mm from the side ends of the crotch portion of the absorbent body, the external sheet scarcely protrudes from the side of the absorbent body, and the voluminous feeling and swelling feeling of the crotch portion are further reduced, thereby the appearance can be further neat.

In accordance with a fifth aspect of the present invention, the disposable diaper comprises a fastening tape where a tape substrate is provided with an engagement portion, the fastening tape being mounted on each of both side portions of a back side of a product, and each the engagement portion being mechanically engaged with an external surface of a belly side, wherein a distortion processed portion where distortion in an appearance is furnished by machining is formed on the external surface itself of the belly side to be a target of the engagement portion.

Since a surface fastener-type fastening tape is used, it is excellent in repeatable fastening property. In addition, since the distortion processed portion is formed on a region with which the engagement portion on the external surface of the belly side is engaged, this is a target (mark) with which the engagement portion is to be engaged, and a marked portion can be easily formed on the external surface of the belly side at a region with which the engagement portion is to be engaged although an adhered tape is not used. In addition, although the distortion processed portion is formed in a broad area, the appearance is not bad like a case that an adhered tape as another member is attached. As a result, engagement and fixation can be performed at a free position without paying much attention to the engagement position of the fastening tape.

In the above-mentioned disposable diaper, the external surface of the belly side can be formed by a non-woven fabric.

By forming the external surface of the belly side using a non-woven fabric, it gives a cloth-like feeling as compared to a form that it is formed by a plastic sheet, and the appearance becomes excellent. If a fastening tape is repeatedly engaged with and fixed at the non-woven fabric, a cottony state is likely to take place on the non-woven fabric. However, if the distortion processed portion is formed by particularly performing embossment processing, the fiber composition of the portion is reinforced, and thereby, a cottony state can be prevented.

A processing for the distortion processed portion of the disposable diaper can be selected from embossment processing, crepe processing and bellows processing.

In the disposable diaper, the external surface of the belly side may be formed by a non-woven fabric having an air permeability, the distortion processed portion may be formed to the non-woven fabric, and further, a material which inhibits the air permeability may not be provided in at least one portion of the distortion processed portion.

By adopting a constitution that the distortion processed portion is formed to the non-woven fabric having an air permeability, and further, a material which inhibits an air permeability is not provided in at least one portion of the distortion processed portion, an air permeability can be secured and a non-breathing accompanied by the discharge of a body fluid can be prevented.

The distortion processed portion may be formed as separated in a body peripheral direction.

The distortion processed portion may be easily recognized as the mark of the fastening region of the engagement portion by forming as separated the portion in the body peripheral direction.

BRIEF DESCRIPTION OF DRAWINGS

FIGS. 20A to 20F are explanatory views of the disposition forms of elastic members.

FIG. 21A and FIG. 21B are views showing the design examples of the front and back sides of the shorts-type diaper product.

FIG. 32 is a plan view as viewed from the use surface for the developed state of an embodiment provided with another elastic member.

FIG. 41 is a side view of a fastening tape portion when a diaper is put on.

FIG. 42 is a perspective view of a disposable diaper when disposed of.

FIG. 56 is a view to show the fourth step of the first manufacturing form.

FIG. 59 is a view showing the third step of the second manufacturing form.

BEST MODE FOR CARRYING OUT THE INVENTION

Figure 1:
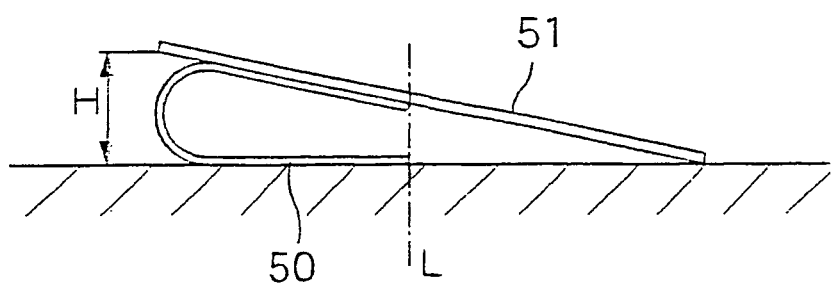
FIG. 1 is a side view to explain the manual of the stiffness test.

The embodiments according to the present invention are detailedly described below referring to the drawings.
(Regarding Absorbent Body)

As described above, an absorbent body according to the present invention contains a super absorbent polymer and absorbent fibers and is thinned by pressurization.

As absorbent fibers used in the present invention, cellulose fibers such as chemical pulps, dissolving pulps and the like obtained from lumber, and artificial cellulose fibers such as rayon, acetates and the like are given. Conifer pulps of longer fibers are more preferably used than broad leaf tree pulps from the viewpoints of functions and cost.

In addition, preferably used as super absorbent polymers in the present invention are carboxymethylcellulose, polyacrylic acid and its salts, crosslinked acrylate polymer, starch-acrylate graft copolymer, hydrolysate of starch-acrylonitrile graft copolymer, crosslinked polyoxyethylene, crosslinked carboxymethylcellulose, partially crosslinked compounds of water swelling polymers such as polyethylene oxide, polyacrylamide and the like, or copolymers of isobutylene with maleic acid and the like. A super absorbent polymer to which a blocking inhibitor is added to suppress a blocking property caused by the moisture absorption of a product can be also used. In addition, although super absorbent polymers are of various forms such as powder-like, particle-like, granule-like, pellet-like, sol-like, suspension-like, gel-like, film-like, non-woven fabric-like and the like, any of these can be used in the present invention and particularly, particulate ones are preferably used.

On the other hand, besides the above-mentioned major constituent absorbent fibers and super absorbent polymers, adhesive, diffusing agent, deodorant, absorbent fibers and the like can be contained.

In the present invention, a super absorbent polymer with a gel elastic modulus of not less than 2,000 $N/m^2$ according to a gel elastic modulus test and an artificial urine absorption amount of not less than 32 cc/g according to an absorption test under pressure at 20 $g/cm^2$ is characteristically used. Particularly preferred is a super absorbent polymer having a gel elastic modulus of not less than 3,000 cc/g and an artificial urine absorption amount of not less than 35 cc/g. In the present invention, not less than 40 wt % of the above-described super absorbent polymer of is contained to the total weight of the super absorbent polymer and the absorbent fibers. A particularly preferred range is 40 to 80 wt %.

In case of a super absorbent polymer with a low gel elastic modulus and a low artificial urine absorption amount under pressure, although the content is in a range of 40 to 80 wt %, an absorption amount decreases due to the densification of the structure and gel blocking. On the other hand, the content of the super absorbent polymer is less than 40 wt %, although the affection of the densification of the structure and gel blocking can be reduced, an absorption amount decreases due to the small content.

Therefore, if a super absorbent polymer having a gel elastic modulus and artificial urine absorption amount under pressure of not less than predetermined values is used in accordance with the present invention, even though the content is large, when the super absorbent polymer is thinned by pressurization, not only the polymer is hardly affected by the densification by pressurization since the artificial urine absorption amount under pressure is basically large but also the gel blocking of the polymer is hardly generated due to its high gel elastic modulus. Accordingly, the absorbing performance equivalent to that in earlier technology, which is not thinned, can be exerted while thinning is promoted.

The more preferred super absorbent polymer is one where the rate of absorption of an artificial-urine of 30 cc is not more than 60 sec./g, particularly not more than 55 sec./g. In the present invention, as described above, the content of a super absorbent polymer can be made to be not less than 40 wt % without reducing an absorption amount. However, in this case, since the content of absorbent fibers with a high rate of absorption lowers, the rate of absorption as absorbent body lowers. Therefore, particularly, the more the content of a super absorbent polymer is increased, it is desirable that the rate of absorption as an absorbent body is prevented from lowering by using a super absorbent polymer with a high rate of absorption.

In addition, it is preferred that for a super absorbent polymer, a value according to the later-described a gel permeation rate test is not more than 100 sec. per a permeated amount of 50 cc, particularly not more than 55 sec., and not more than 300 sec. per a permeated amount of 100 cc, particularly not more than 200 sec. For this reason, if particles of super absorbent polymer are particularly used, it is preferred that the number of particles with particle diameter of not more than 250 µm is not more than 20% to the number of whole particles. By keeping the range as the above, liquid can be smoothly permeated and the absorbing performance which the absorbent body inherently has can be fully exerted. If the number of particles of less than the particle diameter exceeds 20%, the absorbing performance lowers since the voids between particles become small when the particles absorb the liquid and are swollen, thereby, the liquid can be hardly permeated.

An absorbent body according to the present invention is obtained by molding the absorbent fibers and the super absorbent polymer described above in a mixed state or molding them so as to allow either of them to form a surface layer and performing thinning by pressurization at the time of the molding or thereafter. It is preferred that in this thinning by pressurization, the basis weight of an absorbent body is set to be not less than 300 gsm with thickness of not more than 2 mm, and the density is set to be not less than 150 $kg/m^3$. The particularly preferred range is that the thickness is 1.0 to 1.5 mmm and the density is not less than 300 $kg/m^3$. In addition, it is preferred that an absorption amount as an absorbent body is set to be not less than 28 cc/g at a normal pressure and not less than 20 cc/g under a pressure of 20 $kg/cm^2$. It is preferred that moreover, a rate of absorption as an absorbent body is set so as to allow the absorbent to absorb artificial urine of 25 cc per 1 g within 10 minutes.

In this connection, the thickness of an absorbent body unless thinning by pressurization is performed is about 2.5 to 3.5 mm. Although the above-described densification is promoted, in case of the present invention, with the characteristics of the afore-mentioned super absorbent polymer, the absorbing performance can be equalized with that of in earlier technology, which is not thinned.

When an absorbent body according to the present invention is applied to absorbent articles such as disposable diapers and the like which are used by allowing the absorbent body to contact with a human skin, it is preferred that an absorbent body with a value measured according to a stiffness test of not more than 10 mm is used. In addition, the stiffness test referred to in the present invention is a test method conducted in such a manner that as shown in FIG. 1, an absorbent body sample 50 with the width and height dimensions of 100 mm×100 mm is folded so as to allow the width to be 50 mm and an edge end is fixed in place matching with the reference line L, an acrylic plate 51 with the dimensions of 100 mm×150 mm and the weight of 60 g is brought over the edge end, the center is fixed in place matching with the reference line H and one side end is allowed to contact with a horizontal plane, the height L of the other side end (on the bent side of the absorbent body) is measured and a value which the bulk of the absorbent body (thickness t×2) is deducted from this height H is determined to be an stiffness index.

Figure 2:
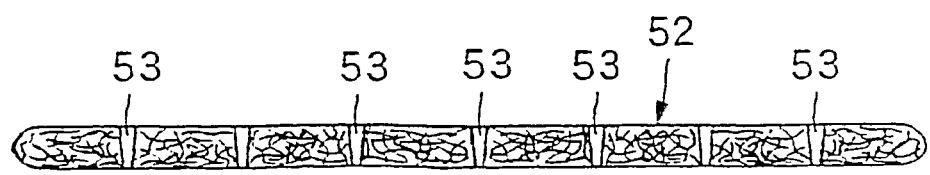
FIG. 2 is a longitudinal cross sectional view typically showing a hole-machined absorbent body.
Figure 3:
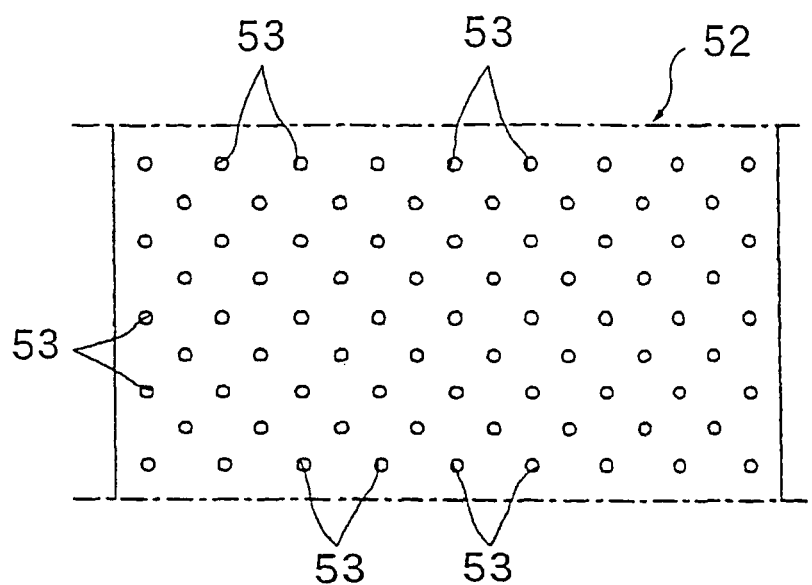
FIG. 3 is a plan view typically showing the hole-machined absorbent body.
Figure 4A:
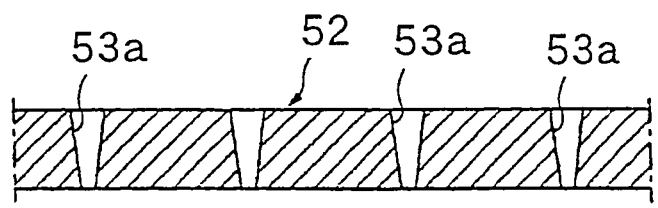
FIG. 4A is a major portion-enlarged longitudinal cross sectional view of an absorbent body where a through-hole is formed.
Figure 4B:
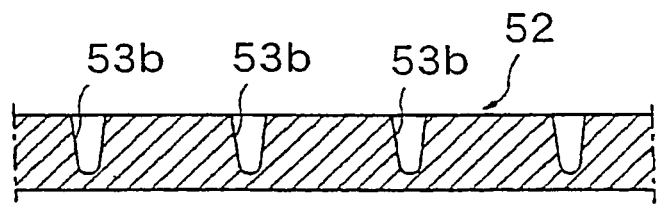
FIG. 4B is a major portion-enlarged longitudinal cross sectional view of an absorbent body where a recessed hole is formed.

If the stiffness exceeds 10 mm, for example, as shown in FIG. 2 and FIG. 3, an adjustment can be made by forming a number of holes 53, 53 - - - on the surface of the absorbent body 52. These machined holes may be through-holes 53$a$, 53$a$ - - - which penetrate through the back side as shown in FIG. 4A, or may be non-through recessed holes 53$b$, 53$b$ - - - as shown in FIG. 4B. The depth of the recessed holes 53$b$ is determined to be not less than 30%, preferably not less than 50%, and more preferably not less than 70% to the thickness of the absorbent body 52. By allowing the depth of the recessed holes 53$b$ to be not less than 30% to the thickness of the absorbent body 52, the differentiation can be promoted from embossment processing such as diamond embossment processing and the like in earlier technology and significant absorbability and flexibility in functionality are shown. In addition, although it is desirable that the shape of these holes 53 is round, the shape may be polygons such as star-shape or triangle, quadrangle or the like. Furthermore, it is desirable that regarding the hole machining, the proportion of not less than 0.1 pc per 1 $cm^2$ is allowed to be given, and the area of the hole is made to be not less than 0.03 $mm^2$ on the surface of the absorbent body.

Figure 5:
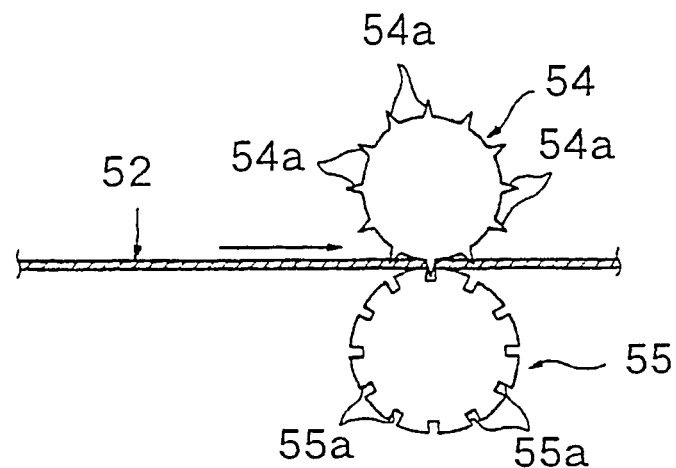
FIG. 5 is a schematic view of a hole machining device.
Figure 6:
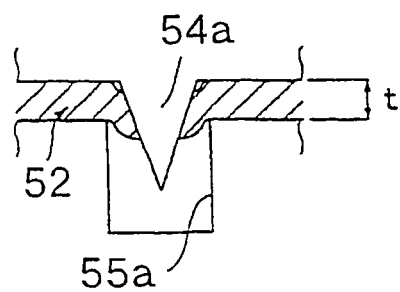
FIG. 6 is a major portion-enlarged longitudinal cross sectional view to explain a hole-machining.

In order to perform the above-described hole machining, as shown in FIG. 5, a hole machining roll 54 having a number of protrusions 54$a$, 54$a$ - - - on the surface of the roll and an anvil roll 55 having recess portions 55$a$, 55$a$ at a position corresponding to the protrusions 54$a$, 54$a$ - - - of this hole machining roll 54 are disposed so as to face to each other, and the absorbent body 52 (including the absorbent body sheet) is allowed to pass between both rolls 54 and 55. In the passage portion of the absorbent body 52 as shown in FIG. 6, the protrusion 54$a$ is fitted in the recess portion 55$a$, and the through-hole 53$a$ which penetrates through the back side of the absorbent body 52 or a non-through recessed hole 53$b$ is formed. A needle-like (needle) or conical protrusion is preferred as the protrusion 54$a$ for hole machining roll.

(Regarding Manufacture of Absorbent Body)

Although there are various methods to manufacture an absorbent body according to the present invention, it is preferable that in an air laying method that both absorbent fibers and super absorbent polymer are accumulated by air flow and are formed together from the viewpoints of the equalization of mixing of fibers and SAP and high manufacturing efficiency.

Figure 7:
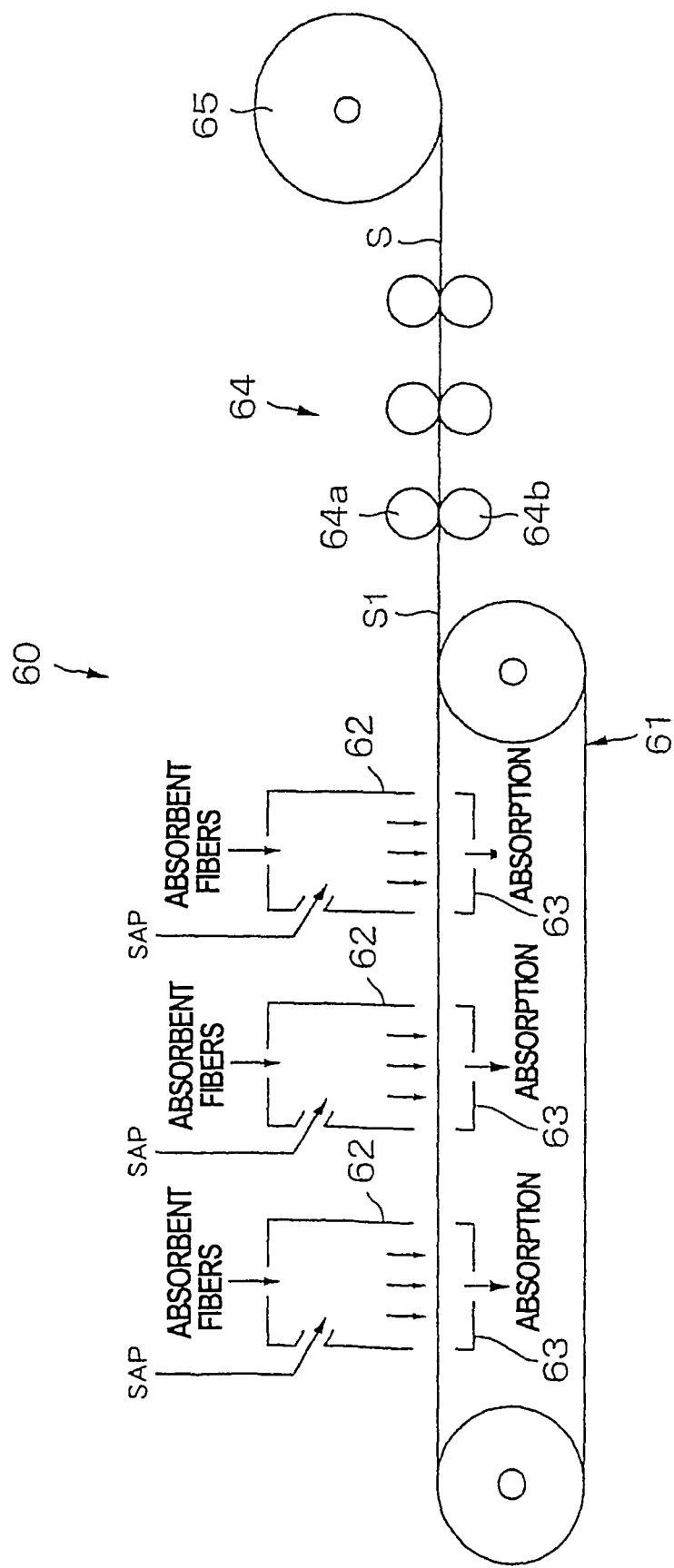
FIG. 7 is a schematic view of a manufacturing device to manufacture an absorbent body according to the present invention.

The outline of the manufacturing device therefor is shown in FIG. 7. This manufacturing device 60 comprises an endless belt conveyor 61 having an air permeable structure; a plurality of dispersing chutes 62, 62 - - - spaced out and disposed in the transfer direction in the upper side of this endless belt conveyor 61; a belt conveyor-type air laying portion comprising a plurality of sucking devices 63, 63 - - - disposed at a position corresponding to each dispersing chute 62, 62 - - - in the back side of the conveyor 61; a heating-and-pressing roll group 64 which performs thinning by pressurization on an accumulated material discharged from this air laying portion and performs bonding between fibers; and a winding roll 65 which winds a formed sheet S after thinned by pressurization.

In this device, the absorbent fibers and super absorbent polymers are conveyed in the air flow and are injected into the same dispersing chutes 62, 62 - - - respectively, and these compounds are accumulated and formed as a web on the conveyor 61 by sucking them from the back side of the conveyor 61 while they are disentangled and mixed. Next, this web S1 accumulated and formed is transferred from an endless collecting conveyor 61 to the heating-and-pressing roll group 64, and after thinning by pressurization and bonding between fibers are performed by sandwiching the web between the heating-and-pressing rolls 64$a$ and 64$b$ and an air laid absorbent body sheet S according to the present invention is prepared, the sheet is wound by the winding roll 65. When this winding roll 65 is, for example, applied to an absorbent article, this roll is brought in the manufacturing line of the absorbent article and this sheet is unwound, and the sheet is then cut into a predetermined shape or the like and a piece cut from the sheet is attached to the absorbent article.

In addition, although not illustrated, this absorbent body manufacturing line can be incorporated into the manufacturing line of the absorbent article, a formed absorbent body sheet as it stands can be intermittently or continuously supplied to the manufacturing line of the absorbent article without winding the sheet. Then, after the sheet is cut into a predetermined shape or the like there and a cut piece is attached to an absorbent article and the absorbent body sheet can be cut into a predetermined shape without winding the sheet, the cut sheet can be intermittently or continuously supplied to the manufacturing line of the absorbent article and the sheet can be also attached to the absorbent article there.

Figure 8:
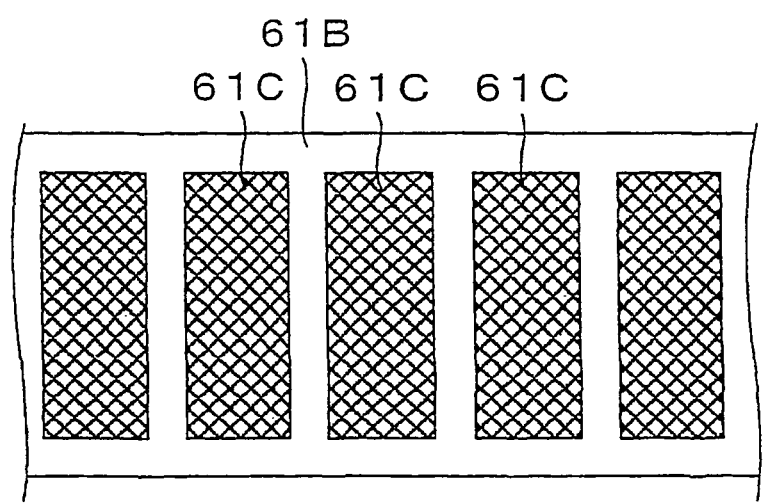
FIG. 8 is a major portion plan view of a belt for a belt conveyor.
Figure 9:
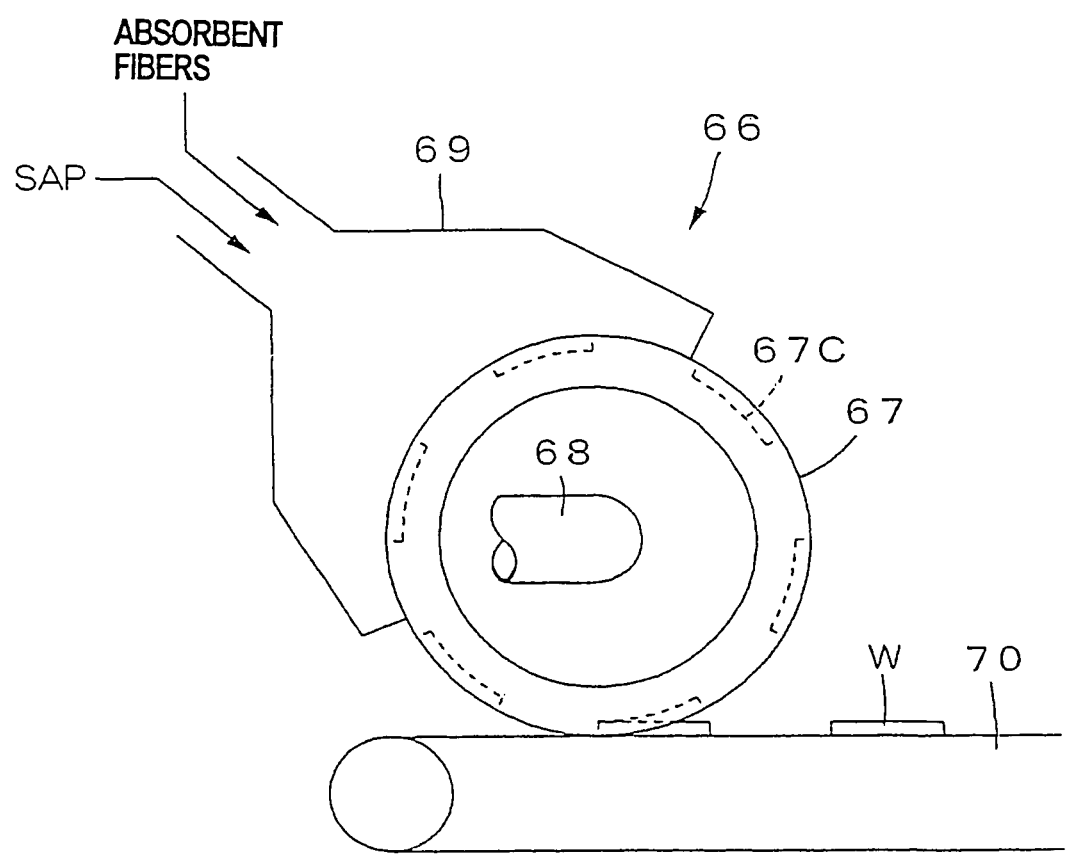
FIG. 9 is a front view of a drum-type air laying device.

In the above example, since an absorbent body is manufactured as a sheet, it is necessary to cut the sheet into a suitable shape thereafter. In this regard, as shown in FIG. 8, it is desirable that a plurality of absorbent body-shaped recess portions 67C, 67C - - - are provided on the periphery of the belt 61B in the above-described belt conveyor in the peripheral direction, and the constitution is so arranged that sucking and accumulation are performed so as to allow only the inside of these recess portions to be of an air permeable structure. In addition, in place of the air laying portion in FIG. 7, as shown in FIG. 9, a drum air laying device 66 comprising a drum 67 having a plurality of absorbent body-shaped recess portions 67C, 67C - - - on the periphery in the peripheral direction; a sucking member 68 which sucks the external air into the internal portion through the recess portions 67C, 67C - - - of this drum 67; and a dispersing chute 69 which opens facing the periphery of the drum can be also used. In addition, the numeral 70 in FIG. 9 shows a conveyor which conveys an accumulated material discharged from the drum recess portions 67C, 67C - - - to the next pressurizing process.

In the examples as shown in FIG. 8 and FIG. 9, since an absorbent body can be formed into a predetermined shape at the time of accumulation, it has an advantage such that cutting in subsequent processes is unnecessary as well as another advantage such that it is easier to incorporate a sheet into the manufacturing line of the absorbent article. Thus, it is preferred that an absorbent body according to the present invention is manufactured by an air laying method which accumulates both the absorbent fibers and the super absorbent polymers with air flow. However, an absorbent body (including its whole cloth) formed by well-known methods, for example, a method for polymerizing a monomer, which becomes a super absorbent polymer after impregnating the monomer into a non-woven fabric comprising absorbent fibers, a method for performing crosslinking processing after coating a non-crosslinked gel-like super absorbent polymer on a non-woven fabric comprising absorbent fibers, and a wet method for forming a sheet by using a dispersing solution where a super absorbent polymer is dispersed in slurries such as pulps or the like, and the like, can be manufactured by performing thinning by pressurization with a suitable pressing device.

<Regarding Absorbent Article>

In the present invention, ones such that the above-mentioned absorbent body is applied as an absorbing element of absorbent articles such as disposable diapers, sanitary napkins, incontinence pads, medical pads and the like are proposed.

Figure 10A:
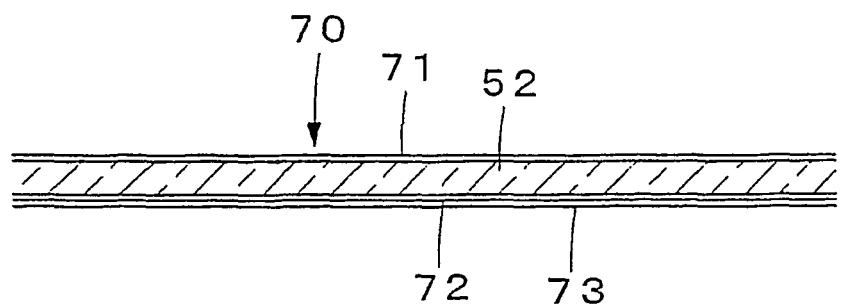
FIG. 10A is a major portion-enlarged longitudinal cross sectional view of an absorbent article to which a thinned absorbent body according to the present invention is applied.

In the above-described absorbent articles, as shown in FIG. 10A, normally, an absorbent body 52 is attached to an external sheet 73 as an absorbing element 70 in as state such that the absorbent body 52 is enclosed with a tissue paper or the like and is sandwiched between a liquid-permeable top sheet 71 and a non-liquid permeable back sheet 72.

Figure 10B:
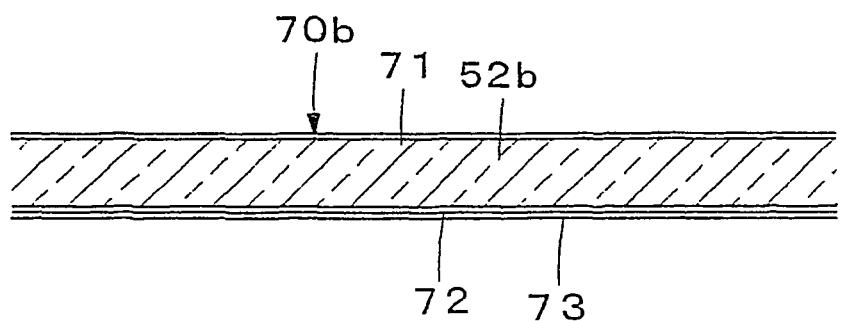
FIG. 10B is a major portion-enlarged longitudinal cross sectional view of an absorbent article to which a non-thinned absorbent body is applied.

In this constitution example, since the thickness of the portions other than the absorbent body is normally not less than 0.5 mm, if, for example, the thickness of the absorbent body 52 is thinned to 2.0 mm by pressurization, the proportion of the absorbent body 52 in the thickness direction can be made to be not more than 80%. However, as shown in FIG. 10B, the proportion exceeds 80% in an absorbent article 140' where an absorber 110 in earlier technology, which is not thinned by pressurization, is used. In addition, it is preferred that the thickness of the absorbent body according to the present invention is not more then 3.0 mm, particularly preferred is not more than 2.0 mm.

Although the details of the absorbent body 52 according to the present invention are justly omitted here since they are already described, it is preferred that for an absorbent article which is used while contacting with a human skin, an absorbent body with a value measured according to a stiffness test of not more than 10 mm is used.

For the non-liquid permeable back sheet 72, for example, a non-liquid-permeable sheet comprising a polyethylene sheet and the like, a waterproof/moisture permeable sheet having a moisture permeability from the viewpoint of prevention of stuffiness, and a composite sheet comprising a non-woven fabric and a waterproof sheet, and the like are further used. On the other hand, for the liquid-permeable top sheet 71, a foraminiferous or imperforate non-woven fabric or a porous plastic sheet and the like are preferably used. For material fibers comprising the non-woven fabric, synthetic fibers such as olefins such as polyethylene, polypropylene and the like, polyesters, polyamides and the like, regenerated fibers such as rayon, cuprammonium rayon and the like, natural fibers such as cottons and the like can be used, and the non-woven fabrics obtained by a suitable processing method such as span lace method, span bond method, thermal bonding method, melt blow method, needle punch method or the like can be used.

An air laid absorbent body according to the present invention is particularly preferable for a disposable diaper among absorbent articles. Therefore, next, for a disposable diaper to which the air laid absorbent body according to the present invention can be applied, in the first place, the detailed descriptions are given by taking up the example of a shorts-type disposable diaper, thereafter, also described is an application example to a type, a so-called tape-type disposable diaper that when the diaper is used (at the time of putting on), both side edge portions in the right and left on the back side are brought in both side edge portions in the right and left on the belly side and these portions are bonded with a tape fastener (including an adhesive tape fastener and a surface fastener).

First Embodiment

The terms relating to the regions and directions according to the present invention will be explained mainly according to FIG. 11, and a shorts-type disposable diaper in a first embodiment according to the present invention will be explained according to FIG. 12 and FIG. 13.

Figure 11:
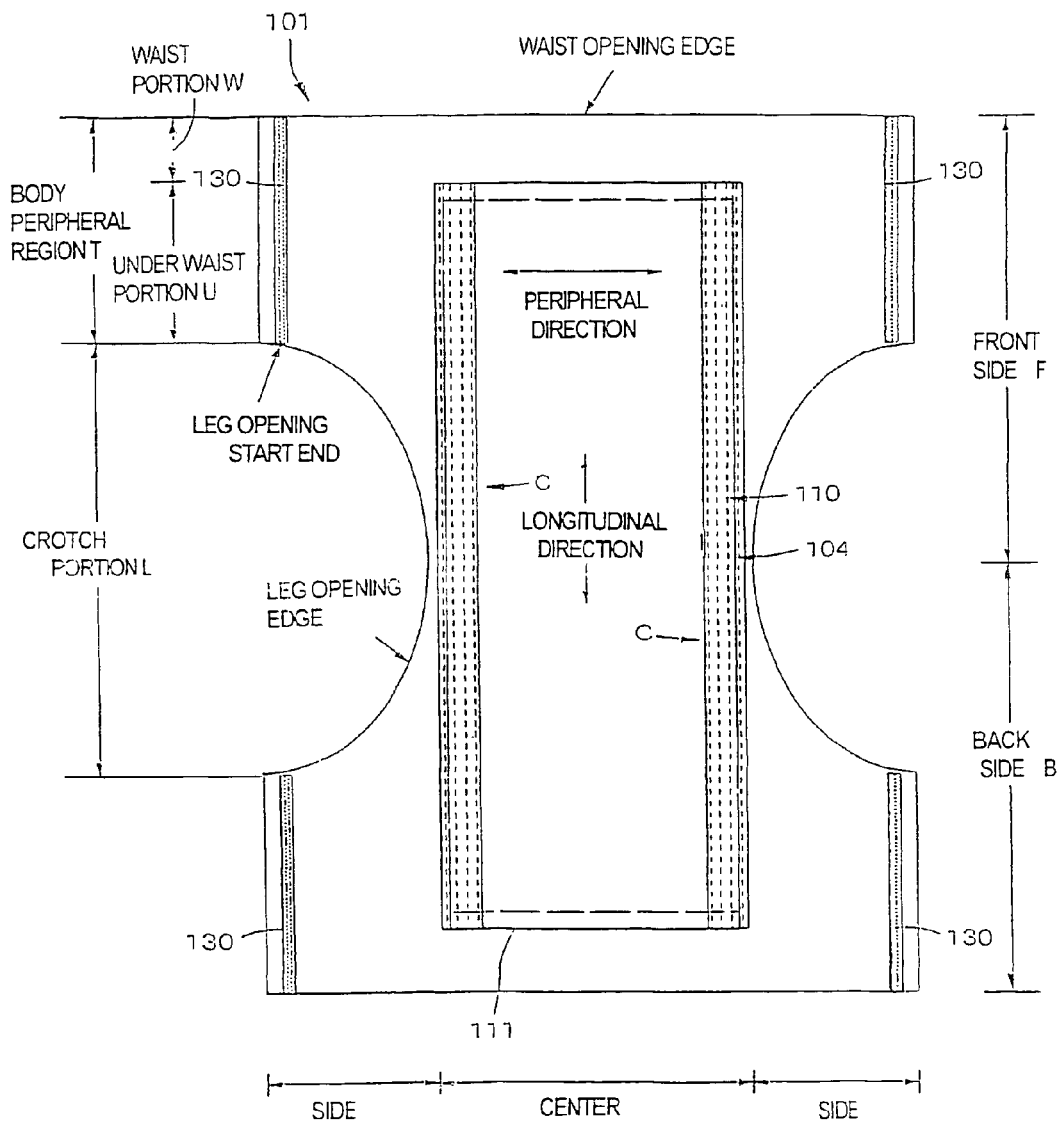
FIG. 11 is a plan view as viewed from the use surface for the developed state of a shorts-type diaper showing a first embodiment according to the present invention for explanation of the terms.
Figure 12:
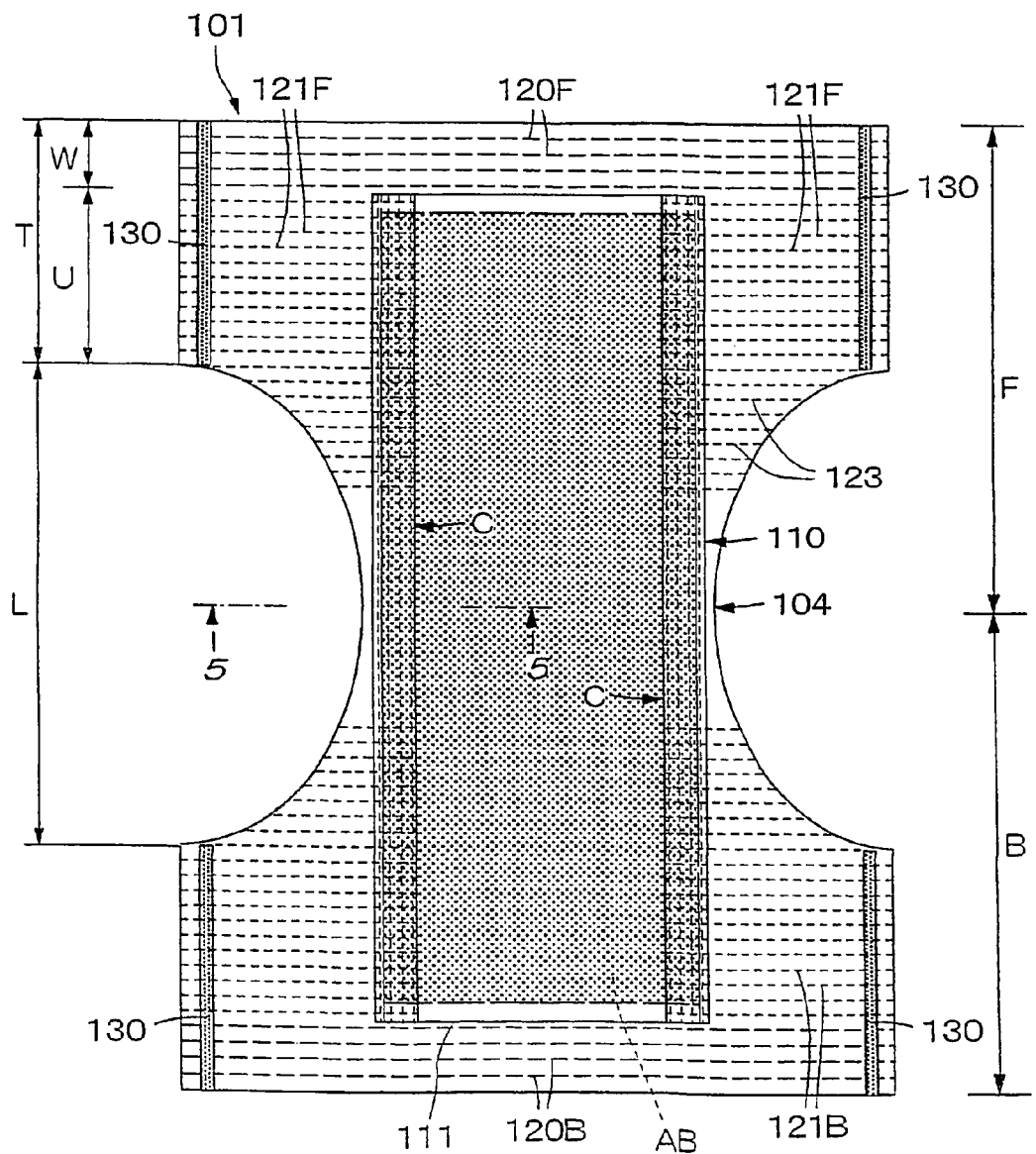
FIG. 12 is a plan view as viewed from the use surface for the developed state of a shorts-type diaper showing the first embodiment according to the present invention.

The shorts-type disposable diaper in the first embodiment mainly comprises a flexible external sheet 101 and an absorber 110 which is fixed in place on the inner surface of this external sheet 101 and is extended in the longitudinal direction (in the forward and backward direction) by making the crotch portion (inside leg) 104 be center, as shown in FIG. 11 and FIG. 12.

Figure 14:
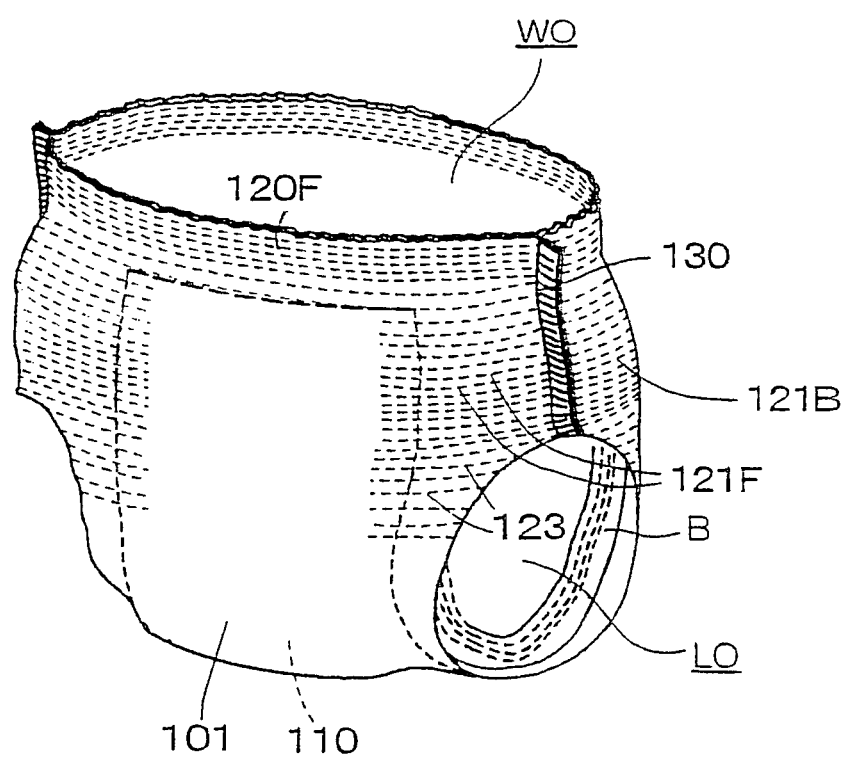
FIG. 14 is a perspective view showing the use state of the shorts-type diaper according to the present invention.

The external sheet 101 comprises air permeable/water-repellent non-woven fabrics of two or three sheets or more which are laminated and fixed in place, a waist opening portion WO and a pair of leg opening portions LO in the left and right sides as shown in FIG. 14 are formed by bonding the entire longitudinal direction of both side edges in the front side F and the back side B with a member such as a ultrasonic wave sealing or a thermal melting (the bonded portion indicated as numeral 130) in the final step of the manufacturing process after this external sheet 101 and the absorber 110 are superimposed.

In the symbols in FIG. 11, "the longitudinal direction" means the direction which connects the belly side and the back side, and "the peripheral direction" means the direction which intersects with the longitudinal direction. "The waist opening edge" means the edge of the waist opening portion WO, and "the leg opening edge" means the edge of the leg opening portion LO. "The leg opening start end" means a position where the leg opening edge of the leg opening portion LO intersects with the bonded portion 130 and also means the start position of the leg opening edge. "The body peripheral region" T means the entire area of a longitudinal range from the waist opening edge to the leg opening start end. The body peripheral region T can be conceptually divided into "the waist portion" W and "the under waist portion" U. Although the lengths in the longitudinal direction are different depending upon the sizes of products, the waist portion W is 15 to 40 mm and the under waist portion U is 45 to 120 mm. "The crotch portion" L means the entire area of a longitudinal range which forms the leg opening portion LO. In addition, "the center" means the intermediate area excluding the side portion which includes the center line of a product. "The side" means both sides in the body peripheral region T.

Figure 13:
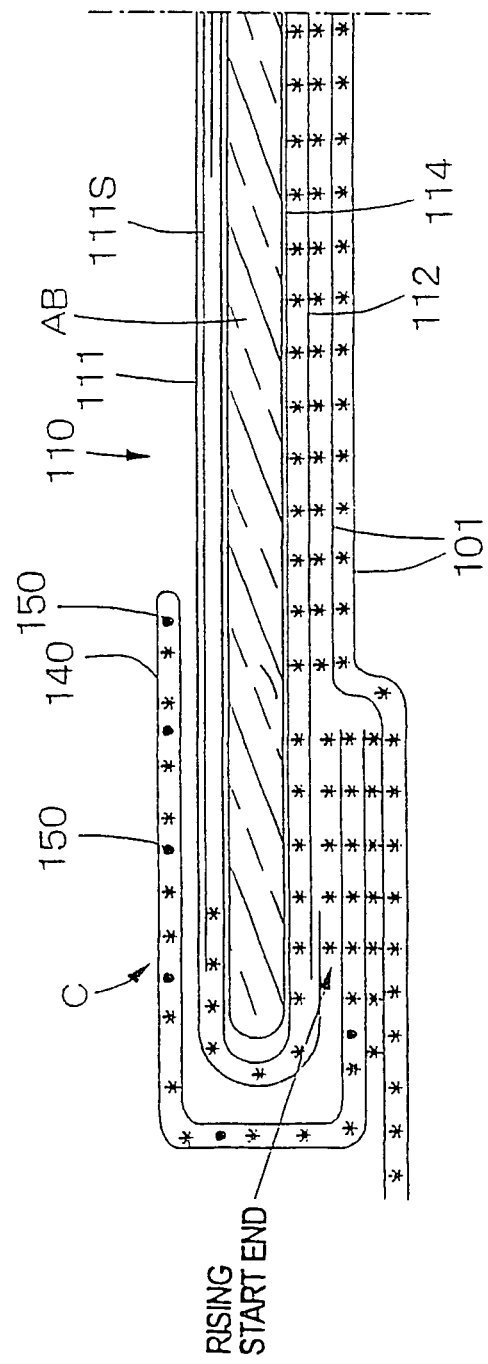
FIG. 13 is a longitudinal cross sectional view by a 5-5 arrowed line of FIG. 12.

The absorber 110, as also shown in FIG. 13, mainly comprises a rectangular liquid-permeable top sheet 111 which comprises a non-woven fabric and the like and directly contacts with the skin of a wearer; and a floc pulp. The absorber 110 has a rectangular pressurized/thinned-type absorbent body AB of the present invention which has a certain rigidity (semirigid) and the entire upper and lower surfaces of which enclosed with a rectangular crepe paper 114; and a rectangular non-liquid permeable back sheet 112 comprising a polyethylene plastic film or the like which reaches the vicinity of both side edges on the back side of the absorbent body AB. The liquid-permeable top sheet 111 rounds about both side edges of the absorbent body AB to reach the back side and is superimposed on anon-liquid permeable back sheet 112, and these elements are bonded with a hot melt adhesive (the portions which are marked with * are bonded portions), and they are thus integrated as a whole. A liquid-permeable second sheet 111S can be interposed between the liquid permeable top sheet 111 and the crepe paper 114 as illustrated, whenever necessary. The almost entire back side of this absorber 110 is bonded to the external sheet 101 with a hot melt adhesive and they are thus integrated as a whole.

Leg rising cuffs C and C which protrude toward the use surface are each formed on both sides of the absorber 110, and this rising cuff C substantially comprises a rising sheet 140 which continues in the width direction and an elastic member, for example, one piece of an elastic member made of rubber thread or a plurality of elastic members 150, 150 - - - as illustrated.

For more detailed description, the rising cuff C is formed by doubly forming the rising sheet 140 and enclosing each elastic member 150, 150 - - - with them bonded thereto with a hot melt adhesive or the like. It is desirable that the rising sheet 140 which forms each rising cuff C and C is not liquid-permeable, but is non-liquid permeable or hydrophobic. For that reason, the constitution may be also the one which increases a leakage preventability by lining another sheet (film, a non-woven fabric or the like) on the inner surface of the rising sheet 140. The sheet may be of liquid-repellency by performing silicone processing on a liquid-permeable sheet such as non-woven fabric or the like. Further, it is desirable that the sheet is air-permeable or steam-permeable.

The inner surface of the double-rising sheet 140 rounds about the back side of the absorbent body AB and the non-liquid permeable back sheet 112 and is fixed in place with a hot melt adhesive or the like. As a result, this fixation start end of the double-rising sheet 140 forms the rising end of the rising cuff C.

The top side from this rising end is a free portion which is not fixed in place at the body of the product.

On the other hand, forward and backward end portions in the longitudinal direction, the free portion is fixed in place at the article with the tip of the free portion extended toward the center of the article, concretely, it is fixed in place at the external surface of the liquid-permeable sheet 1 with a hot melt adhesive or the like.

In addition, although the elastic members 150, 150 - - - are of the basic form that at least one piece is provided in the free portion, it is preferred that particularly, the elastic member 150 is provided at the tip of the free portion, further, it is preferred that the elastic member 150 is also provided on the root side as shown in FIG. 13. It is further preferable that a plurality of elastic members are provided at the tip as illustrated.

FIG. 12 shows a disposable diaper in as state developed in the longitudinal direction. Since the disposable diaper is put on a human body in the form of a ship at the time of putting-on and the contractile force of each elastic member 150, 150 - - - acts, the rising cuff C rises by the contractile of each elastic member 150, 150 - - - around the legs, with the forward and backward ends of the product kept as it stands. In this case, the side portions of the absorber 110 are distorted and is raised, and the absorbent body AB is also raised while it is somewhat distorted to form a deep pocket space.

The space enclosed by the rising cuffs C and C in the right and left sides forms a containment space for urine or soft feces. If a wearer discharges urine in this space, the urine is absorbed in the absorbent body AB through the liquid-permeable top sheet 101 and overflowing of the solid of the soft feces can be prevented by the rising cuff C functioning as a barrier.

On the other hand, waist elastic members 120F and 120B comprising a thin rubber thread which are juxtaposed to and spaced out from the waist opening WO are disposed and are fixed in place in an extended state so as to allow the members 120F and 120B to be expanded and contracted, in order to increase the fitness of the product to the waist of a wearer between the non-woven fabrics of the external sheet 101 in the waist portion W, at the end portions in the longitudinal direction of the front side F and the back side B. Although a distance between the waist elastic member 120F and 120B and the number of members in the waist portion W are suitably decided, it is preferred that for example, the distance is about 4 to 8 mm and the number of members is 4 to 10 pcs.

Furthermore, in this embodiment, the under waist portion members 121F and 121 B are provided along the peripheral direction on the lower belly portion of the front side F and the hip portion of the back main portion B in the under waist portion U which is the region from the waist portion W of the front side F and the back main front B to the crotch portion L. Then, the under waist portion elastic members 121F and 121 B are each provided in the right and left side of the product excluding the almost entire portion of the absorbent body AB out of the portion from the bonded portion 130 of one side to the bonded portion 130 of the other side in the front side F and the back side B.

A thin rubber thread, concretely an elastic member, whose thickness is not more than 620 dtex is used as these under waist portions 121F and 121B, and it is preferred that in both the front side F and the back side B, a distance between elastic members in the longitudinal direction is determined to be not more than 7.0 mm, and 15 to 40 pcs are each juxtaposed and fixed in place between the non-woven fabrics in the external sheet 1. In addition, it is desirable that a mutual distance between these under waist portion elastic members 121F and 121B is the same as or shorter than the waist elastic members 120F and 120B. According to such a constitution, the width of the members is narrow in the peripheral direction, the length of the members is short in the longitudinal direction and the members are continuous in the longitudinal direction, irregularities are scarce, almost non-constrictive wrinkle in the elastic member portion is formed, the wrinkle is not significant, the external surface is not bulky but neat and the member is excellent in the appearance. The portion as a face is pressed against the skin of a wearer, a rubber mark is not left since an excessive compression is not partially applied to the skin, a friction between the inner surface of the product and the skin entirely prevails over the contacting area, the fitness is good by closely contacting with each other and slipping and falling of the product can be better prevented.

In addition, the elastic strain and the diameter of the cross-section of a rubber thread used as these under waist portion elastic members 121F and 121B can be smaller than those of the thin rubber thread used as the above-mentioned waist elastic member 120 or can be substantially the same as in the latter. For the thin rubber thread used here, a rubber thread where the elastic strain is in a range of 4 to 17 g at the time of 150% extension, particularly the stress is in a range of 5 to 10 g is preferably used.

On the other hand, in the first embodiment, a crotch portion elastic member 23 is provided in the right and left portions excluding the center in the crotch portion L. For this crotch portion elastic member 123, an elastic member with thickness of not more than 620 dtex and a distance in the longitudinal direction of not more than 7.0 mm or less determined can be disposed and fixed in place between the non-woven fabrics as in the under waist portion elastic members 121F and 121B.

Second Embodiment

Figure 15:
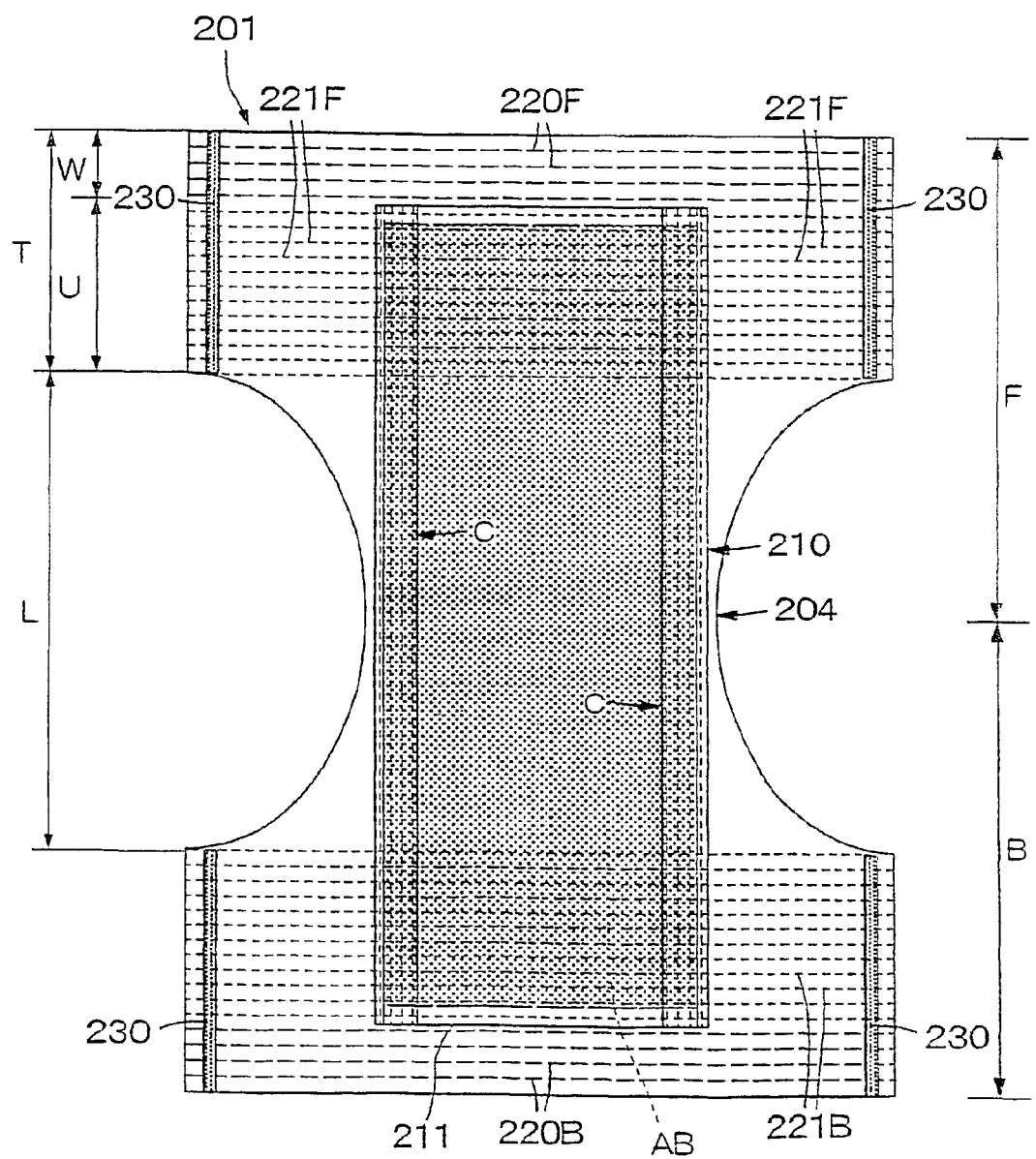
FIG. 15 is a plan view as viewed from the use surface for the developed state of the shorts-type diaper showing a second embodiment according to the present invention.
Figure 16:
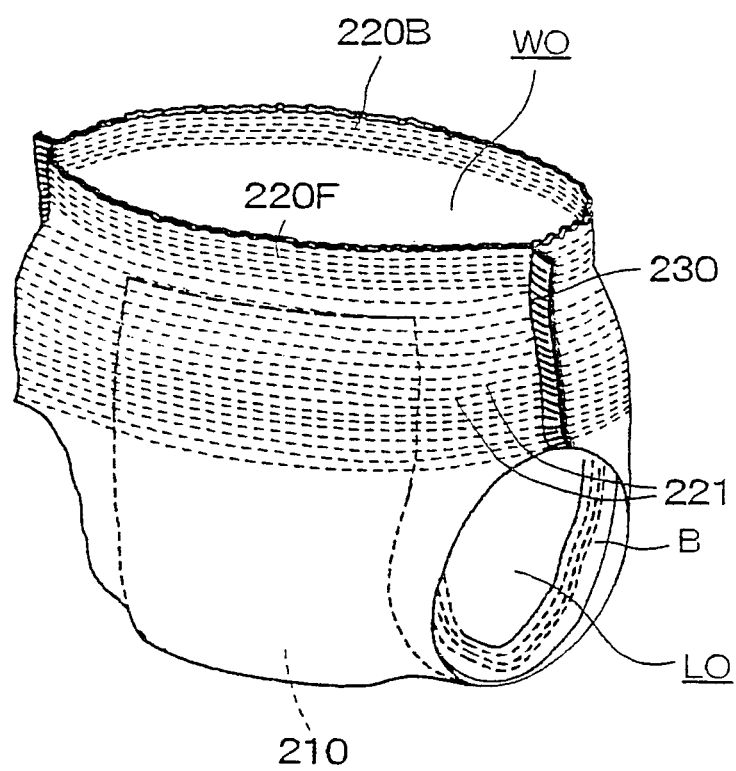
FIG. 16 is a major portion perspective view of the shorts-type diaper showing the second embodiment according to the present invention.

FIG. 15 and FIG. 16 show a shorts-type disposable diaper in a second embodiment according to the present invention. The different points of this embodiment from the first embodiment are that the crotch portion L is not provided with the crotch portion elastic member 123, and in addition, the under waist portion elastic members 221F and 221B are disposed and fixed continuously in the peripheral direction in place between the non-woven fabrics so as to traverse the absorber 210.

Third Embodiment

Figure 17:
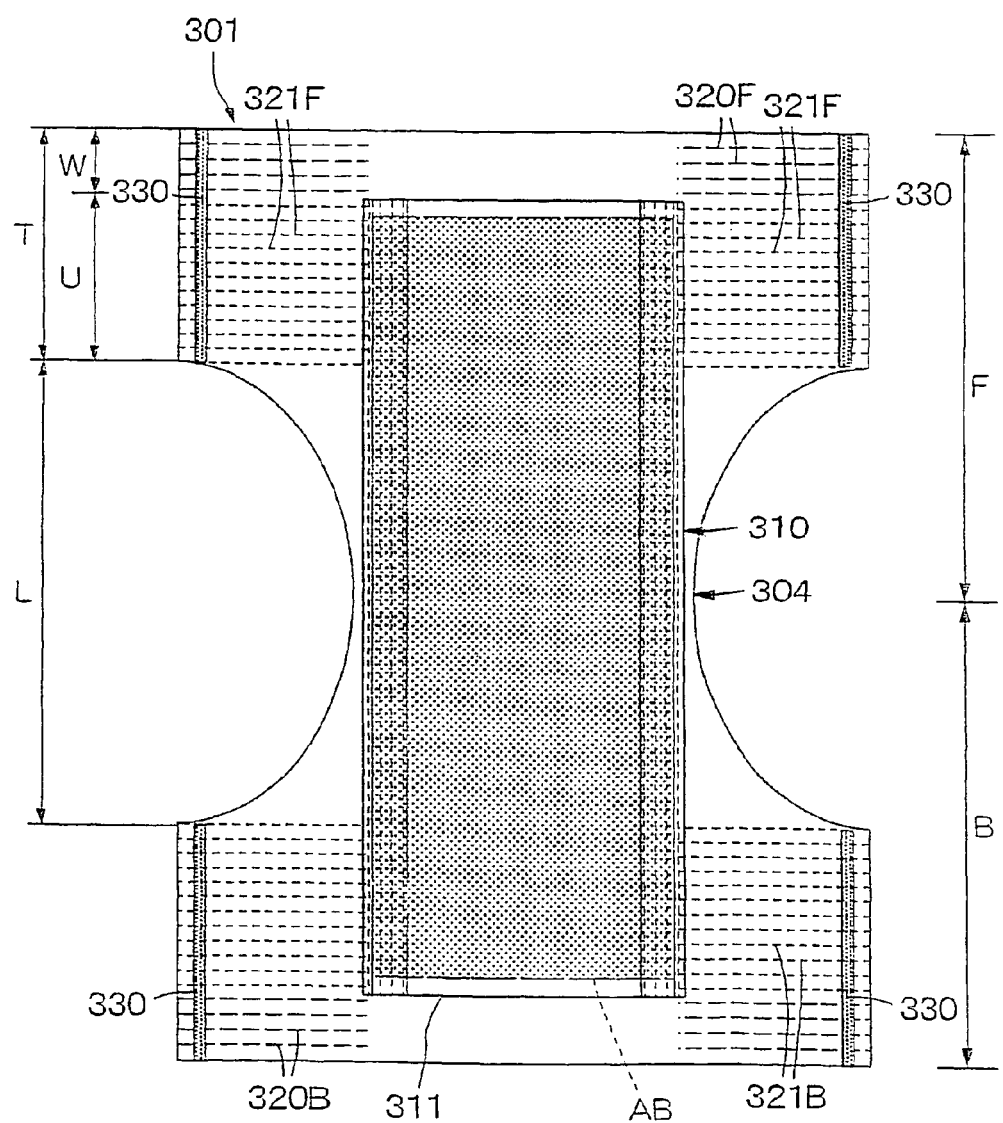
FIG. 17 is a plan view as viewed from the use surface for the developed state of the shorts-type diaper showing a third embodiment according to the present invention.
Figure 18:
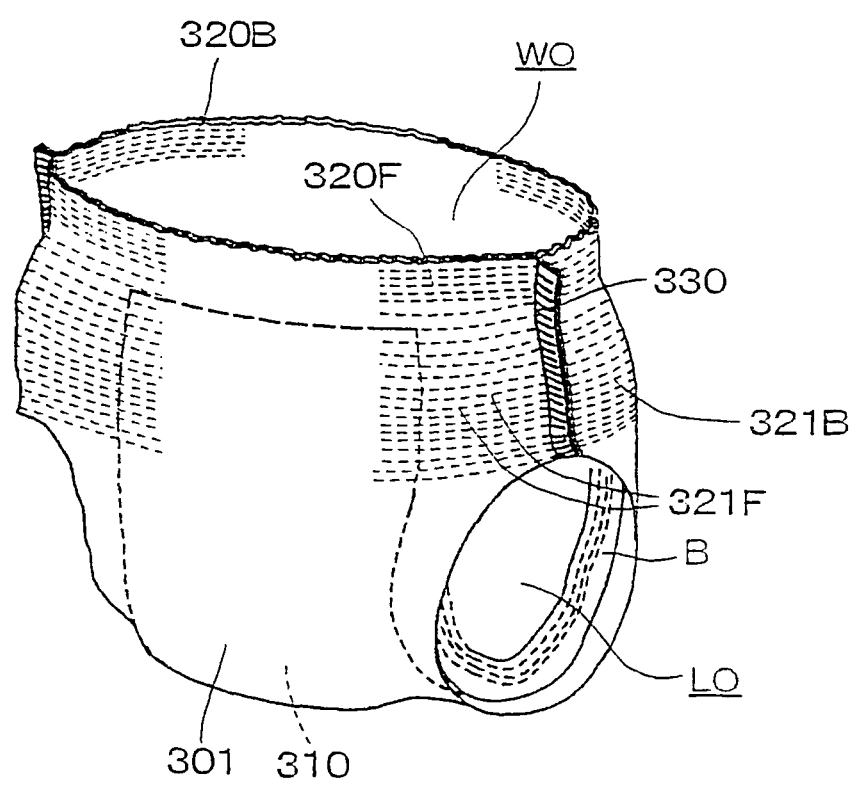
FIG. 18 is a major portion perspective view of the shorts-type diaper showing the third embodiment according to the present invention.

FIG. 17 shows a shorts-type disposable diaper in a third embodiment according to the present invention. As the different points of this embodiment from the first embodiment, it shows the same developed state as in FIG. 11, having a structure such that the crotch portion L is not provided with the crotch portion elastic member 123, and in addition, the waist elastic members 320F and 320B are not provided at the center but are provided in the sides only. The use state is shown in FIG. 18.

Fourth Embodiment

Figure 19:
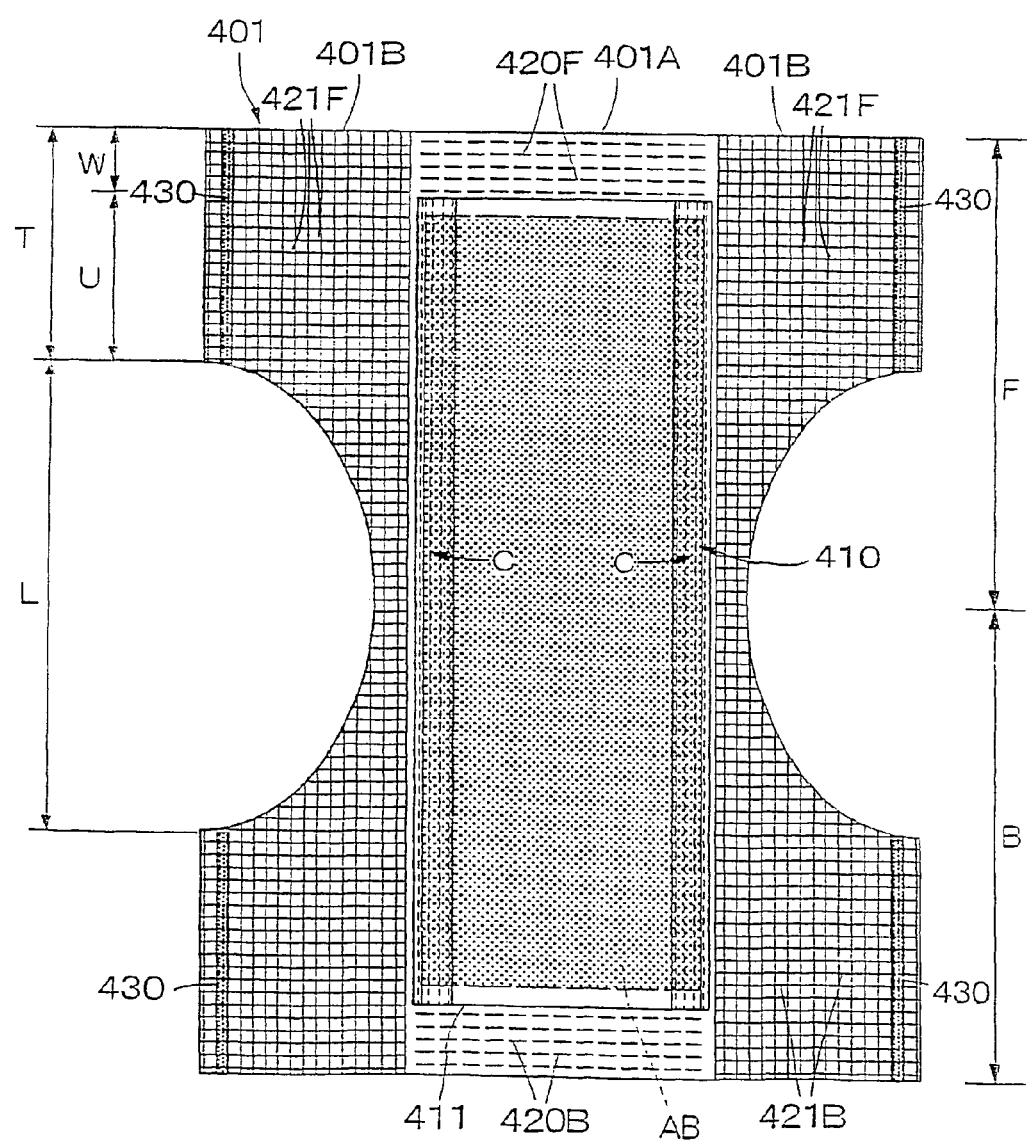
FIG. 19 is a plan view as viewed from the use surface for the developed state of the shorts-type diaper showing a fourth embodiment according to the present invention.

FIG. 19 shows a shorts-type disposable diaper in a fourth embodiment according to the present invention. In this embodiment, the external sheet 401 comprises a width direction central sheet 401A and side sheets 401B and 401B on both sides, and each side sheet 401B and 401B where for example, rubber threads are fixed in place in meshes for example, in grids between the non-woven fabrics are used. Then, the side sheets 401B and 401B on both sides are bonded to the width direction central sheet 401A and each side sheet 401B and 401B is allowed to expand and contract in the peripheral direction and forward and backward direction. In this case, a rubber thread in the peripheral direction forms an elastic members of the waist portion W and the under waist portion U.

(Supplementary Descriptions and Other Embodiments on Various Forms of Shorts-Type Disposable Diapers)

If the first to fourth embodiments are conceptually summarized, each is as shown in FIGS. 20A to 20D. In order to make it possible to infer by comparing these, one form that the waist elastic members 120F to 420F and 120B to 420B and the under waist portion elastic members 121F to 421F and 121B to 421B are disposed and fixed continuously in the peripheral direction so as to traverse the absorbers 110 to 410, and another form that the members are not provided at the center where the absorbent body AB is located and are disposed and fixed in place in only the right and left sides of the product can be selectively adopted.

In addition, it is also possible to select whether or not the crotch portion elastic members 123 to 423 be disposed. Further, the different disposition forms of the elastic member can be also adopted between the front side F and the back side B. Therefore, as shown as another embodiment in FIG. 20E, the form that the waist elastic members 20F and 20B and the under waist portion elastic members 21F and 21B are not provided at the center where the absorbent body AB is located and are disposed and fixed in place in only the right and left sides of the product, and further, the crotch portion elastic member 23 is not provided, or as shown as another embodiment in FIG. 20F, a form that the waist elastic members 20F and 20B and the under waist portion elastic members 21F and 21B are not provided at the center where the absorbent body AB is located and are disposed and fixed in place in only the right and left sides of the product and the crotch portion elastic member 23 is further provided, or the like can be adopted. It is also added that the disposition form of the elastic members is adopted appropriately. If the under waist portion elastic members 21F and 21B or the crotch portion elastic member 23 are not provided at the center where the absorbent body AB is located and are disposed and fixed in place in only the right and left sides of the product, it includes one case that the end portions of the under waist portion elastic members 21F and 21B or the end portions of the crotch portion elastic member 23 is overlapped on the side edge portion of the absorbent body AB, and another case that they do not reach the side edge portion of the absorbent body AB and are spaced out from the latter.

Particularly, in the present invention, it is desirable that the elastic member is not provided inwardly from the portion corresponding to the vicinity of the side edge of the absorbent body, for example, the portion within 10 mm, particularly within 5 mm, from the side edge. Thereby, the absorbent body is hardly contracted and is kept in a thin state as it stands.

In addition, although for the above examples, rectangular absorbers 110 to 410 are bonded to almost sandglass-shaped external sheets 101 to 410, a form may be such that the liquid-permeable top sheets 111 to 411 having the same shape as the external sheets 101 to 410 are provided and the absorbent body AB is provided therebetween. Further, a form may be such that the external sheets 101 to 401 and the absorbers 110 to 410 are in a borderless state and are integrated.

Although the sheet comprising the external surface of the product is the one that air permeable/water repellent non-woven fabrics of two or three sheets or more are laminated and fixed in the above examples, the sheet may be one sheet of non-woven fabric and in this case, the elastic members 121 to 421 can be bonded to the use surface side of the non-woven fabric. Further, a plastic sheet can be interposed at the intermediate portion between the laminated non-woven fabrics or can be stuck to the use surface side on the back side of the non-woven fabric.

The under waist portion elastic members 121F to 421F or 121B to 421B may be also disposed in a grid form. This one example is a form as shown in FIG. 19. It is desirable that the elastic member has the above thickness and distance even in this form.

Further, it is desirable that the waist elastic members 120F to 421F and the under waist portion elastic members 121F to 421F of the front side F have the above thickness and distance as long as the members exist in the length range of not less than 60%, preferably not less than 70%, more preferably not less than 90% of the body peripheral region T in the length range from the waist opening edge to the leg opening start end. Therefore, in the maximum 40% area, if the under waist portion elastic members 121F to 421F do not have the above thickness or the distance, a feeling of neatness is not damaged as a whole.

On the other hand, designs such as characters can be arranged, for example, by printing on the back side of the non-liquid permeable back sheet 112 - - - at the center of the product (the almost entire area of the absorbent body AB) as shown in FIG. 21A and FIG. 21B. This design may not be broken and can be clearly identified by allowing the design portion to be located at a position corresponding to the absorbent body AB having a certain rigidity, or the like. Then, particularly as illustrated, if the front side and the back side of this character is arranged according to the front side and the back side of the product, everyone can identify the front side and the back side of the product at a glance and can enjoy changing diapers, and a wearer is pleased to wear the product accordingly. When performing this design on the product, a design sheet on which the design is arranged may be interposed between the external sheets. In addition, a design can be also printed on the external sheet 101, - - - .

Meanwhile, the external sheet 1 can be provided with an elastic member in various forms to allow the crotch portion or the under crotch portion to fit a human body.

Fifth Embodiment

Figure 22:
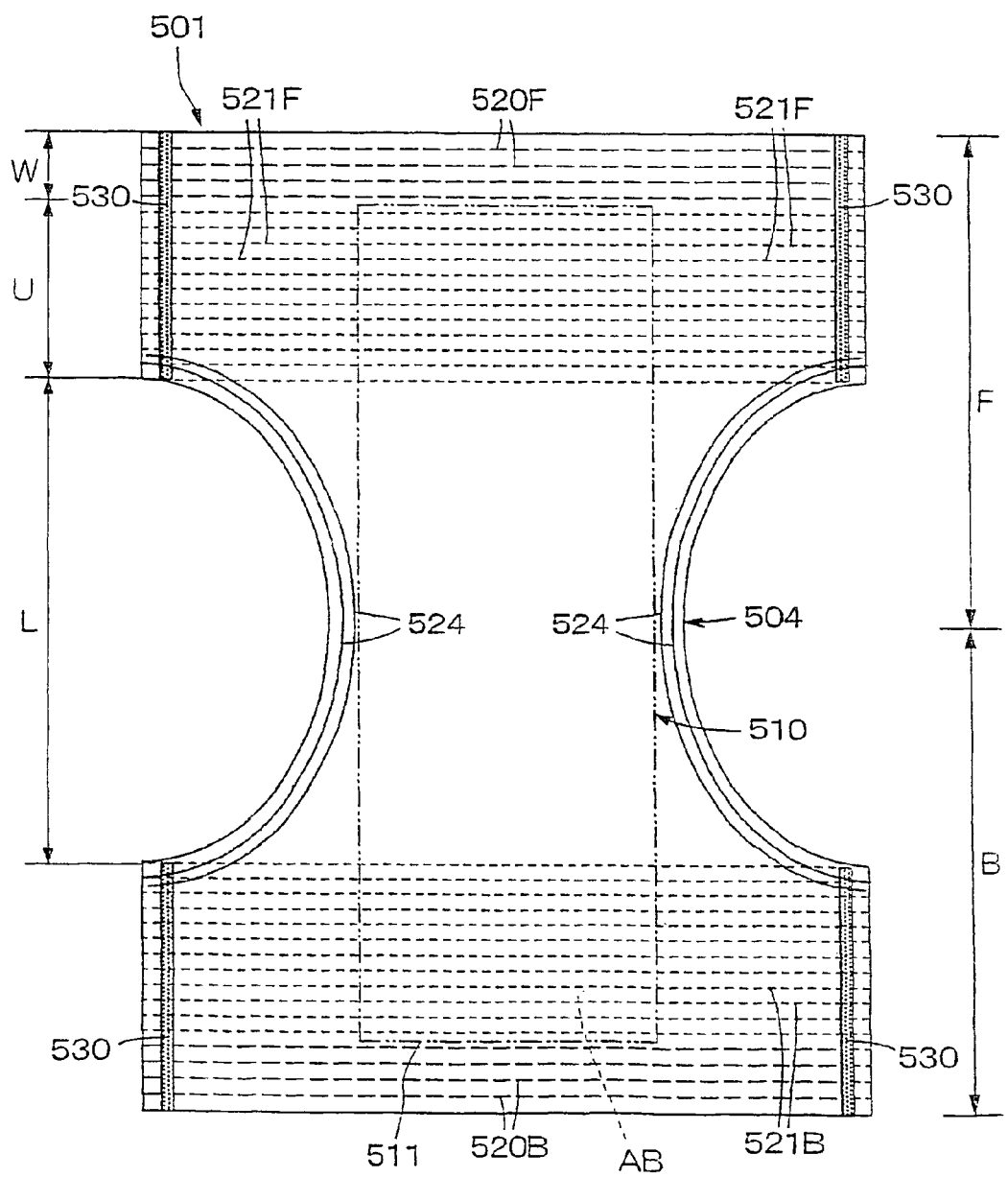
FIG. 22 is a plan view as viewed from the use surface for the developed state of the shorts-type diaper showing a fifth embodiment according to the present invention.

FIG. 22 shows a shorts-type disposable diaper in a fifth embodiment according to the present invention. In this embodiment, each crotch portion elastic member 524 and 524 is fixed in place between the non-woven fabrics of the external sheet 501, running almost parallel with the leg opening edges of the crotch portion L from the end portion of the front waist portion to the end portion of the back waist portion. In this embodiment, the crotch portion elastic member 524 contracts the leg opening portion LO to prevent the flow of a body fluid. In addition, the absorber 510 is shown in a virtual line to expressly show the crotch portion elastic members 524 and 524.

Sixth Embodiment

Figure 23:
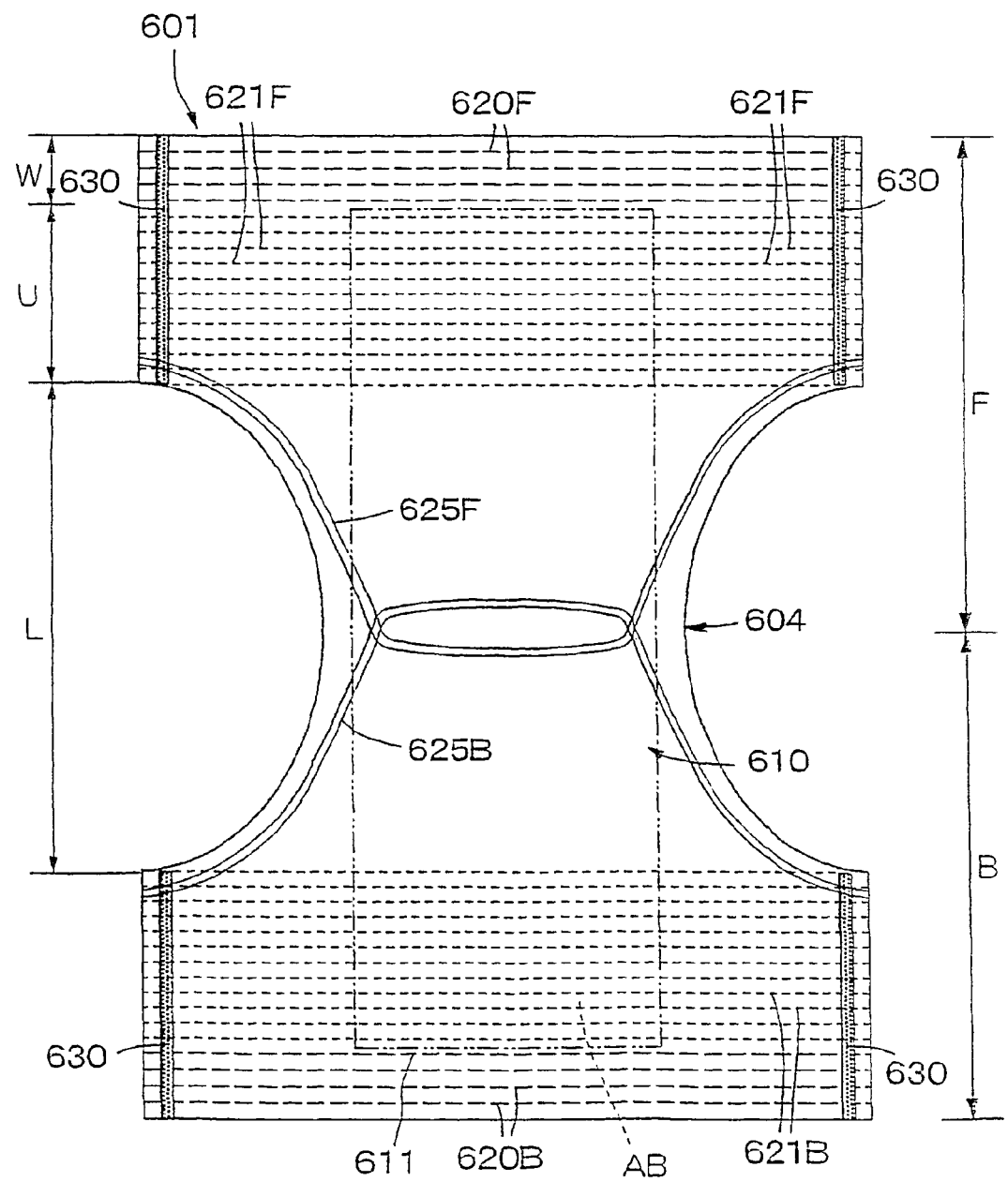
FIG. 23 is a plan view as viewed from the use surface for the developed state of the shorts-type diaper showing a sixth embodiment according to the present invention.

FIG. 23 shows a shorts-type disposable diaper in a sixth embodiment according to the present invention. In this embodiment, the crotch portion/under crotch portion elastic members 625F and 625B are each fixed in place between the non-woven fabrics of the external sheet 601, so as to allow them to traverse the under crotch portion from the end portion of the left side to the end portion of the right side in the front side F and the back side B. In addition, in this example, a form is so constituted that the crotch portion/under crotch portion elastic members 625F and 625B on the front side F and the back side B partially intersect with each other.

Seventh Embodiment

Figure 24:
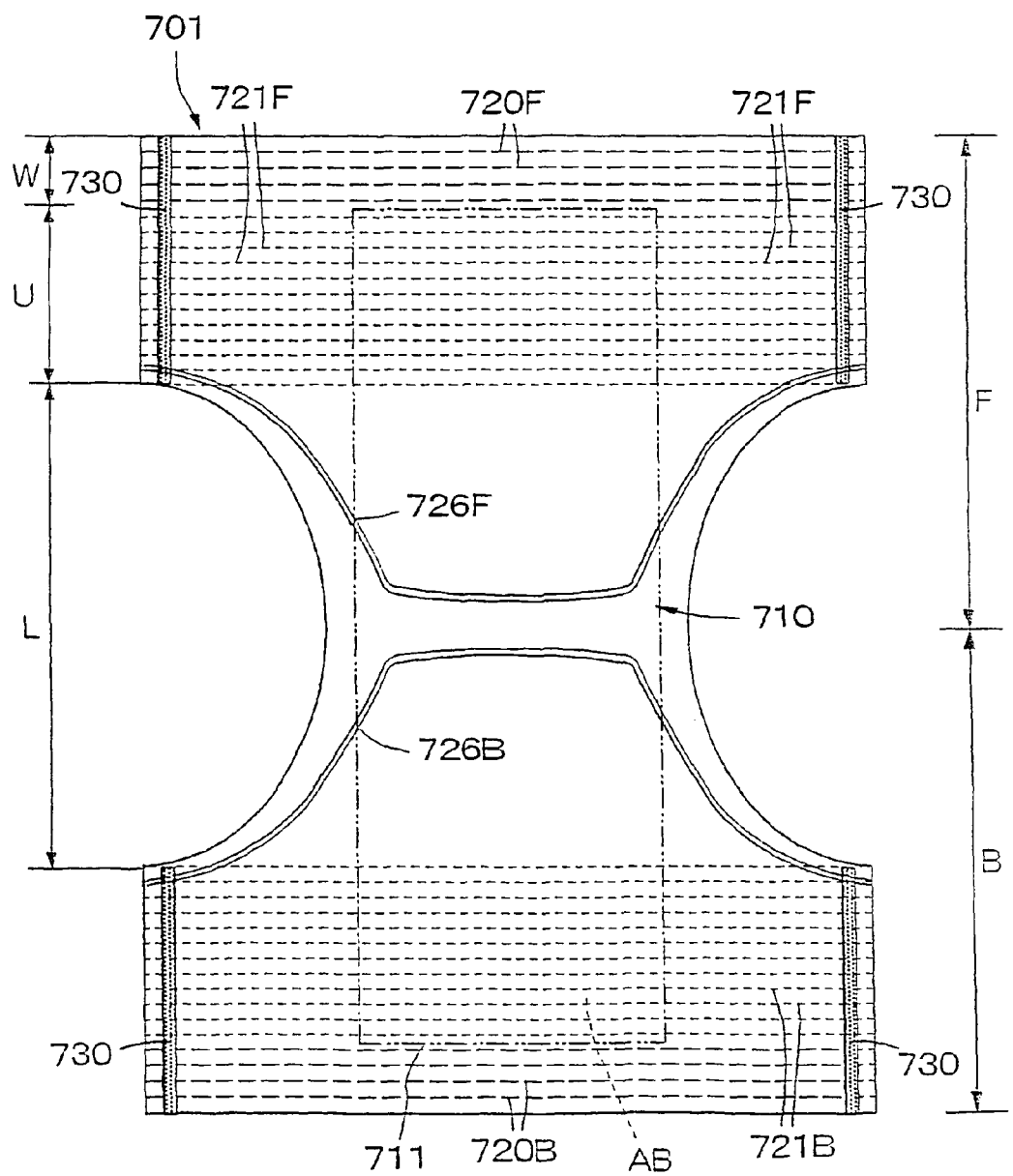
FIG. 24 is a plan view as viewed from the use surface for the developed state of the shorts-type diaper showing a seventh embodiment according to the present invention.

FIG. 24 shows a shorts-type disposable diaper in a seventh embodiment according to the present invention. In this embodiment, the crotch portion/under crotch portion elastic members 726F and 726B are each fixed in place between the non-woven fabrics of the external sheet 701, so as to allow them to traverse the under crotch portion from the end portion of the left side to the end portion of the right side in the front side F and the back side B. In this example, a form is so constituted that the crotch portion/under crotch portion elastic members 726F and 726B do not intersect with each other and are in parallel with each other in the crotch portion.

Eighth Embodiment

Figure 25:
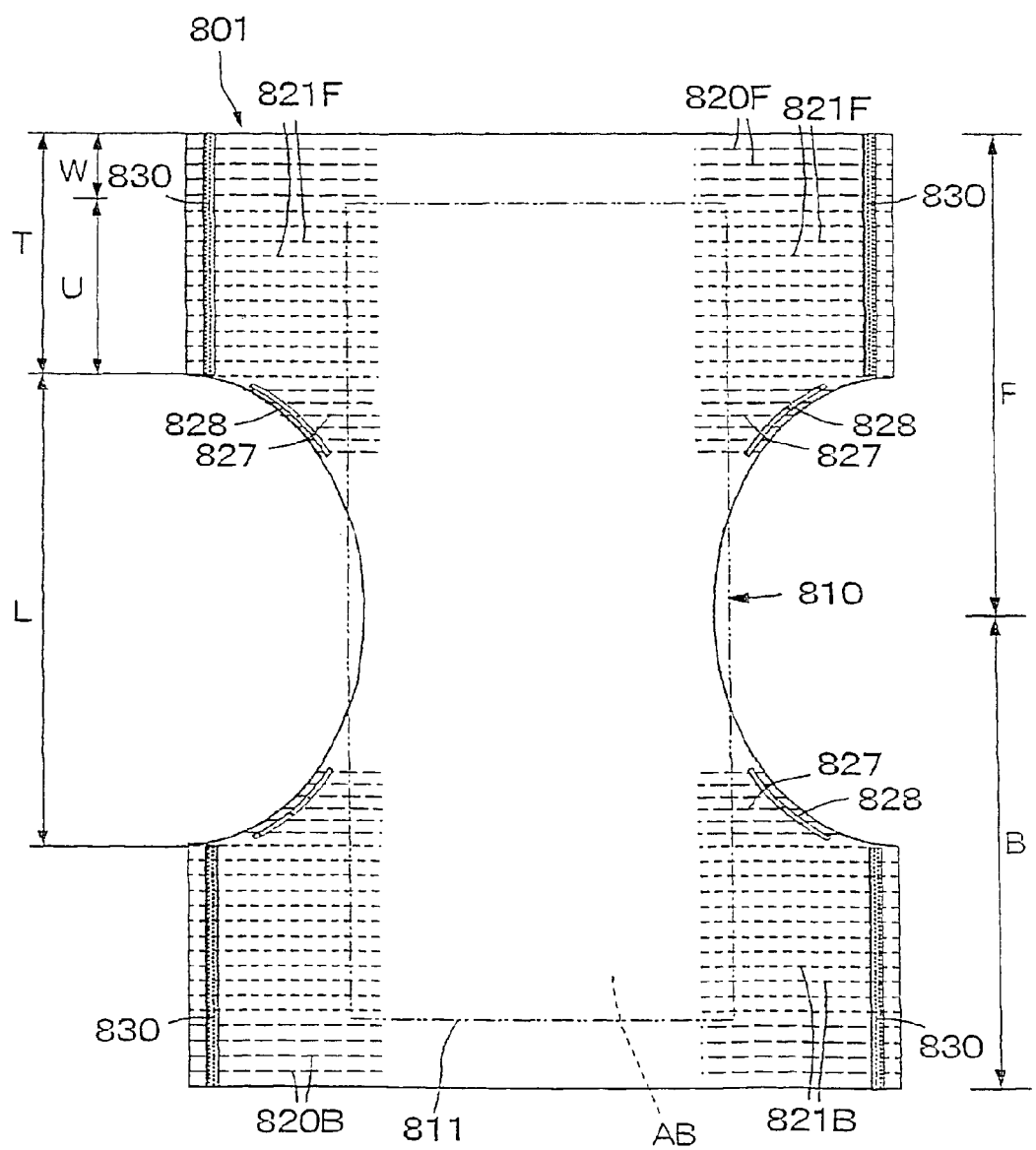
FIG. 25 is a plan view as viewed from the use surface for the developed state of the shorts-type diaper showing an eighth embodiment according to the present invention provided with a fairing elastic member.

FIG. 25 shows a shorts-type disposable diaper in a eighth embodiment according to the present invention. In this embodiment, the width of the external sheet 801 can be narrower than that of the absorber 810, particularly that of the absorbent body AB in the crotch portion. In this embodiment in FIG. 25 or the afore-mentioned embodiment, the external sheet 801 which protrudes outside from the side edge of the absorbent body AB is likely to flutter and this is a problem in order to obtain the neatness of the entire product. Then, a feeling of fluttering can be eliminated by providing a fairing elastic member 827 between the non-woven fabrics of the external sheet 801 on both sides of the crotch portion L to attract a protruding external sheet 801 to the central side as in the crotch elastic member 123 in the first embodiment. In this case, the drawing-in of the external end portions of a group of the fairing elastic members 827 to the central side can be prevented by fixing in place the external end portions of the group of the fairing elastic members 827 at a sealing line 828 with a hot melt adhesive.

Ninth Embodiment

Figure 26:
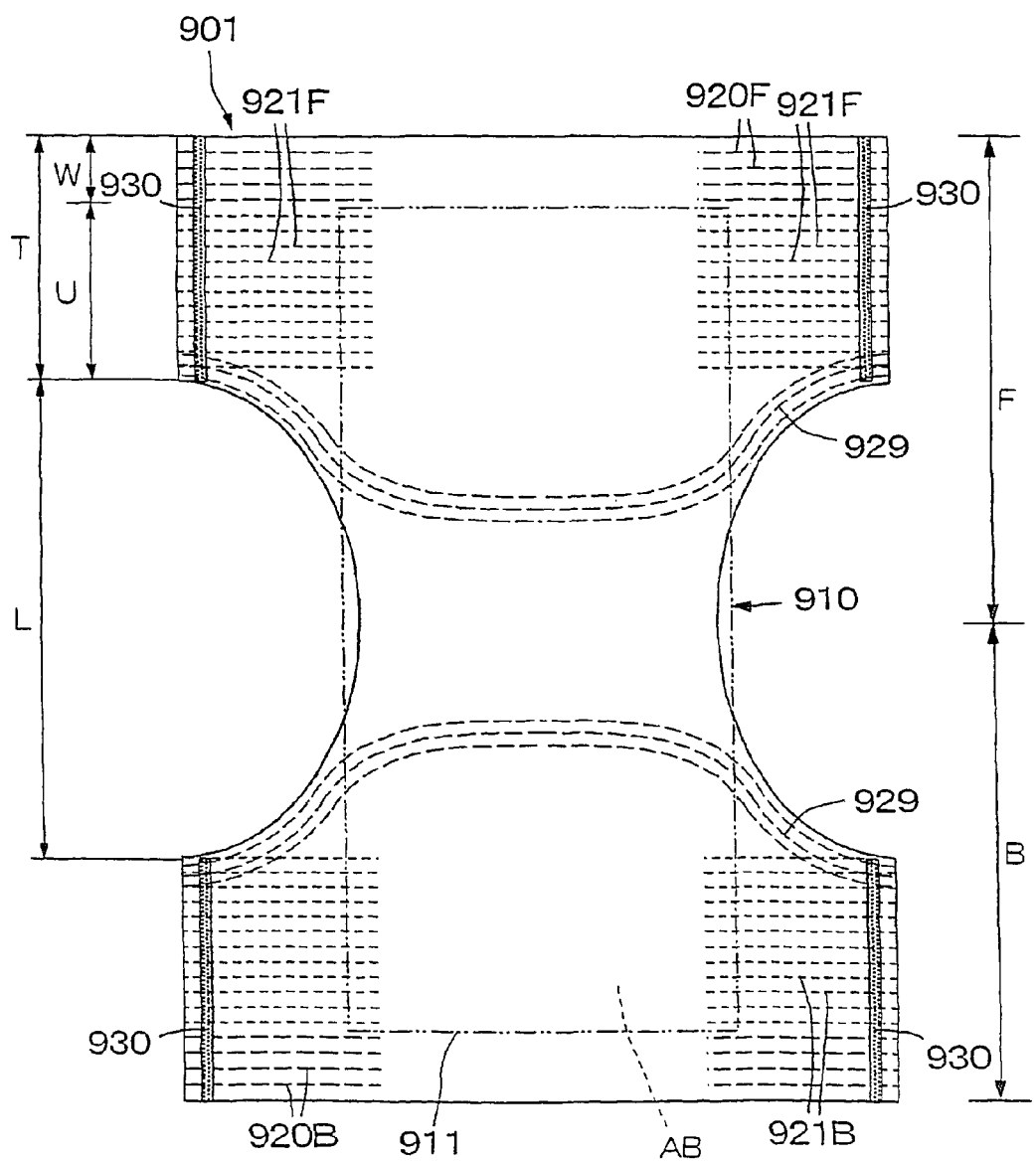
FIG. 26 is a plan view as viewed from the use surface for the developed state of the shorts-type diaper showing a ninth embodiment according to the present invention provided with a fairing elastic member.

FIG. 26 shows a shorts-type disposable diaper in a ninth embodiment according to the present invention. In order to eliminate a feeling of fluttering similarly, the embodiment is so constituted that the fairing elastic members 929 and 929 are each fixed in place between the non-woven fabrics of the external sheet 901 over the end portion of the right side, so as to'allow them to traverse the crotch portion from the end portion of the left side in the front side F and the back side B. In this embodiment, a feeling of fluttering can be eliminated by allowing the portion in the peripheral direction at the intermediate point on the fairing elastic member 929 to attract the external sheet 901 which protrudes outside from the side edge of the absorbent body AB to the central side and since the end portion of the fairing elastic member 929 is connected with the end portion of the side, the fairing elastic member 929 acts to upraise the crotch portion to the body peripheral region T side to eliminate the relaxation of the belly portion and the hip portion, thereby resulting in a neater product.

Tenth Embodiment

Figure 27:
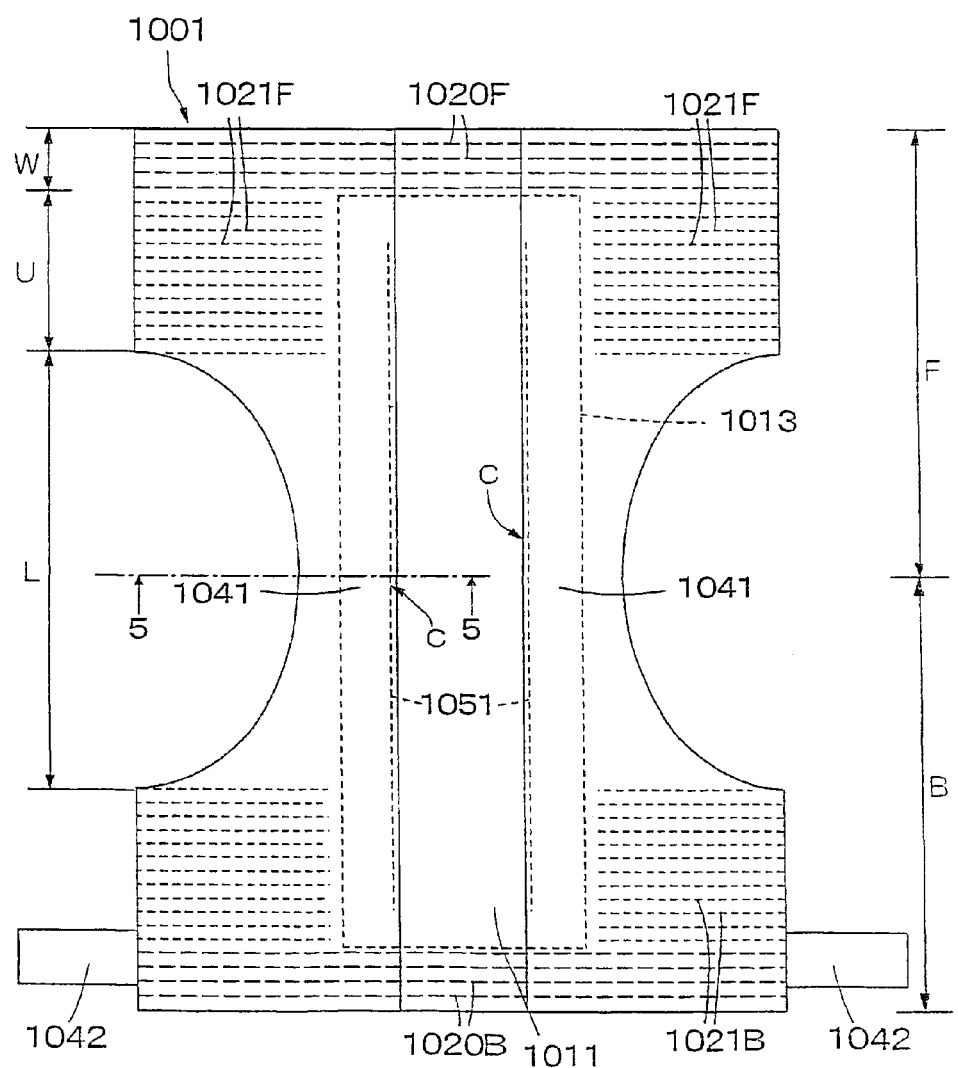
FIG. 27 is a plan view as viewed from the use surface for the developed state of a tape-type disposable diaper showing a tenth embodiment according to the present invention.
Figure 28:
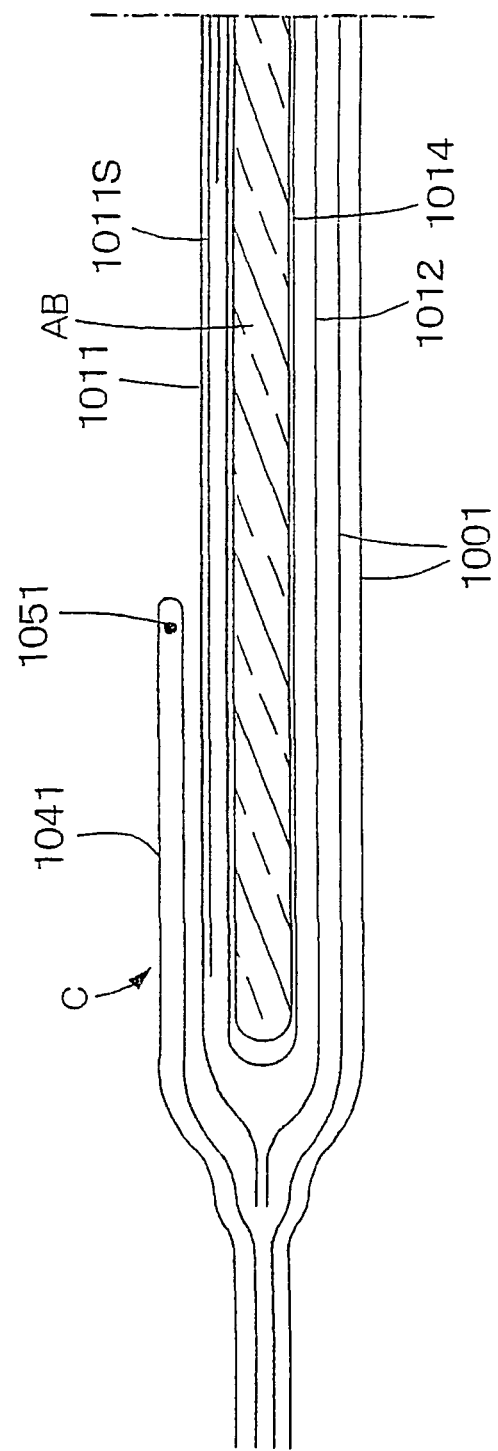
FIG. 28 is a longitudinal cross sectional view by and equivalent position of the 5-5 arrowed line of FIG. 27.

FIG. 27 and FIG. 28 show a shorts-type disposable diaper in a tenth embodiment according to the present invention. As described above, the present invention is applied to a tape-type diaper besides a shorts-type disposable diaper. In this example, the diaper comprises the rising sheets 1041 and 1041, and the elastic members 1051 and 1051 are provided at the tip of these free rising portions, which constitute the rising cuffs C and C. The rising sheet 1041 is bonded to the back sheet 1001 which is the same as the external sheet. The numeral 1042 is a tape fastener for taking both side portions on the backs side to the both right and left side portions on the belly portion and bonding them. In this example, the waist elastic members 1020F and 1020B comprising a thin rubber thread in parallel with the end edge of the waist opening portion WO and spaced out are disposed and fixed in place between the non-woven fabrics of the external sheet 1001 in the waist portion W, in the longitudinal end of the front side F and the back side B in an extended state so as to allow them to be extended and contracted, in order to increase the fitness around waist. The under waist portion elastic members 1021F and 1021B are further provided along the peripheral direction on the sides excluding the center, on the hip portion of the front side F and the back side B.

Eleventh Embodiment

Figure 29:
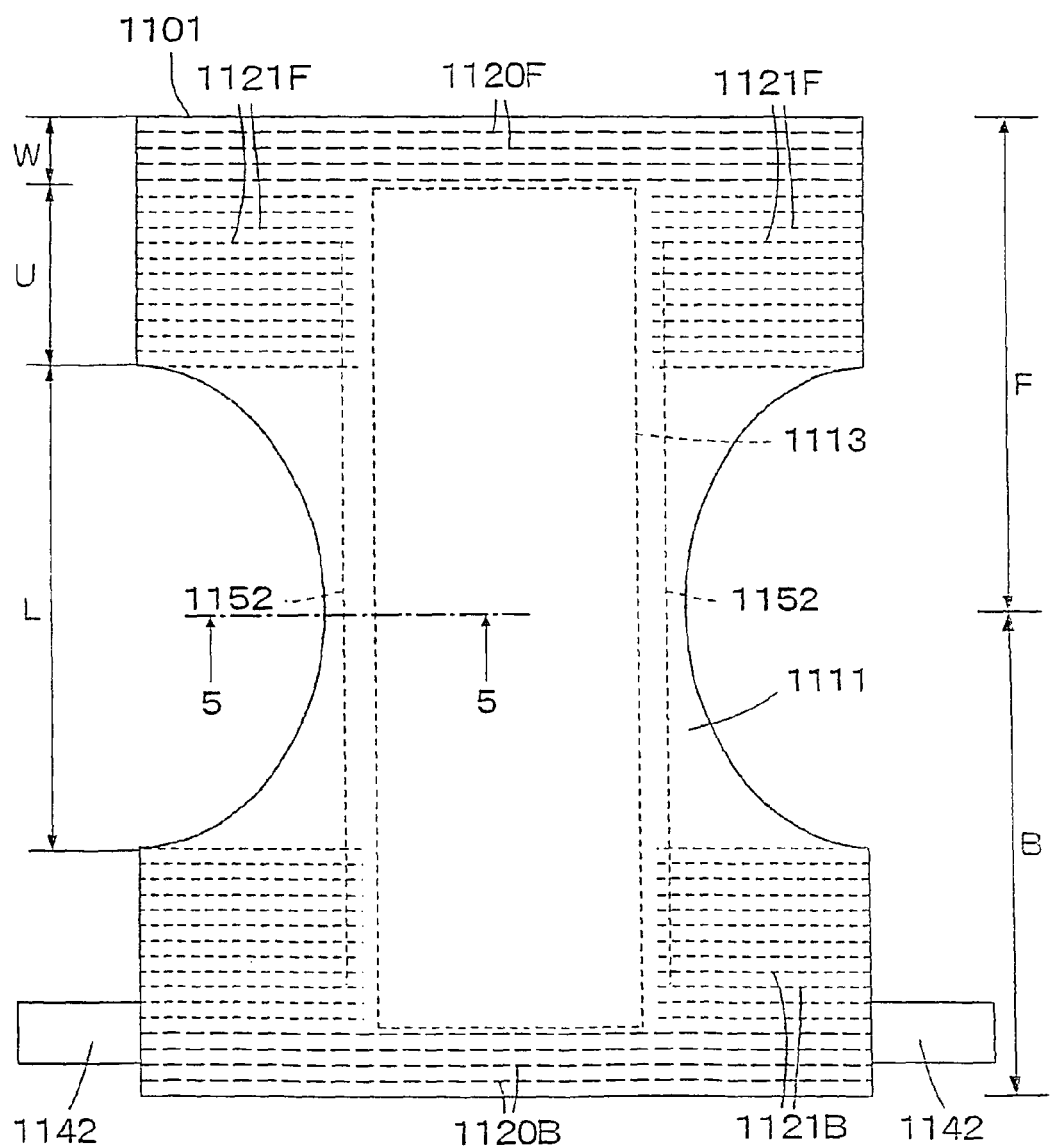
FIG. 29 is a plan view as viewed from the use surface for the developed state of a tape-type disposable diaper showing an eleventh embodiment according to the present invention.
Figure 30:
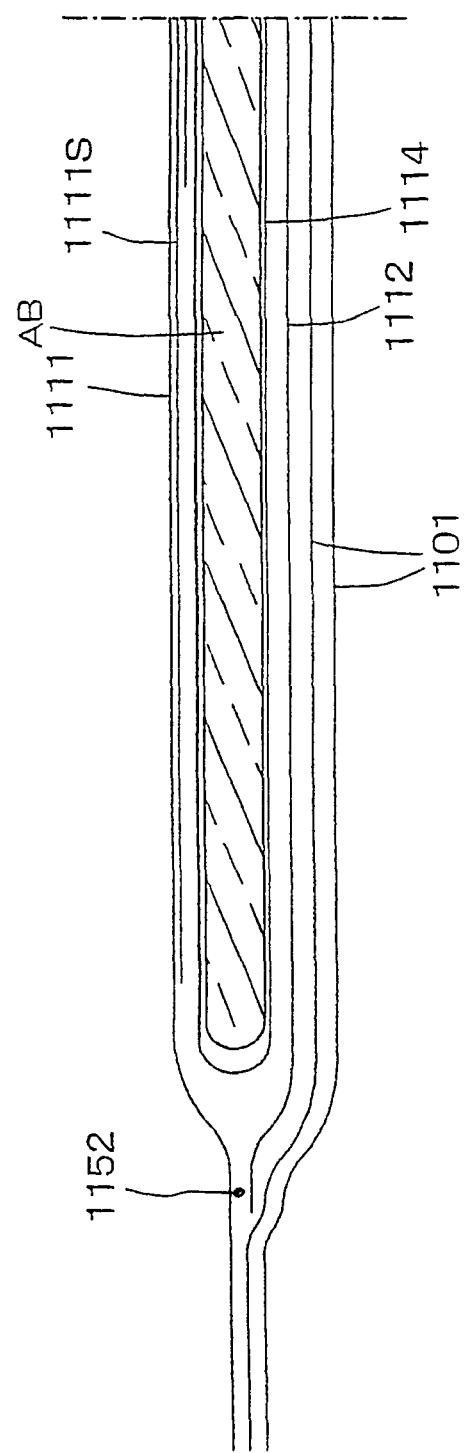
FIG. 30 is a longitudinal cross sectional view by an equivalent position of the 5-5 arrowed line of FIG. 29.

FIG. 29 and FIG. 30 show a tape-type diaper in a eleventh embodiment according to the present invention. This is an example having no rising cuffs. Then, the elastic members 1152 and 1152 are fixed in place between the liquid-permeable top sheet 1111 and the back sheet 1112, along the longitudinal direction on the flap portion outside the absorbent body AB. In this example, the waist elastic members 1120F and 1120B and the under waist portion elastic members 1121F and 1121B are also provided.

(Regarding Elastic Members)

Figure 31:
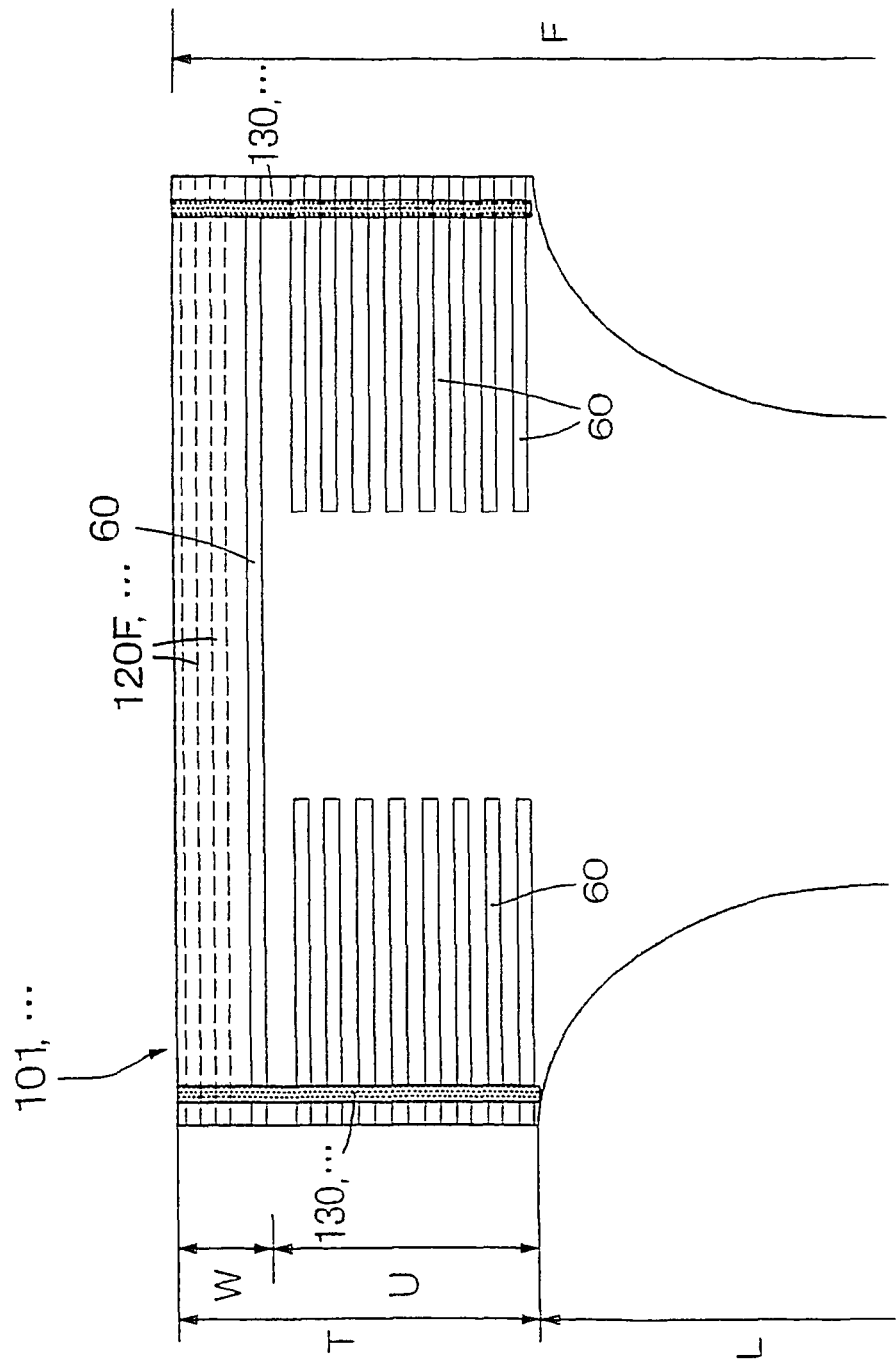
FIG. 31 is a plan view as viewed from the use surface for the developed state of an embodiment provided with another elastic member.

As the above-described elastic members, resilient/elastic materials such as urethane or the like can be used besides materials such as natural rubber, synthetic rubber and the like. In addition, a thin strip-shaped resilient/elastic band and a sheet-like one with a big area can be also used. Taken up as these examples are bands, films, sheets and the like, of urethane or the like. Imperforate film and perforate film as films, further, mesh sheets as sheets can be suitably selected. The disposition example of an imperforate film 60 is shown in FIG. 31. In addition, the disposition example of a mesh sheet 61 is shown in FIG. 32. Even in these forms, it is important that the proportion of an area on which the elastic member is mounted on the external sheet 101, - - - of the product is not less than 60% of the length range of the body peripheral region.

(Regarding Widths of Various Portions of Preferable Product)

It is preferable that in the disposable diaper to which a press thinned-type absorbent body according to the present invention, the width d2 of the absorbent body to the waist width d1 is not more than 40%.

Figure 33B:
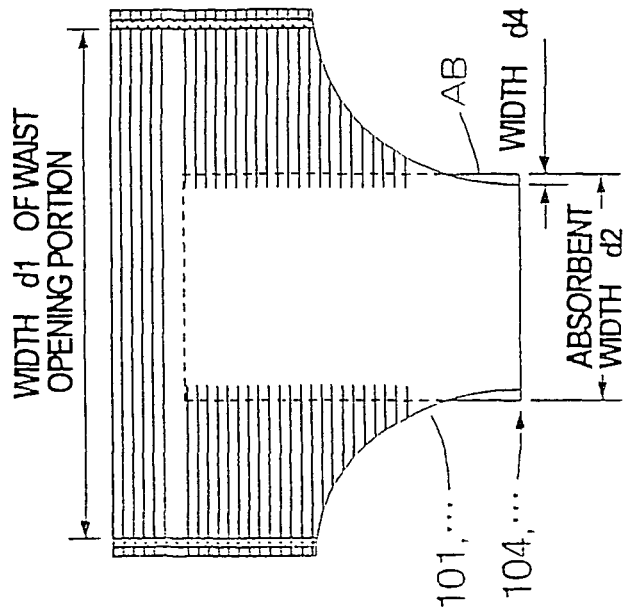
FIG. 33A and FIG. 33B are front views for the use state of a disposable diaper showing a preferred example of a crotch width.
Figure 33A:
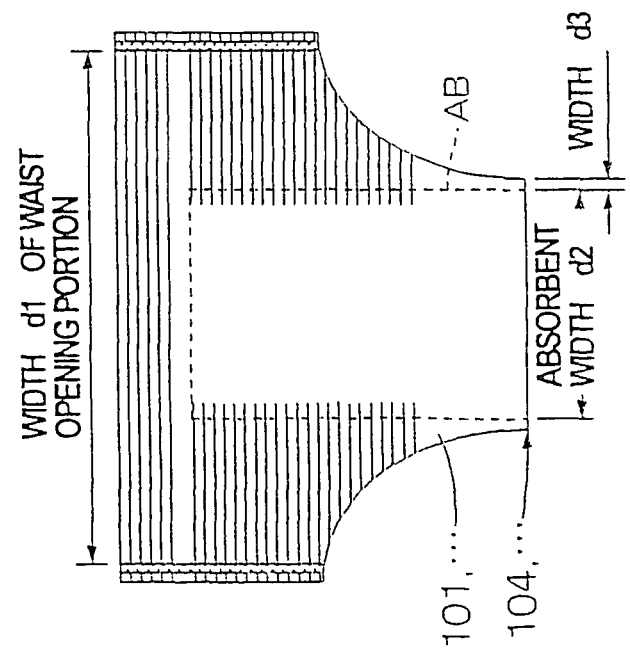

Further, it is desirable that in such a disposable diaper, the side ends of the external sheets 101 to 1101 are formed so as to allow the sheets to be located within 5 mm from the side end of the absorbent body AB in the crotch portion. This includes one case as shown in FIG. 33A that the crotch portion side end of the external sheet 101, - - - protrudes outside the crotch portion side end of the absorbent body AB and the protrusion width d3 is made to be not more than 5 mm, and another case as shown in FIG. 33B that the crotch portion side end of the external sheet 101, - - - enters the inside of the crotch portion side end of the absorbent body AB and the crotch portion side end of the absorbent body AB protrudes from the crotch portion side end of the external sheet 101, - - - , and the protrusion width d4 is made to be not more than 5 mm. In addition, although not illustrated, a case that the crotch portion side end of the external sheet 101, - - - and the crotch portion side end of the absorbent body AB are overlapped upon each other is also included.

In the disposable diaper to which a press thinned-type absorbent body according to the present invention is applied, although the voluminous feeling and swollen feeling of a diaper (particularly, of the crotch portion) are reduced by merely thinning the absorbent body to achieve a very neatness in the appearance of the product, further as described above, the external sheet scarcely protrudes from the sides of the absorbent body by forming the crotch portion side end of the external sheet so as to be located within 5 mm from the crotch portion side end of the absorbent body, the voluminous feeling and swollen feeling of the crotch portion are further reduced, and thereby, resulting in a more neatness in the appearance of the product.

Examples

Various super absorbent polymers were prepared and the following tests were performed:

(Absorption Test Under Pressure)

Figure 34:
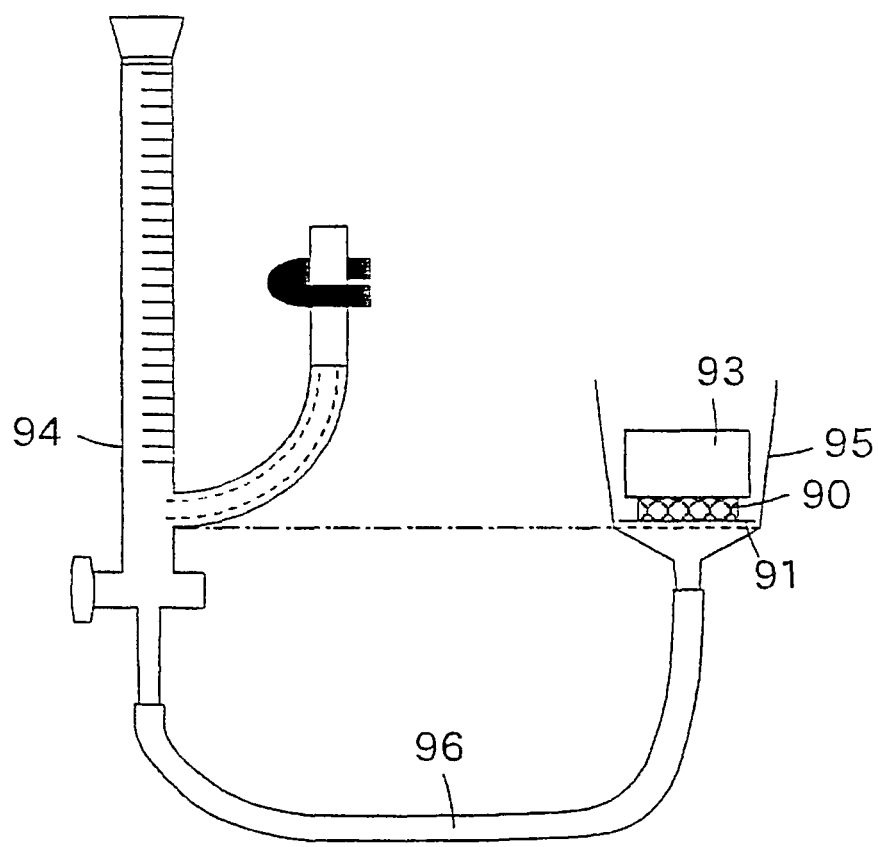
FIG. 34 is a manual view of an absorption test under pressure.

The outline of this test is shown in FIG. 34. That is:

1) A sample 90 of SAP of 0.2 g is weighed, and the sample is evenly diffused in a circle with diameter of 40 mm on a filter paper 91 with diameter of 50 mm.

2) A load of 20 g/cm$^2$ is loaded on the sample by using a spindle 92. In this case, the four sides of a spindle 93 are connected with the filter paper 91 and fixed in place by using a cellophane tape with width of 1.5 mm.

3) A measurement device in which the exhaust opening of a bullet 94 and the lower opening of a funnel 95 are connected with a tube 96 is prepared, and the sample 90 is calmly placed in the funnel 95 by using the filter paper 91 as lower side, in a state that the sample 90 is sandwiched between the spindle 92 and the filter paper 91. Then, an absorption amount is measured for 60 minutes.

4) On the other hand, the absorption amount of the filter paper is measured in the same manner as a blank.

5) The absorption amount after 60 minutes is converted into 1.0 g so as to be an absorption amount under pressure.

(Absorption Test Under Normal Pressure)

1) A sample of 0.3 g is charged into a nylon tea bag (a bag) and the tea bag is dipped in a physiological saline (0.9% NaCl aqueous solution).

2) After 10 minutes, the tea bag is completely taken out of the physiological saline, and is kept in a state of being lifted for 10 minutes to drain the tea bag.

3) After the draining, the weight is measured, and a value that the weight of the tea bag is deducted from this is determined to be an absorption amount under normal pressure.

(Measurement Test of Water Retention Amount)

1) A sample of 0.5 g is charged into a nylon tea bag.

2) The tea bag is dipped in a 0.9% physiological saline and after the tea bag is swollen for 30 minutes, a centrifugal dehydration is performed on the tea bag at 15,000 rpm for 3 minutes.

3) The weight of the tea bag is deducted from the weight after the dehydration, and a value that the deducted weight is divided by the weight of the sample is determined to be a water retention amount.

(Absorption Rate Test)

A sample of 1 g is evenly diffused on a dish with diameter of 90 mm and artificial urine of 30 cc is charged thereinto. Then, a time to absorb all of the urine is measured and is determined to be an absorption rate.

(Gel Permeability Rate Test)

1) A sample of 1.0 g is charged into artificial urine of 200 cc and the solution is left as it stands for one hour to allow the solution to reach a saturated state.

2) The solution in item 1) is charged into a bullet with diameter of 36 mm, and is subject to still standing for 30 minutes.

3) The cock of the bullet is turned and each time that 50 cc and 100 cc of the artificial urine are passed is measured and is determined to be a gel permeability rate.

(Measurement Test of Granularity Distribution)

A sample of 10 g is sieved with each sieve of 500, 300, 250, 212, 180, 150, 106 and 75 μm, the weights of the samples left on each sieve are measured, and each percentage is indicated, taking losses caused by clogging into consideration. In addition, when the sample is sieved, eight sieves are not used for one time, but four sieves are superimposed at a time, and operation is performed in two separate steps in such a manner that the first step is for 500 to 212 μnm, and the second step is for 180 to 75 μm. In addition, sieving time is for one minute.

(Gel Elastic Modulus Test)

1) A sample of 2.0 g is charged into a 50 ml beaker, and a physiological saline of 50 ml is added thereto to prepare a twentyfivefold swollen gel.

2) The gel elastic modulus of the swollen gel is measured with a card meter. In addition, the measuring conditions of the card meter are as follows:

Conditions of card meter: spring weight 200g

Pressure shaft diameter of 8 mm

Movable axial plate elevating speed 0.4 mm/sec.

TABLE 1

| | | EXAMPLE 1 | EXAMPLE 2 | EXAMPLE 3 | EXAMPLE 4 | EXAMPLE 5 |
|---|---|---|---|---|---|---|
| ABSORPTION AMOUNT UNDER PRESSURE (cc/g) | | 35.0 | 34.5 | 33.3 | 34.9 | 32.5 |
| ABSORPTION AMOUNT UNDER NORMAL PRESSURE (cc/g) | | 65.0 | 61.2 | 66.4 | 65.3 | 61.1 |
| ABSORPTION RATE (sec.) | | 55.0 | 61.7 | 48.7 | 55.3 | 65.0 |
| GEL PERMEABILITY RATE | 50 cc | 54 | 74 | 102 | 66 | 42 |
| (sec.) | 100 cc | 188 | 211 | 275 | 183 | 126 |
| GEL ELASTIC MODULUS (N/m$^2$) | | 3700 | 3000 | 2800 | 2500 | 3200 |
| PARTICLE SIZE | ~500 μm | 23.2 | 10.3 | 26.7 | 21.4 | 6.6 |
| DISTRIBUTION | 500~250 μm | 72.6 | 65.3 | 68.3 | 75.9 | 78.8 |
| (%) | 250~180 μm | 3.4 | 18.6 | 4.5 | 2.2 | 11.5 |
| | 180~ μm | 0.8 | 5.8 | 0.5 | 0.5 | 3.1 |
| WEIGHT RATIO OF SAP (wt %) | | 52.5 | 80.0 | 62.5 | 55.0 | 67.5 |
| DENSITY (kg/m$^3$) | | 400 | 417 | 306 | 286 | 409 |
| BASIS WEIGHT (gsm) | | 400 | 500 | 550 | 400 | 450 |
| THICKNESS (mm) | | 1.0 | 1.2 | 1.8 | 1.4 | 1.1 |

| | | EXAMPLE 6 | COMP. EXAMPLE 1 | COMP. EXAMPLE 2 | COMP. EXAMPLE 3 |
|---|---|---|---|---|---|
| ABSORPTION AMOUNT UNDER PRESSURE (cc/g) | | 35.0 | 29.0 | 32.2 | 27.5 |
| ABSORPTION AMOUNT UNDER NORMAL PRESSURE (cc/g) | | 69.8 | 47.0 | 59.8 | 48.2 |
| ABSORPTION RATE (sec.) | | 35.0 | 80.0 | 55.8 | 72.0 |
| GEL PERMEABILITY RATE | 50 cc | 88 | 340 | 122 | 89 |
| (sec.) | 100 cc | 302 | 711 | 351 | 151 |
| GEL ELASTIC MODULUS (N/m$^2$) | | 2100 | 2100 | 1700 | 2800 |
| PARTICLE SIZE | ~500 μm | 24.3 | 8.4 | 14.3 | 17.2 |
| DISTRIBUTION | 500~250 μm | 56.6 | 54.9 | 65.3 | 68.2 |
| (%) | 250~180 μm | 15.3 | 21.6 | 15.2 | 11.0 |
| | 180~ μm | 3.8 | 15.1 | 5.2 | 3.6 |
| WEIGHT RATIO OF SAP (wt %) | | 65.0 | 55.0 | 67.5 | 45.0 |
| DENSITY (kg/m$^3$) | | 367 | 333 | 300 | 278 |
| BASIS WEIGHT (gsm) | | 550 | 400 | 450 | 500 |
| THICKNESS (mm) | | 1.5 | 1.2 | 1.5 | 1.8 |

Next, various, absorbent bodies are manufactured from these super absorbent polymers and pulps according to the afore-mentioned air laying method. In addition, the absorbent bodies to which thinning by pressurization is omitted were also manufactured. These are shown in Table 1.

Moreover, the following tests, were performed on these manufactured absorbent bodies. Further, the test results are shown in Table 2.

(Absorbent Body Sheet Performance Measurement Test)
Measurement of Absorption Amount . . . No. 1:
1) An absorbent body cut by 100 mm×150 mm is wrapped with a non-woven fabric and the periphery is sealed to prepare a sample.
2) The sample is dipped in artificial urine for 30 minutes.
3) The sample is drained on a mesh for 30 minutes, and the weight A is measured.
4) The sample is further drained under a load of 20 g/cm$^2$ for 3 minutes, and the weight B is measured.
5) The absorbent body is taken out of the sample, and the weight C of the remaining non-woven fabric is measured. Then, an absorption amount A after absorbed at a normal pressure and dewatered under normal pressure and an absorption amount B after absorbed at a normal pressure and drained under a load are calculated in accordance with the following equations, respectively.

Absorption amount $A$ (cc/cm$^2$)=$(a-c)$/150

Absorption amount $B$ (cc/cm$^2$)=$(b-c)$/150

Measurement of Absorption Amount . . . No. 2:
1) An absorbent body cut by 100 mm×150 mm is wrapped with a non-woven fabric and the periphery is sealed to prepare a sample.
2) The sample is dipped in artificial urine for 30 minutes in a state of being applied with a load of 20 g/cm$^2$.
3) The sample is taken out of the artificial urine and is drained in a state as it stands for 3 minutes, and the weight D is measured.
4) The absorbent body is taken out of the sample and the weight E of the remaining non-woven fabric is measured. Then, an absorption amount C after absorbed under a load and drained under a load is calculated in accordance with the following equation.

Absorption amount $C$: (cc/cm$^2$)=$(d-e)$/150

Measurement of Absorption Rate:
1) An absorbent body cut by 100 mm×150 mm is placed on a table as a sample.
2) A cylindrical tool (support portion 150 mm×150 mm) with inner diameter of 27 mm is placed at the center of the sample.
3) A weight is placed on the cylindrical tool. The final examination is performed on the two cases that a total weight is A: 600 g (4 g/cm$^2$) and B: 3.0 kg (20 g/cm$^2$).
4) Artificial urine is injected, and an absorption rate is measured. As for the injection of the artificial urine, an amount of 40 cc is injected three times at 10-minute intervals.

(Diaper Performance Measurement Test)
45° liquid flow test:
1) A second sheet and top sheet are placed on an absorbent body cut by 100 mm×300 mm, and a sample is prepared by sealing the four sides.
2) The sample is attached to a 45° slanted plate and a mark is marked at a position 50 mm from the top.
3) An injection container for surface flow measurement is set and artificial urine is dropped at a rate of 12.5 cc/sec. from a height of 10 mm to the marked position. As for the dropping of the artificial urine, an amount of 50 cc is dropped four times at 10-minute intervals.

4) A surface flow distance is measured and after 5 minutes, a diffusion distance (a distance from the mark) in the absorbent body is measured.

Strike Through/Flowback Test:

1) A second sheet and top sheet are placed on an absorbent body cut by 100 mm×300 mm, and a sample is prepared by sealing the four sides.
2) A cylindrical tool (support portion 150 mm×150 mm) with inner diameter of 27 mm is placed at the center of the sample. A load is applied to a cylindrical tool if required.
3) Artificial urine is dropped and an absorption rate is measured. As for the dropping of the artificial urine, an amount of 50 cc is dropped three times at 10-minute intervals.
4) After 5 minutes, a diffusion distance in the absorbent body is measured.
5) A kitchen paper (2 ply article: three-layered and folded in four) is placed 10 minutes after the third dropping, and a backflow amount is measured by applying a load for 10 seconds with a weight of 5 kg.

Absorption Rate:

1) A second sheet and top sheet are placed on an absorbent body cut by 120 mm×300 mm, and a sample is prepared by sealing the four sides.
2) The sample is set in a U-shaped tool.
3) The U-shaped tool with the sample set is mounted on a hammock, and 2 weights of 500 g are placed thereon.
4) Artificial urine of 100 cc is injected thereinto, and an absorption rate is measured.
5) The artificial urine of 100 cc is again injected immediately after a diffusion distance is measured.
6) The absorption rate is measured at the time of injection, and after 10 minutes, the diffusion distance in the absorbent body is measured.

As is clear from the foregoing, in accordance with the present invention, although thinning is promoted, an absorbent body which can exert an absorbing performance equivalent to the one in earlier technology, which is not thinned, can be realized. In addition, an absorbent article provided with an adequate flexibility can be obtained by limiting the strength of the absorbent body to a predetermined range.

TABLE 2

|  |  | EXAMPLE 1 | EXAMPLE 2 | EXAMPLE 3 | EXAMPLE 4 | EXAMPLE 5 |
|---|---|---|---|---|---|---|
| ABSORPTION AMOUNT A (g/cm$^2$) |  | 1.52 | 2.11 | 2.05 | 1.65 | 1.70 |
| ABSORPTION AMOUNT B (g/cm$^2$) |  | 1.05 | 1.68 | 1.65 | 1.20 | 1.23 |
| ABSORPTION AMOUNT C (g/cm$^2$) |  | 0.89 | 1.23 | 1.25 | 0.93 | 0.99 |
| ABSORPTION RATE A | FIRST | 51 | 65 | 46 | 53 | 68 |
| (sec) | SECOND | 74 | 88 | 68 | 79 | 82 |
|  | THIRD | 72 | 113 | 66 | 75 | 99 |
| ABSORPTION RATE B | FIRST | 309 | 512 | 299 | 325 | 459 |
| (sec) | SECOND | 417 | 560 | 385 | 456 | 466 |
|  | THIRD | 393 | 562 | 391 | 469 | 478 |
| 45° LIQUID FLOW | FIRST | 84 | 125 | 83 | 93 | 118 |
| (mm) | SECOND | 104 | 131 | 99 | 101 | 120 |
|  | THIRD | 120 | 151 | 115 | 124 | 131 |
|  | FOURTH | 155 | 168 | 138 | 138 | 142 |
| DIFFUSION AT THE TIME OF | FIRST | 198 | 211 | 186 | 196 | 205 |
| 45° LIQUID FLOW | SECOND | 198 | 215 | 186 | 196 | 210 |
| (mm) | THIRD | 198 | 220 | 189 | 197 | 211 |
|  | FOURTH | 250 | 250 | 243 | 250 | 250 |
| FLOWBACK (g) |  | 5.4 | 3.1 | 4.5 | 5.9 | 4.6 |
| STRIKE THROUGH | FIRST | 12.5 | 18.2 | 12.9 | 11.5 | 17.3 |
| (sec) | SECOND | 13.5 | 15.3 | 13.6 | 13.1 | 16.5 |
|  | THIRD | 13.1 | 16.2 | 13.5 | 13.5 | 15.5 |
| DIFFUSION AT THE TIME OF | FIRST | 176 | 183 | 182 | 169 | 191 |
| STRIKE THROUGH | SECOND | 176 | 183 | 185 | 170 | 191 |
| (mm) | THIRD | 205 | 190 | 210 | 216 | 226 |
| ABSORPTION RATE | FIRST | 56 | 62 | 49 | 51 | 68 |
| (sec) | SECOND | 472 | 520 | 423 | 480 | 512 |

|  |  | EXAMPLE 6 | COMP. EXAMPLE 1 | COMP. EXAMPLE 2 | COMP. EXAMPLE 3 |
|---|---|---|---|---|---|
| ABSORPTION AMOUNT A (g/cm$^2$) |  | 1.98 | 1.39 | 1.43 | 1.55 |
| ABSORPTION AMOUNT B (g/cm$^2$) |  | 1.46 | 0.98 | 1.08 | 1.10 |
| ABSORPTION AMOUNT C (g/cm$^2$) |  | 1.18 | 0.79 | 0.81 | 0.90 |
| ABSORPTION RATE A | FIRST | 50 | 64 | 88 | 58 |
| (sec) | SECOND | 75 | 83 | 125 | 61 |
|  | THIRD | 76 | 102 | 136 | 88 |
| ABSORPTION RATE B | FIRST | 325 | 623 | 885 | 432 |
| (sec) | SECOND | 391 | 650 | 950 | 578 |
|  | THIRD | 436 | 623 | 1221 | 580 |
| 45° LIQUID FLOW | FIRST | 89 | 148 | 156 | 115 |
| (mm) | SECOND | 112 | 126 | 143 | 125 |
|  | THIRD | 124 | 143 | 155 | 131 |
|  | FOURTH | 145 | 168 | 178 | 146 |
| DIFFUSION AT THE TIME OF | FIRST | 189 | 235 | 238 | 215 |
| 45° LIQUID FLOW | SECOND | 189 | 238 | 245 | 218 |
| (mm) | THIRD | 191 | 249 | 250 | 220 |
|  | FOURTH | 245 | 250 | 250 | 250 |
| FLOWBACK (g) |  | 5.8 | 4.5 | 6.5 | 7.2 |
| STRIKE THROUGH | FIRST | 13.6 | 25.6 | 33.5 | 18.5 |
| (sec) | SECOND | 12.1 | 22.7 | 31.5 | 21.6 |
|  | THIRD | 12.5 | 20.7 | 34.6 | 21.1 |
| DIFFUSION AT THE TIME OF | FIRST | 189 | 185 | 189 | 199 |

TABLE 2-continued

| STRIKE THROUGH | SECOND | 189 | 207 | 221 | 221 |
|---|---|---|---|---|---|
| (mm) | THIRD | 225 | 255 | 271 | 262 |
| ABSORPTION RATE | FIRST | 55 | 107 | 156 | 89 |
| (sec) | SECOND | 460 | 723 | 1114 | 838 |

Twelfth Embodiment

Figure 35:
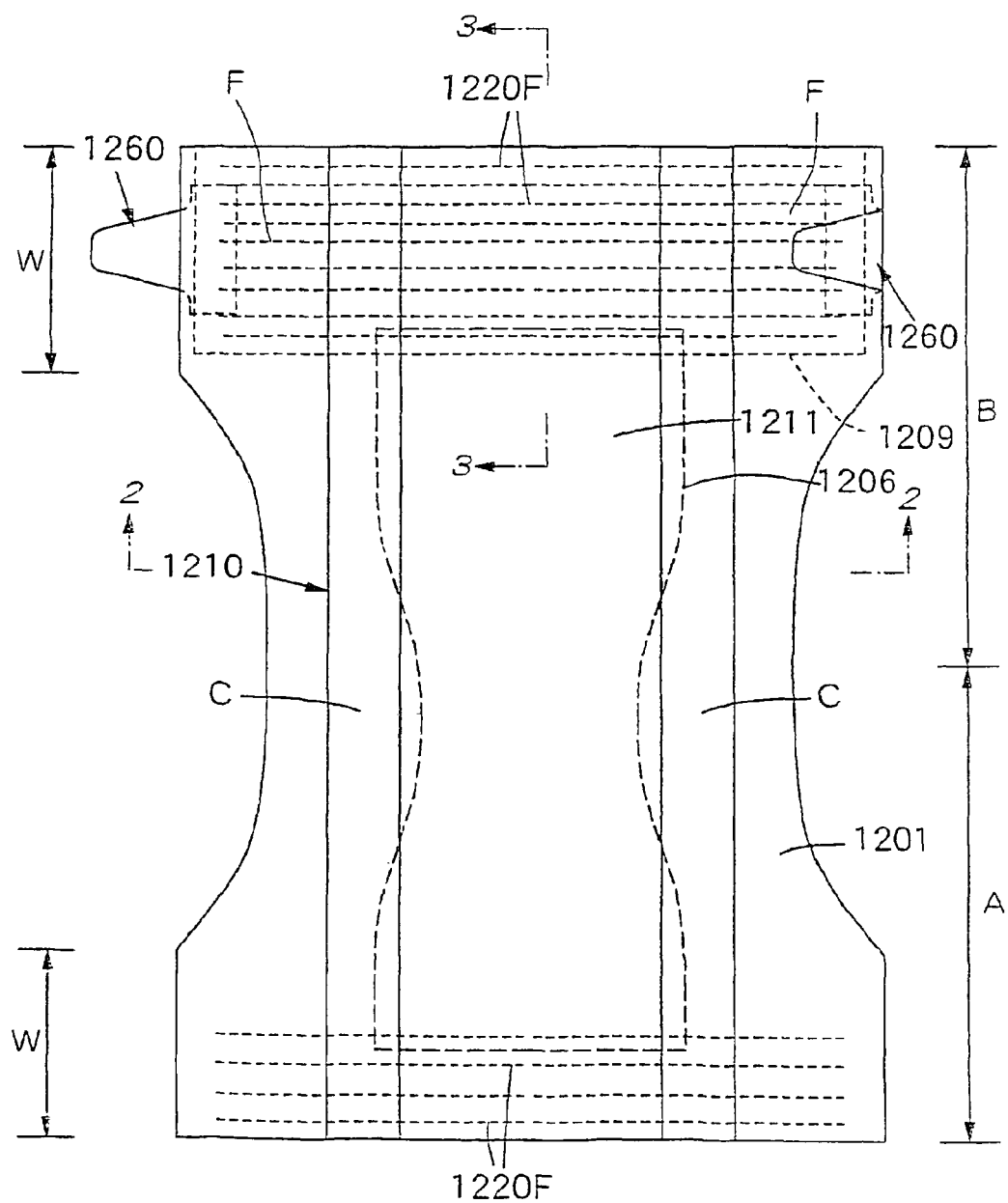
FIG. 35 is a developed plan view of a disposable diaper showing a twelfth embodiment according to the present invention.
Figure 36:
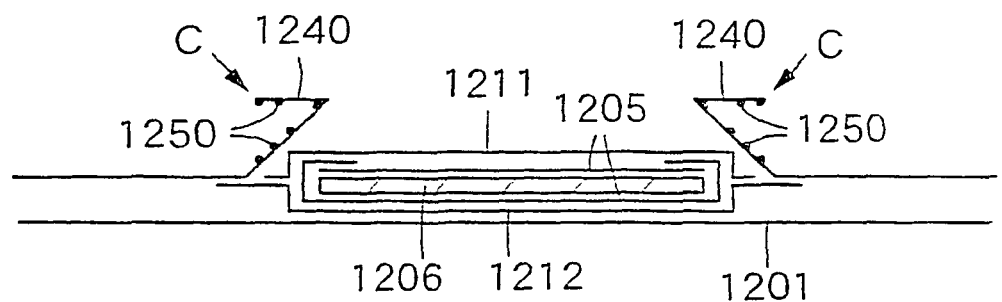
FIG. 36 is a longitudinal cross sectional view by a 2-2 arrowed line of FIG. 35.
Figure 37:
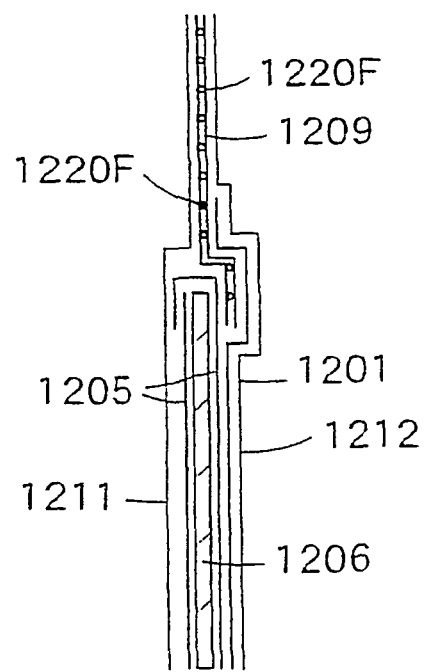
FIG. 37 is a longitudinal cross sectional view by a 3-3 arrowed line of FIG. 35.

FIG. 35 is a developed plan view showing a disposable diaper provided with a fastening tape in a twelfth embodiment according to the present invention. FIG. 36 is its 2-2 arrowed line longitudinal cross sectional view, and FIG. 37 is its 3-3 arrowed line longitudinal cross sectional view. In the disposable diaper in the embodiment, an absorber 1210 is disposed and fixed in place on the inner surface of the external sheet 1201 comprising a non-woven fabric and the like. As shown in the longitudinal cross sectional view of FIG. 36, the absorber 1210 is so formed that a sandglass-shaped liquid permeable absorbent body 1206 enclosed with a tissue paper 1205 and the like is interposed between a rectangular liquid-permeable top sheet 1211 and a non-liquid permeable back sheet 1212 such as polyethylene or the like, and the circumference is fixed in place with a hot melt adhesive or the like. Both sides of back side B are of flaps F and F - - - where the absorbent body 1206 is not provided. In the illustrated example, the rising cuffs C and C are formed on both sides of the absorber 1210. This rising cuff C is so constituted that an elastic member comprising a rubber thread or the like is retractably fixed at the rising sheet 1240. A plurality of elastic members 1220F and 1220F comprising a rubber thread or the like are retractably fixed at the body peripheral region W with a hot melt adhesive or the like between reinforced sheets 1209 and 1209 interposed between the external sheets 1201.

Figure 38:
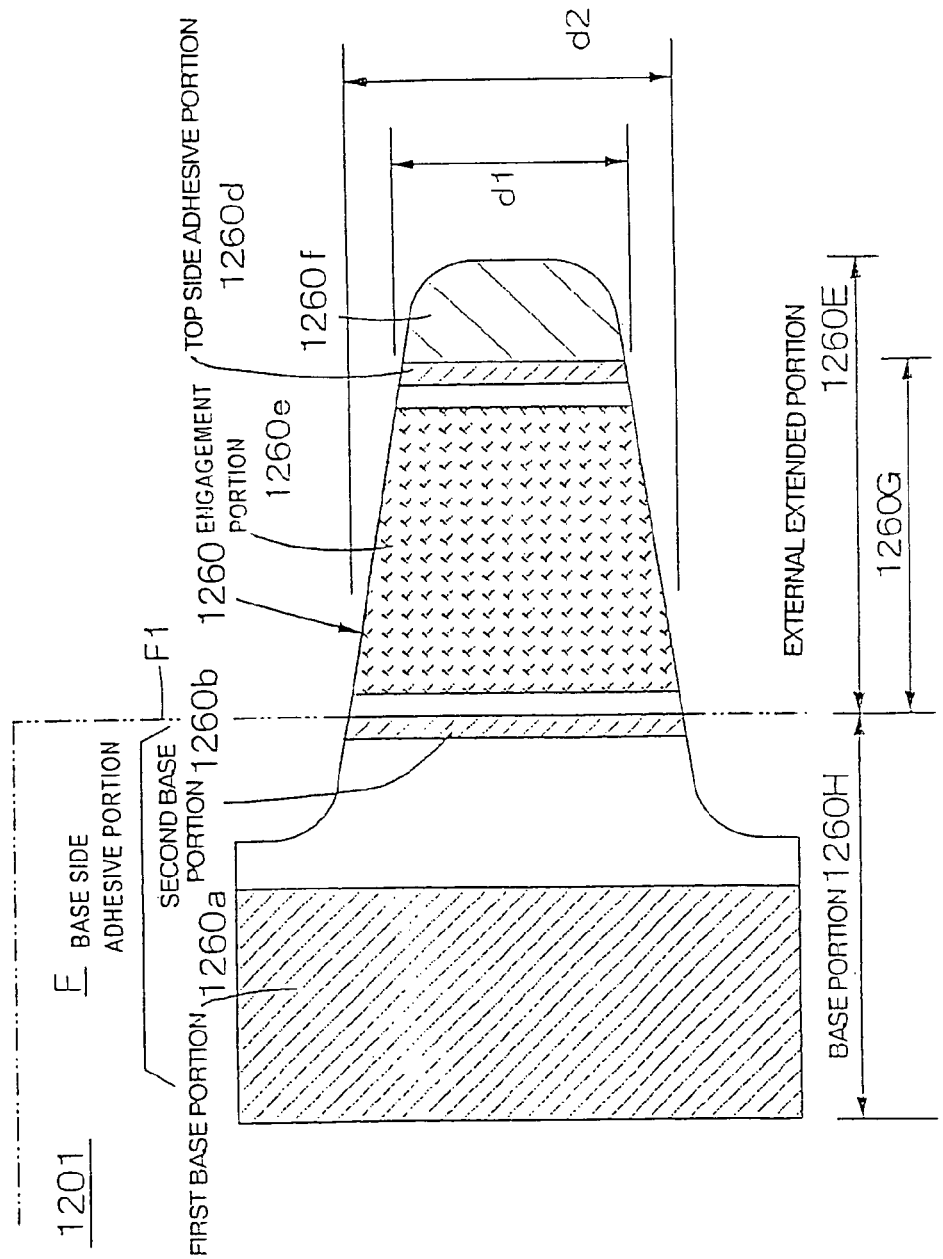
FIG. 38 is a plan view of a fastening tape portion.
Figure 39A:
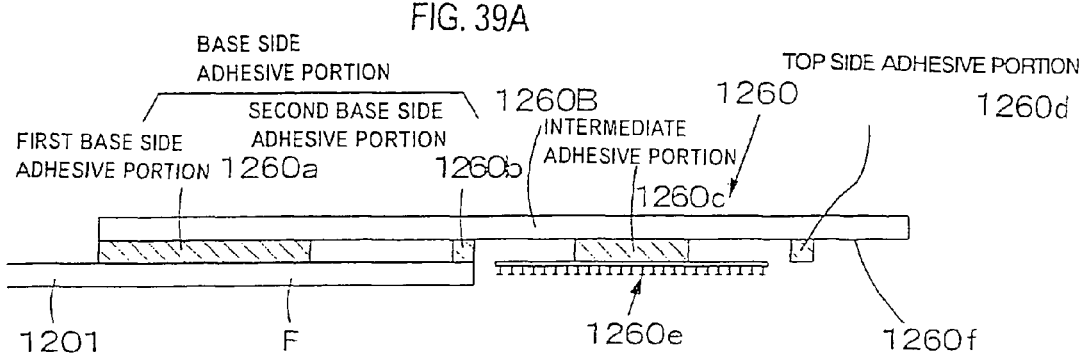
FIG. 39A and FIG. 39B are side views of a fastening tape portion.

Then, the fastening tapes 1260 and 1260 having no exfoliation tape according to the present invention are attached to the disposable diaper. As detailedly shown in FIG. 38 and FIG. 39, the fastening tape 1260 in the first embodiment according to the present invention has a first base side adhesive portion 1260a, a second base side adhesive portion 1260b, an intermediate adhesive portion 1260c and a top side adhesive portion 14 each spaced out on the inner surface of the tape substrate 1260B (the surface of the use surface of the product) in the longitudinal direction respectively. The base portion of the tape substrate 1260B is fixed in place at the side flap F of the back side B by the first base side adhesive portion 1260a and the adhesive portion 1260b. The fastening tape 1260 further has the intermediate adhesive portion 1260c at an external extended portion 1260e extended outwardly from the side edge F1 of the side flap F and the top side adhesive portion 1260d outside from the intermediate adhesive portion respectively. The engagement portion 1260e showing the relation mechanically engaged by the intermediate adhesive portion 1260e is fixed in place, and the top side adhesive portion 1260d is located outside the engagement portion 1260e. In addition, in accordance with the present invention, the fastening tape 1260 has no adhesive portion between the engagement portion 1260e and the flap side edge F1.

The engagement portion 1260e comprises a sheet where a number of microscopic hooks such as fungiform or the like comprising resins such as polypropylene, polyethylene terephthalate and the like are formed, and for example, at the center on the back side of the sheet, it is bonded with the intermediate adhesive portion 1260c on the tape substrate 1260B. Although in the illustrated example, the intermediate adhesive portion 1260c is provided only in the middle of the engagement portion 1260c, and other portions are bonded to the tape substrate 1260B with a hot melt adhesive in the manufacturing step of the fastening tape, the entire back side of the engagement portion 1260e can be of course bonded to the tape substrate 1260B with the intermediate adhesive portion 1260c.

It is desirable that as illustrated, the engagement portion 1260e is formed so as to allow the top width d1 thereof to be 10 to 90% of the base width d2, particularly 10 to 80%. In addition, for the engagement portion 1260e, the engaging force to the corresponding hook receptacle is 50 to 1,000 g per hook portion width of 25 mm, particularly 100 to 500 g, the engaging force to the non-woven fabric surface is 50 to 1,000 g per hook portion width of 25 mm, and particularly 50 to 300 g is desirable.

On the other hand, it is preferred that the first base side adhesive portion 1260a, the adhesive portion 1260b, the intermediate adhesive portion 1260c and the top side adhesive portion 1260d are formed of, for example, styrene series adhesives, the adhesion can be the same or can be different at each portion. Although the adhesion force can suitably be controlled by polymerization degree or the amount of a base polymer, it is preferred to be 50 to 300 g per adhesive portion width.

In addition, in the twelfth embodiment according to the present invention, the top side adhesive portion 1260d is spaced out from the engagement portion 1260e, and is also spaced out from the intermediate adhesive portion 1260c accordingly. Although the adhesion force of the intermediate adhesive portion 1260c can be the same as or can be different from those of the top side adhesive portion 1260d and the adhesive portion 1260b, it is desirable that the adhesion force of the intermediate adhesive portion 1260c is larger than those of the top side adhesive portion 1260d and the adhesive portion 1260b.

In addition, in this example, the base side adhesive portion is constituted by allowing the first base side adhesive portion 1260a and the adhesive portion 1260b to be spaced out and to be formed on the inner surface of the base portion 1260H located inwardly from the flap side edge F1 in the external extended portion 1260E of the fastening tape 1260. This adhesive portion 1260b can be omitted or the first base side adhesive portion 1260a and the adhesive portion 1260b may be integrated and an adhesive portion may be provided on the entire base portion 1260H.

In addition, in this example, the portion on the top portion from the top side adhesive portion 1260d in the external extended portion 1260E of the fastening tape 1260 and the tape substrate 1260B having no fastening factors such as engagement portions and adhesive portions and the like are exposed as they stand which are the knob portion 16. This knob portion 1260f can be so eminently constituted that the tab tape of a color which can distinguish the surroundings is affixed, and the coloring which can distinguish the surroundings by coloring the knob portion per se is performed. In addition, in order to allow the base side border of the knob portion 1260f to be eminent, the top side adhesive portion 1260d can be formed with the adhesive of a color which can distinguish the surroundings.

The more desirable dimension constitutions of the fastening tape according to the present invention are listed as follows:

The area of A knob portion 1260*f* is set to be 10 to 40% to the area of the portion 1260G between the knob portion 1260*f* and the region corresponding to the flap side edge F1.

The area of B engagement portion 1260*e* is set to be 10 to 40% to the entire area of the fastening tape (namely, the entire area of the tape substrate 1260B).

The area of C top side adhesive portion 1260*d* is set to be 5 to 40% to the engagement portion 1260*e*.

The area of D top side adhesive portion 1260*d* is set to be 2 to 15% to the area of the external extended portion 1260E.

The area of E adhesive portion 1260*b* is 2 to 10% to the area of the base portion 1260H inside from the flap side edge F1 in the fastening sheet 1260.

The area of the first base side adhesive portion 1260*a* of F fastening tape is set to be 40 to 80% to the entire area of the fastening tape 1260.

Figure 39B:
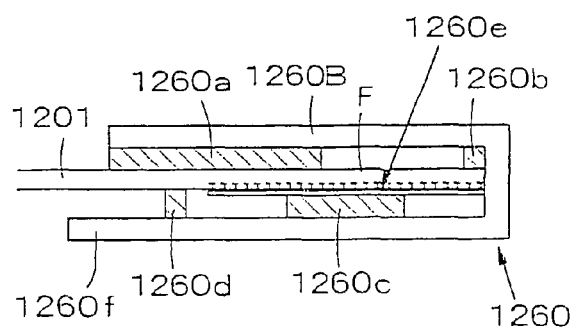

For the disposable diaper constituted as above-mentioned the external extended portions 1260E of the fastening tape 1260, as shown as in the product state in the right side in FIG. 35 and as shown in the left side in FIG. 39B and FIG. 6, are folded inside the flap F (on the use surface of the diaper), are engaged, adhered and temporarily fastened on the inner surface of the flap F facing to the engagement portion 1260*e* and the top side adhesive portion 1260*d* on the inner surface respectively. In addition, the adhesive portion 1260*b* is bonded to the external surface of the external sheet 1201 comprising the non-woven fabric in the flap F.

Figure 40:
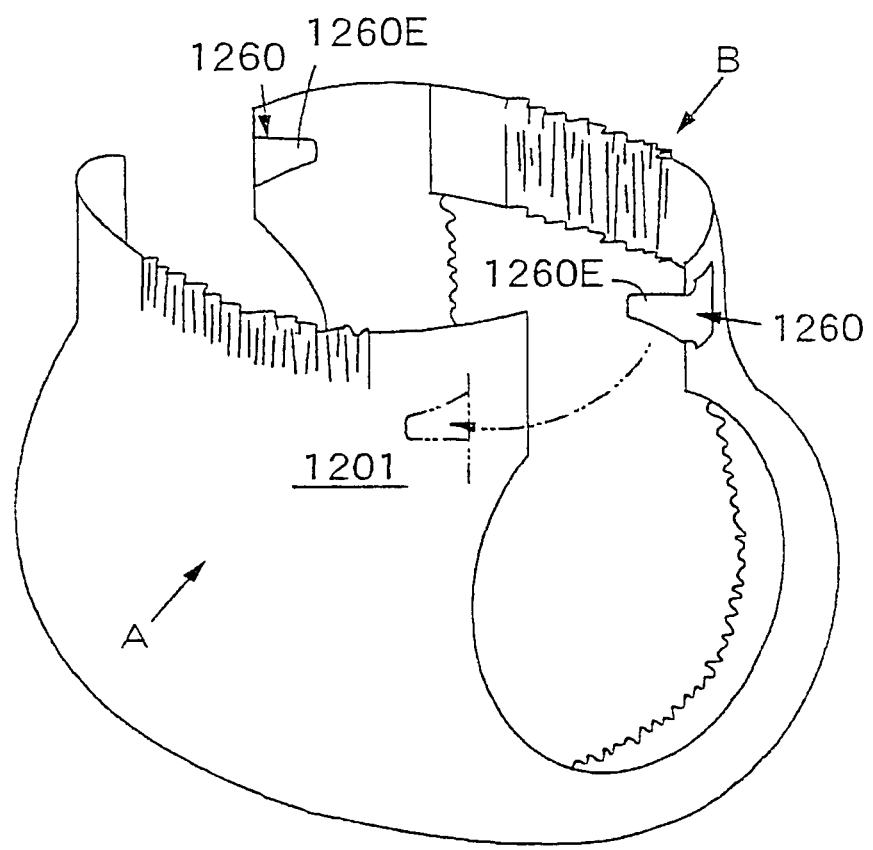
FIG. 40 is a perspective view of a disposable diaper showing the twelfth embodiment according to the present invention.
Figure 41:
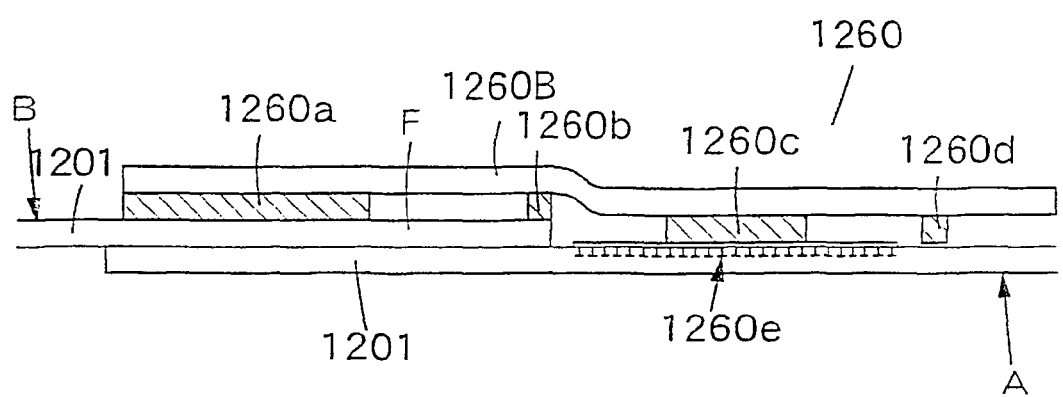

In addition, when a diaper is put on, as shown in two-dot chain line in FIG. 40, the external extended portion 1260E of the fastening tape 1260 can be developed by unfastening each temporary fastening by the top side adhesive portion 1260*d* and the engagement portion 1260*e* and can be directly fastened without an adhered tape as shown in FIG. 41 at a predetermined position on the external surface of the external sheet 1201 comprising the non-woven fabric on the diaper belly side A. In this fastening, a fastening force is exerted by allowing the engagement portion 1260*e* to be entangled with the non-woven fabric fibers of the external sheet 1201.

Figure 42:
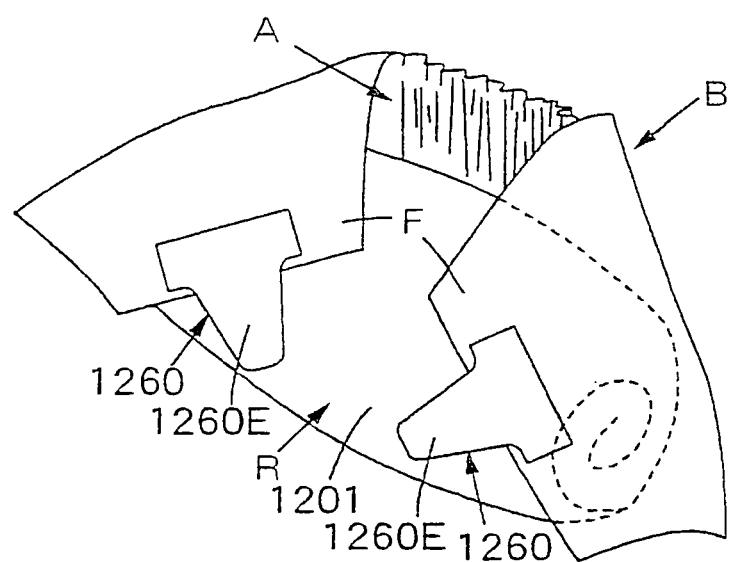

Further, when the diaper is disposed of, as shown in FIG. 42, the crotch portion of the diaper is wound toward the belly side A and is rounded in a state that the belly side A and the back side B are overlapped, next, the flaps. F and F of the back side B are folded back to the external surface of the tangling portion R (the external surface of the external sheet 1201) and the external extended portions of the fastening tapes 1260 and 1260 of each flap F and F are pressed against the external surface of the tangling portion R, and a final fastening is performed by allowing the engagement portion 1260*e* to be engaged with the external surface of the tangling portion R.

Figure 43:
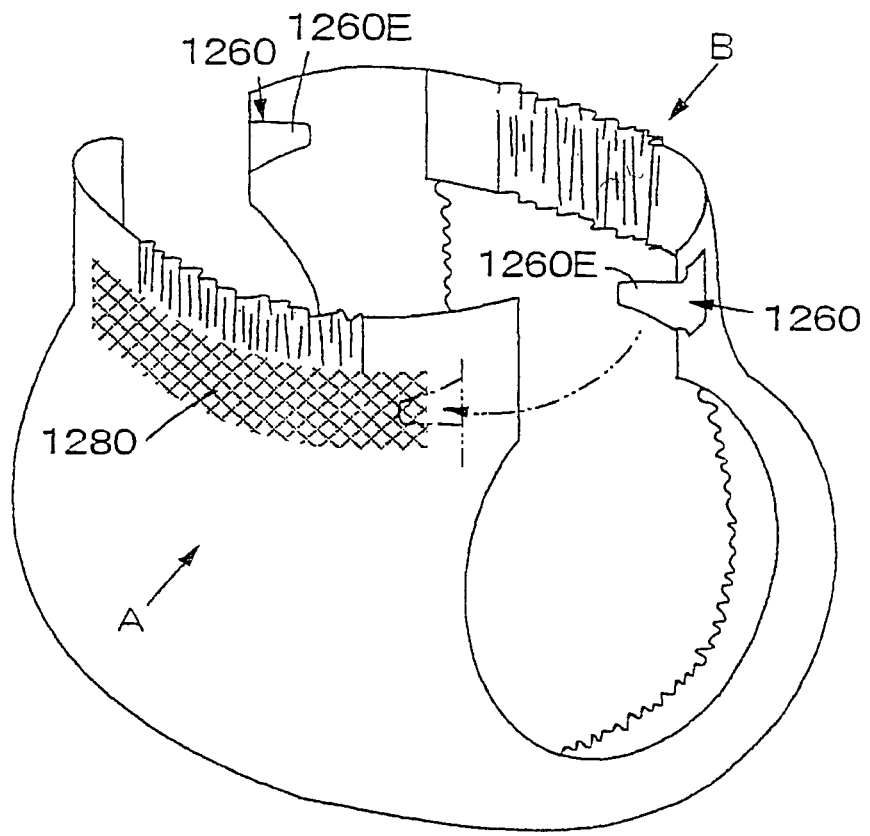
FIG. 43 is a perspective view of a disposable diaper having a distortion processed portion.

In the present invention, as described above, an adhered tape as the targets of the fastening tapes 1260 and 1260 is not provided on the external surface of the belly side in the product, and as shown in FIG. 43, the targets of the fastening tapes 1260 and 1260 are provided by arranging the distortion processed portion 1280 to which a distortion in the appearance is applied by emboss processing or the like.

Fastening can be easily performed by identifying the fastening region since the distortion processed portion 1280 is provided. In addition, an air permeation can be hardly impaired since no adhered tape is provided.

(Various Forms of Distortion Processed Portion)

The distortion processed portion can be formed by emboss processing, crepe processing, or bellows processing or the like. Namely, as shown in FIG. 44, for example, slanted grid-like emboss 1280A can be formed.

Figure 48:
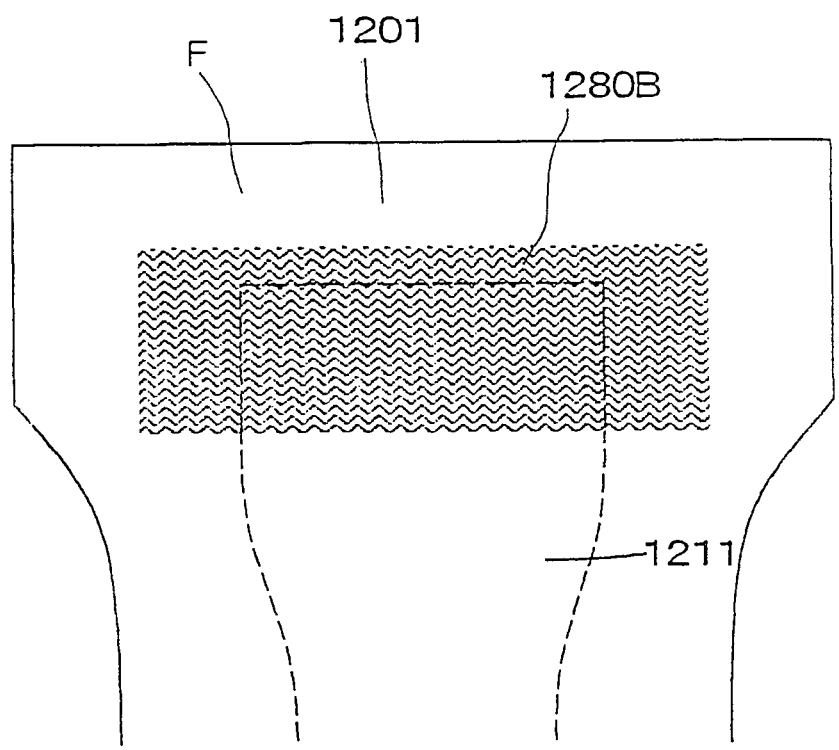
FIG. 48 is a major portion front view of other example of a distortion processed portion.
Figure 49:
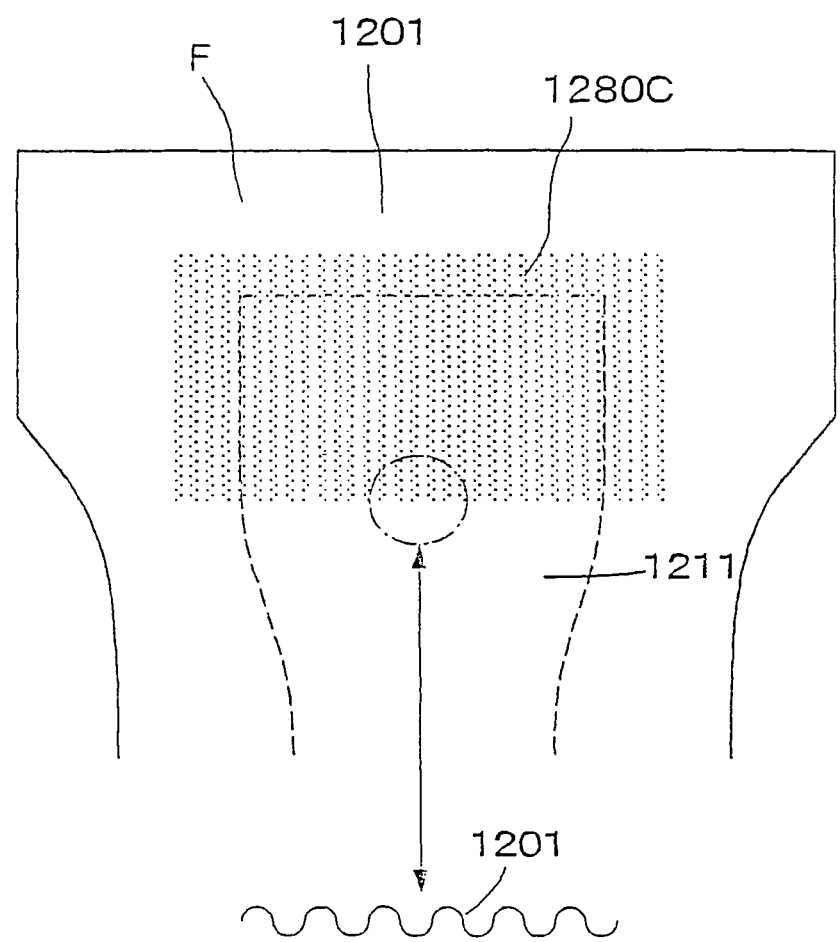
FIG. 49 is a major portion front view of a further example of a distortion processed portion.

In addition, as shown in FIG. 48, the crepe processed portion 1280B (including wrinkle processing in a broad sense) can be also formed. As shown in FIG. 49, the bellows processed portion 1280C can be also formed.

Figure 44:
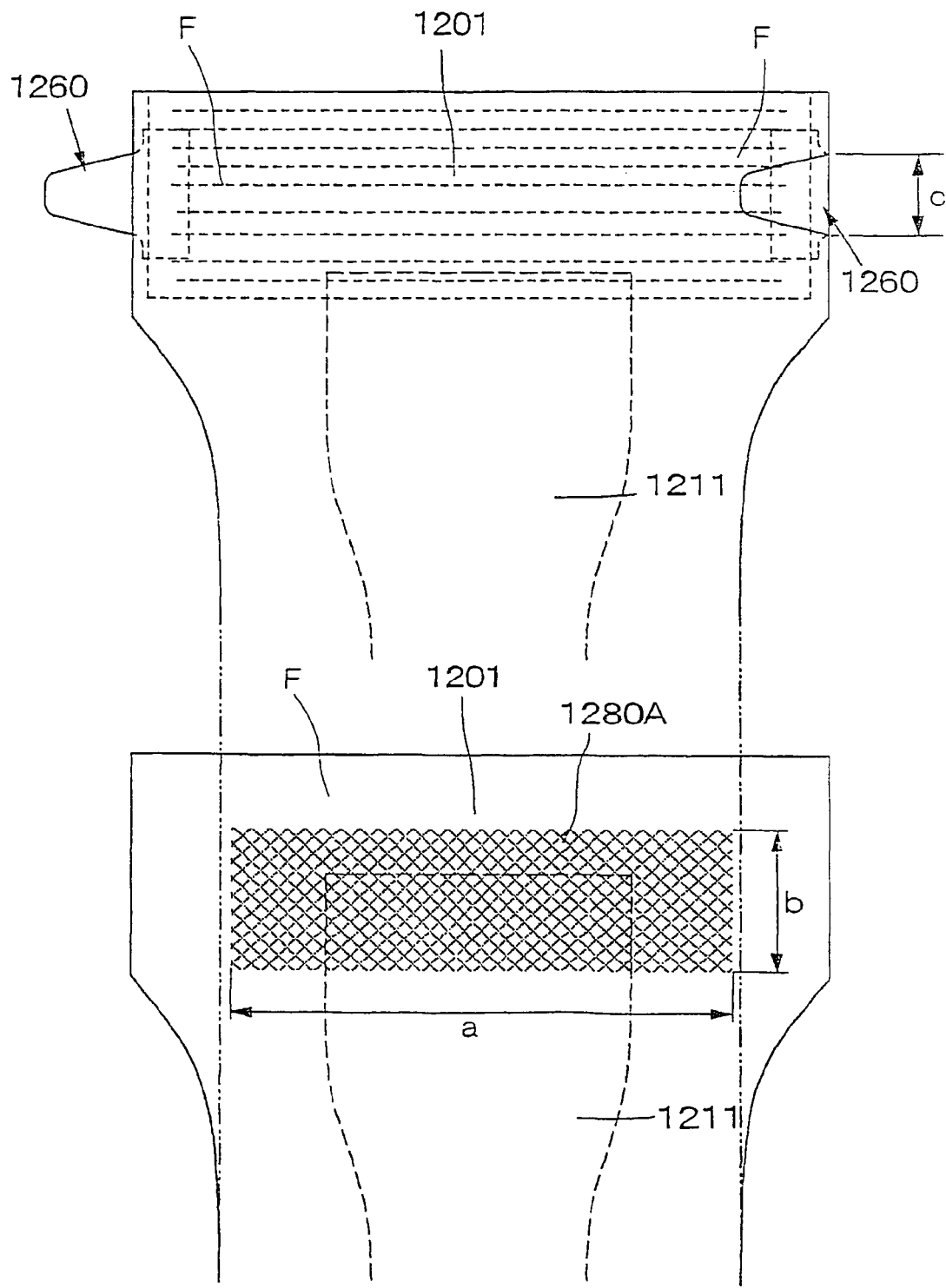
FIG. 44 is its developed front view.

In each distortion processed portion 1280 to 1280C, a proper one can be selected in a range of a=50 to 500 mm and b=10 to 400 mm in the dimensions as shown in FIG. 44. It is desirable that the dimension b is longer than the length c (not less than 50 mm is desirable) in the longitudinal direction of the product of the fastening tape 1260.

Figure 45:
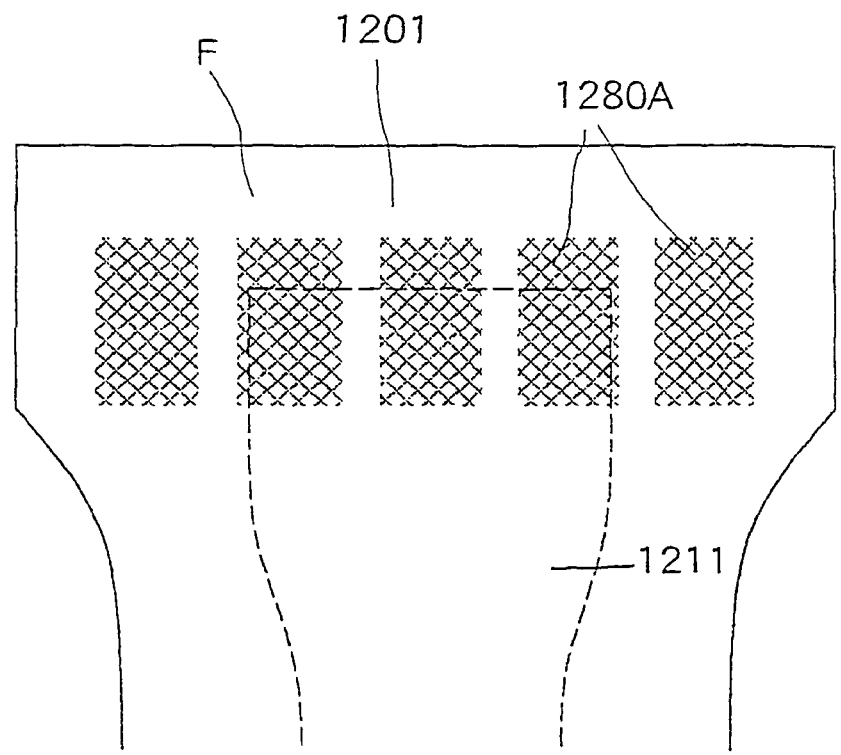
FIG. 45 is a major portion front view of another example of a distortion processed portion.
Figure 46:
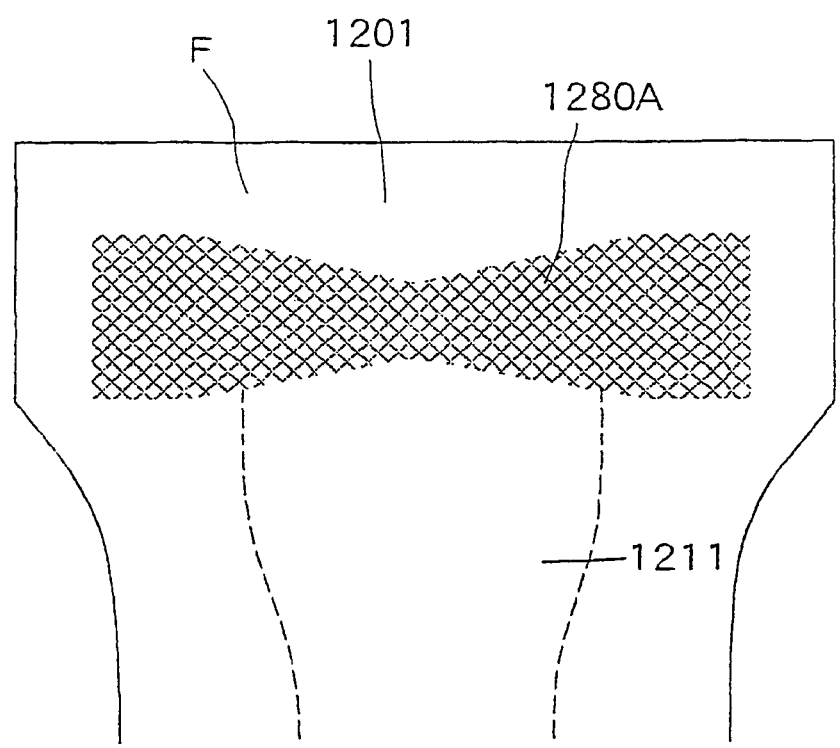
FIG. 46 is a major portion front view of another example of a distortion processed portion.
Figure 47:
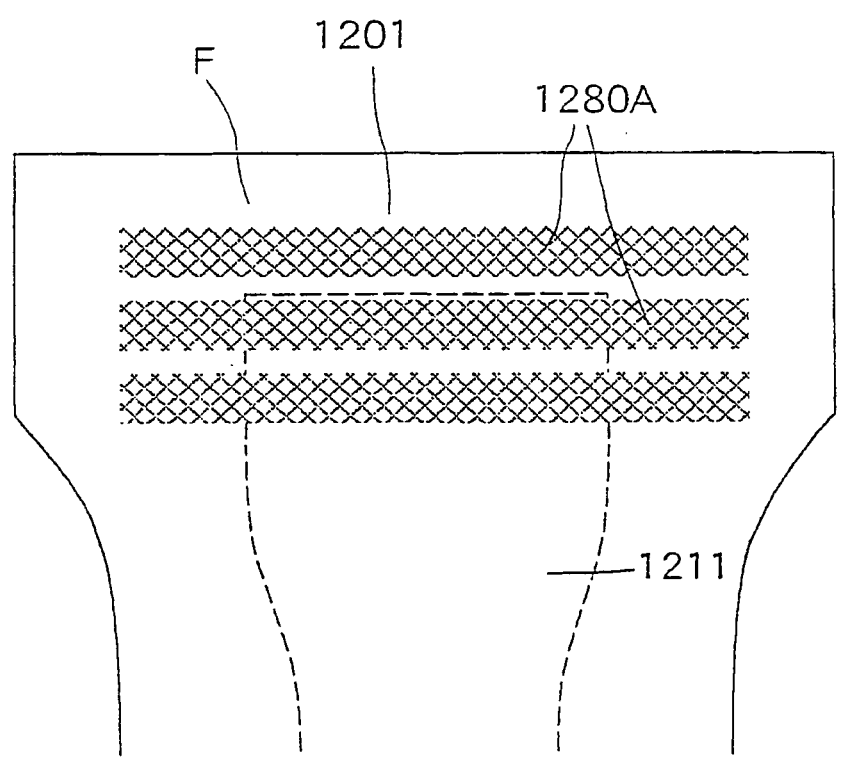
FIG. 47 is a major portion front view of another example of a distortion processed portion.

On the other hand, the shape of the distortion processed portion 1280 can be suitably selected. For example, as a modified example of the emboss 1280A, as shown in FIG. 45, it can be formed by dividing the portion in the body peripheral direction (width direction in the drawing). The position in the body peripheral direction can be judged from the divided state. As shown in FIG. 46, the center can be narrowed. The position in the body peripheral direction of the girth can be judged from the narrowed state. As shown in FIG. 47, a plurality of portions can be formed by spacing out the portions in the longitudinal direction of the production. The position in the longitudinal direction of the product can be judged.

(Forms Relating to Distortion Processed Portion)

Figure 50:
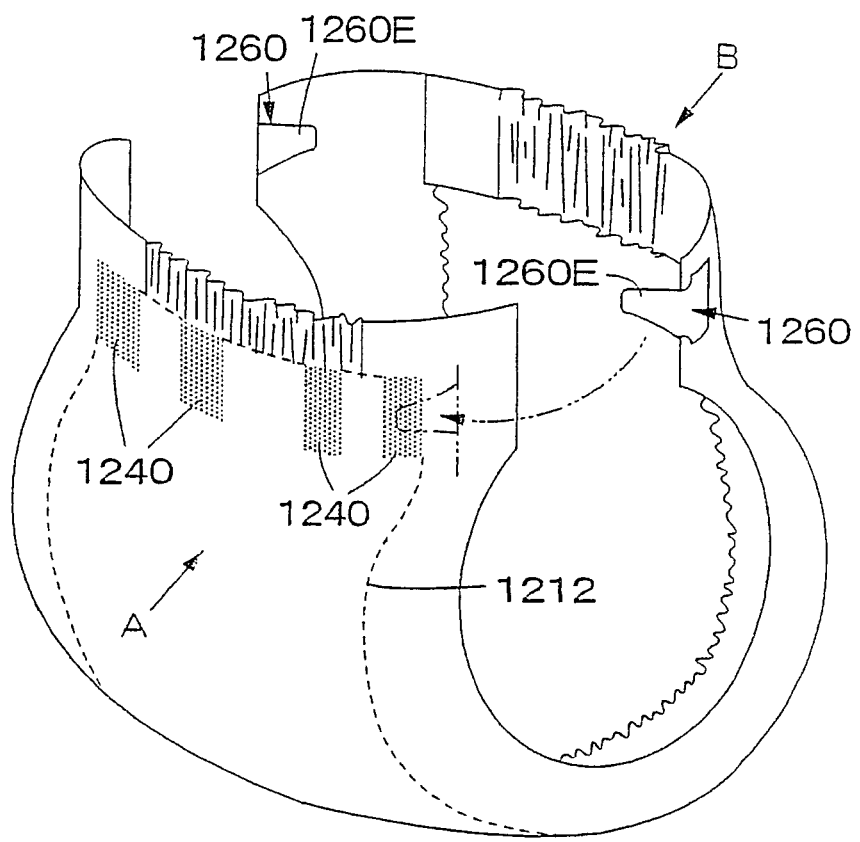
FIG. 50 is a perspective view of a disposable diaper showing a thirteenth embodiment according to the present invention.

The present invention also proposes that the distortion processed portion is so constituted that a mark 1240 is printed at a position corresponding to the fastening region of the fastening tape 1260 on the external surface of the non-liquid permeable back sheet 1212 as described above as shown in FIG. 50, besides the formation of the distortion processed portion 1280, if required, and the mark 1240 can be seen through from the external surface of the external sheet 1201. Although not illustrated, the fastening mark portion can be directly printed on the external surface of the external sheet 1201. The mark 1240 in this case may be allowed to correspond to the position of the distortion processed portion 1280 or may be different therefrom.

Thirteenth Embodiment

Figure 51:
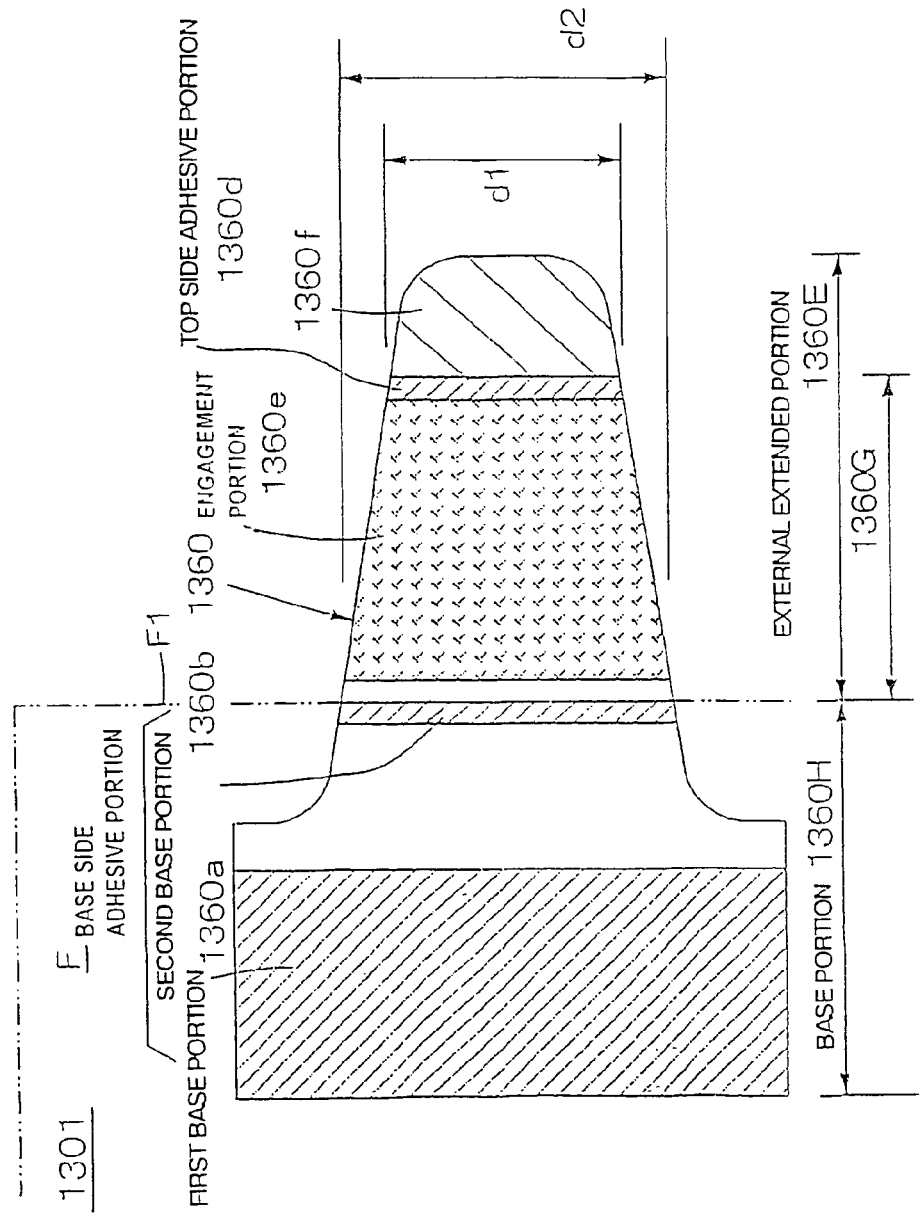
FIG. 51 is a plan view of a fastening tape portion showing the thirteenth embodiment according to the present invention.
Figure 52:
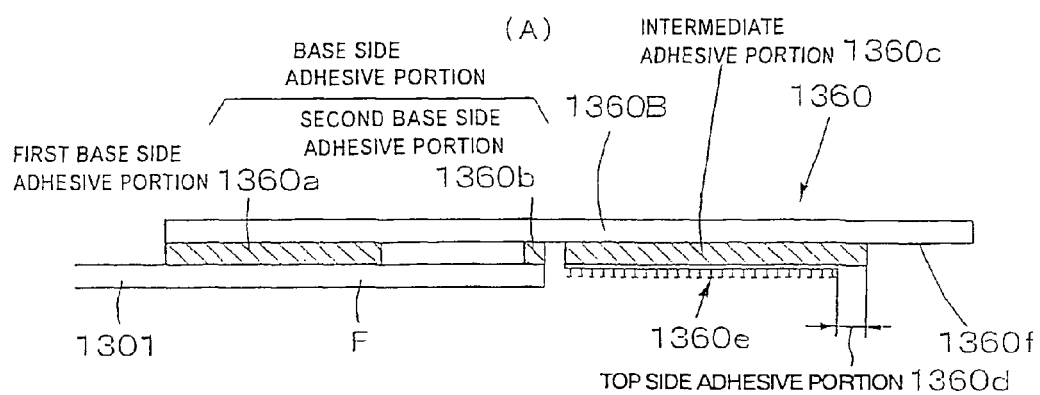
FIG. 52 is a side view of the fastening tape portion.

Although in the twelfth embodiment, the intermediate adhesive portion 1260 is located only on the back of the engagement portion 1260*e*, therefore, the top side adhesive portion 1260*d* is formed independent of the intermediate adhesive portion 1260*c*, as shown in FIG. 51 and FIG. 52, the intermediate adhesive portion 1360*c* can be allowed to protrude from the end of the engagement portion 1360*e*, and this protruded portion of the adhesive can also form the top side adhesive portion 1360*d*. This method has an advantage that it is easy to manufacture the top side adhesive portion, since it is enough to merely coat an adhesive for bonding the engagement portion 15 and an adhesive for the top side adhesive portion 14 over the tape substrate 1360B as the intermediate adhesive portion 1360*c* integrally.

(First Manufacturing Form of Fastening Tape and Disposable Diaper)

Figure 53A:
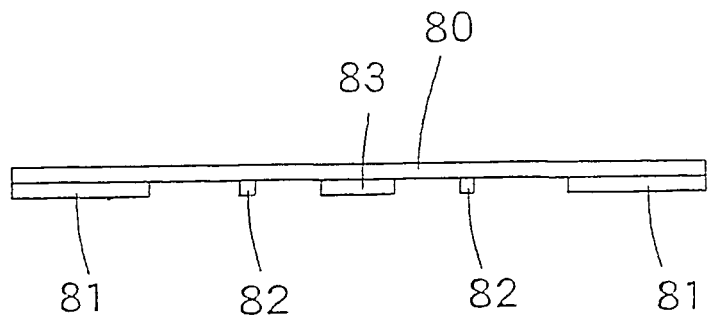
FIG. 53A and FIG. 53B are a longitudinal cross sectional view and a plan view showing the first step of the first manufacturing form of a fastening tape and a disposable diaper, respectively.
Figure 53B:
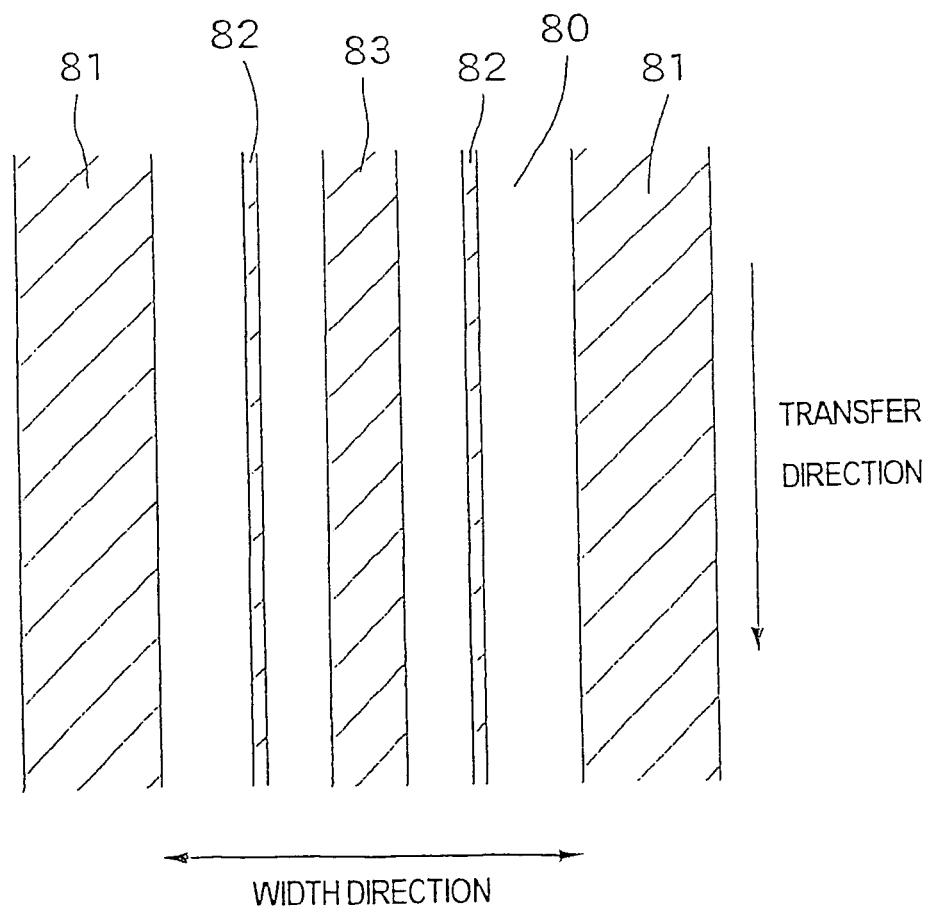

On the other hand, the fastening tapes 1260 and 1360 according to the present invention as described above can be manufactured as follows. In the first place, as shown in FIGS. 53A and 53B, the left end adhesive portion 81L, the left side adhesive portion 82L, the central adhesive portion 83, the right side adhesive portion 82R and the right end adhesive portion 81R are continuously coated in the longitudinal direction relative to the width direction on the single side of the tape substrate 80 respectively, and the tape substrate roll in a wound state can be obtained, while the continuous-band tape substrate 80 with a predetermined width is allowed to run on the manufacturing line.

Figure 54A:
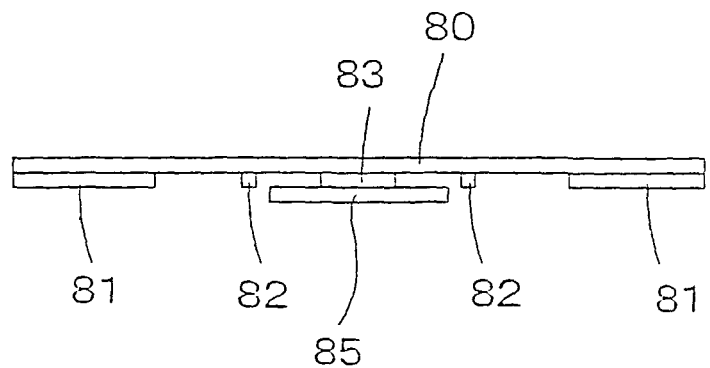
FIG. 54A and FIG. 54B are a longitudinal cross sectional view and a plan view showing the second step of the first manufacturing form, respectively.
Figure 54B:
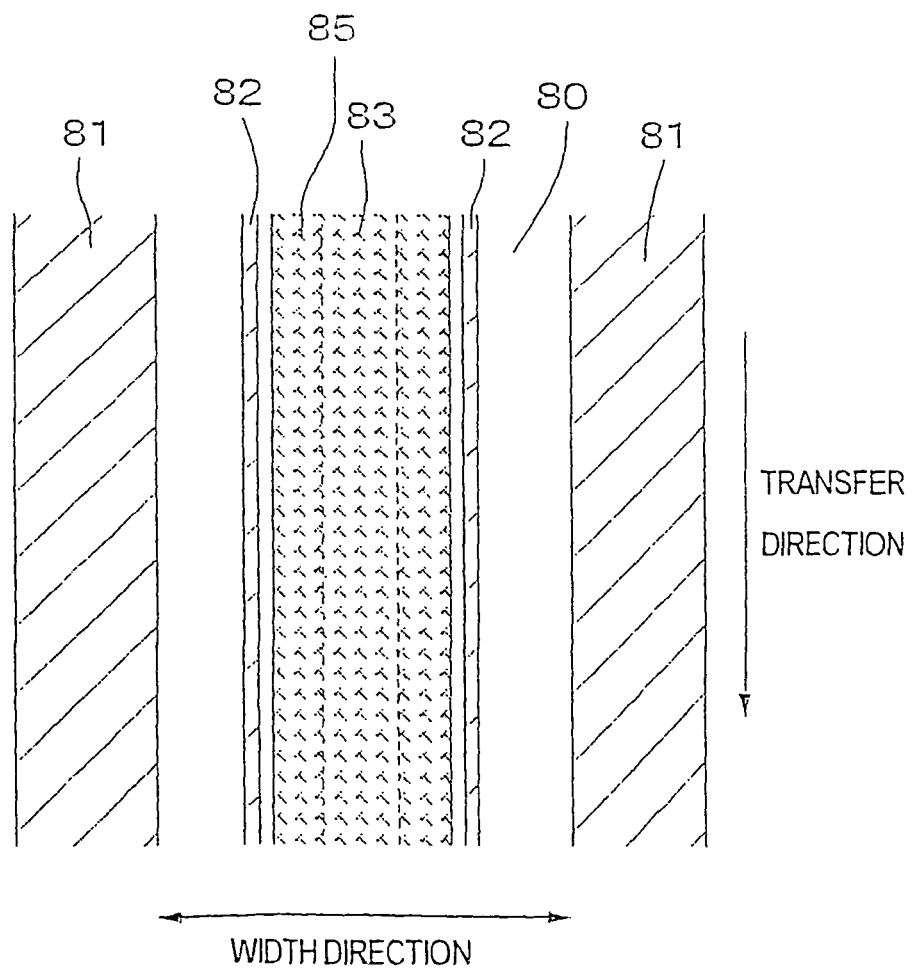

Next, this tape substrate roll is let out, as shown in FIGS. 54A and 54B, and the engagement portion sheet 85 showing the relation that the sheet 85 is mechanically engaged with the central adhesive portion 83 is continuously bonded to the central adhesive portion 83 in the longitudinal direction.

Figure 55A:
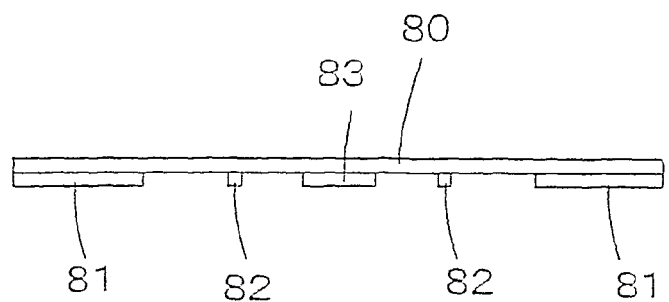
FIG. 55A and FIG. 55B are a longitudinal cross sectional view and a plan view showing the third step of the first manufacturing form, respectively.
Figure 55B:
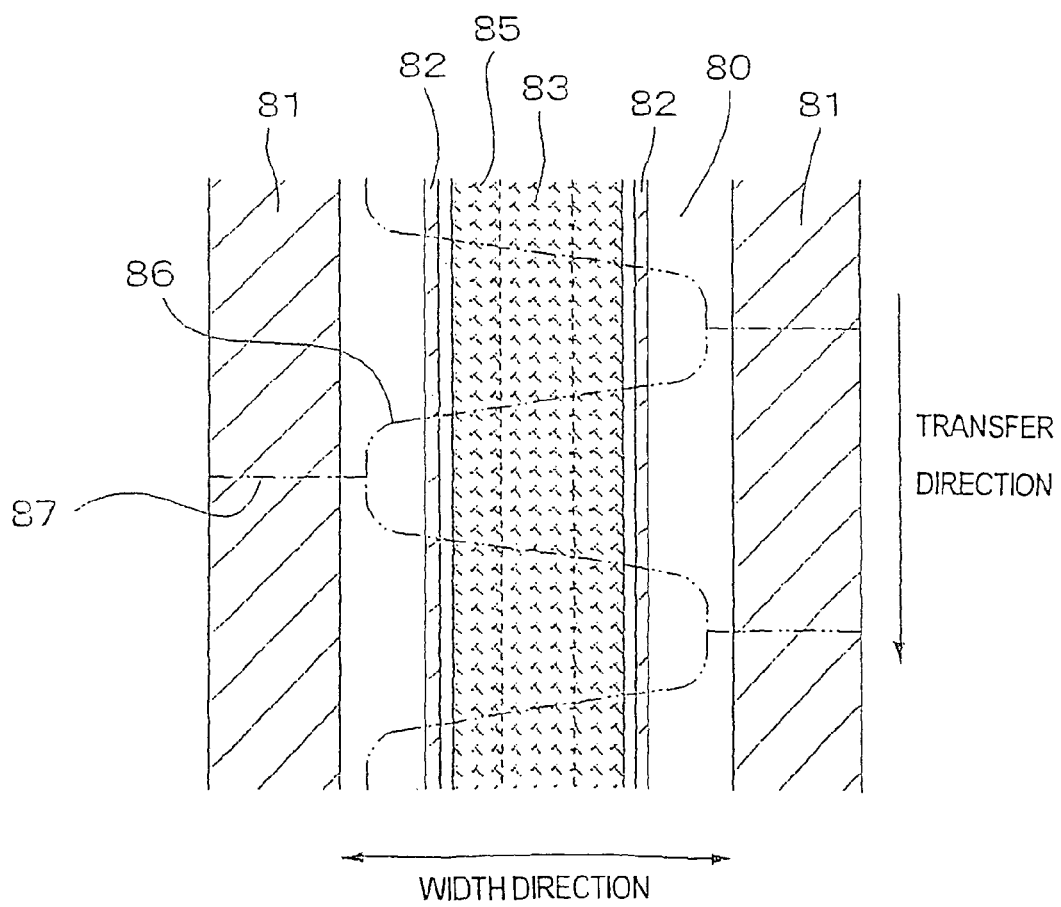

Subsequently, as shown in FIGS. 55A and 55B, the first cutting is performed on only the areas of the left side adhesive portion 82L, the central adhesive portion 83 and the right side adhesive portion 82R according to the first cutting line 86 of the waveform which simultaneously traverses the portion of the engagement portion sheet 85.

At the same time or subsequently, the second cutting is performed according to the second cutting line 87 in the width direction which links the peak of the waveform of the first cutting line 86 to the side edge of the tape substrate 80 which is the nearest to the peak.

After performing the first cutting process according to the first cutting line 86 and the second cutting process with the second cutting line 87, the individualized left side fastening tapes 1260, 1360 - - - and the right side fastening tapes 1260, 1360 - - - are obtained.

Thus, as shown in FIG. 56, for the fastening tapes 1260 and 1360 obtained from the left side, the left end adhesive portion 81L and the left side adhesive portion 82L used as the first base side adhesive portion 1260*a* and the adhesive portion 1260*b* in the twelfth embodiment are mounted on the left side portion on the back side of the semi-finished product, the central adhesive portion 83 can be used as the intermediate adhesive portion 1260*c* in the twelfth embodiment, and the right side adhesive portion 82R can be used as the top side adhesive portion 1260*d* in the twelfth embodiment. On the other hand, for the fastening tapes 1260 and 1360 obtained from the right side, the right end adhesive portion 81R and the right side adhesive portion 82R used as the first base side adhesive portion 1260*a* and the adhesive portion 1260*b* in the twelfth embodiment are mounted on the left side on the back of the semi-finished product, the central adhesive portion 83 can be used as the intermediate adhesive portion 1260*c* in the twelfth embodiment, and the left side adhesive portion 82L can be used as the top side adhesive portion 1260*d* in the twelfth embodiment.

(Second Manufacturing Form of Fastening Tape and Disposable Diaper)

Incidentally, the fastening tape 1360A which is similar to the fastening tape in the thirteenth embodiment as shown in FIG. 51 and FIG. 52 is obtained, and this fastening tape can be mounted on the sides on the back side of the product.

Figure 57A:
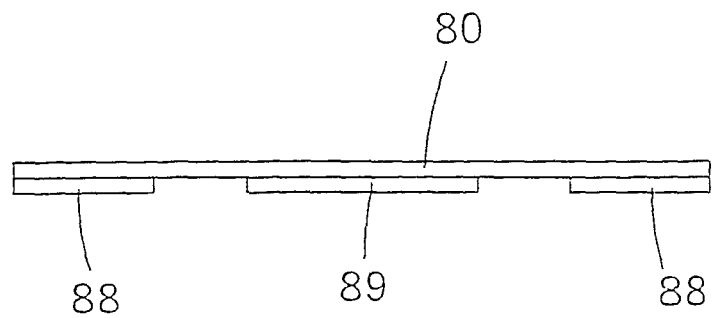
FIG. 57A and FIG. 57B are a longitudinal cross sectional view and a plan view showing the first step of the second manufacturing form of a fastening tape and a disposable diaper, respectively.
Figure 57B:
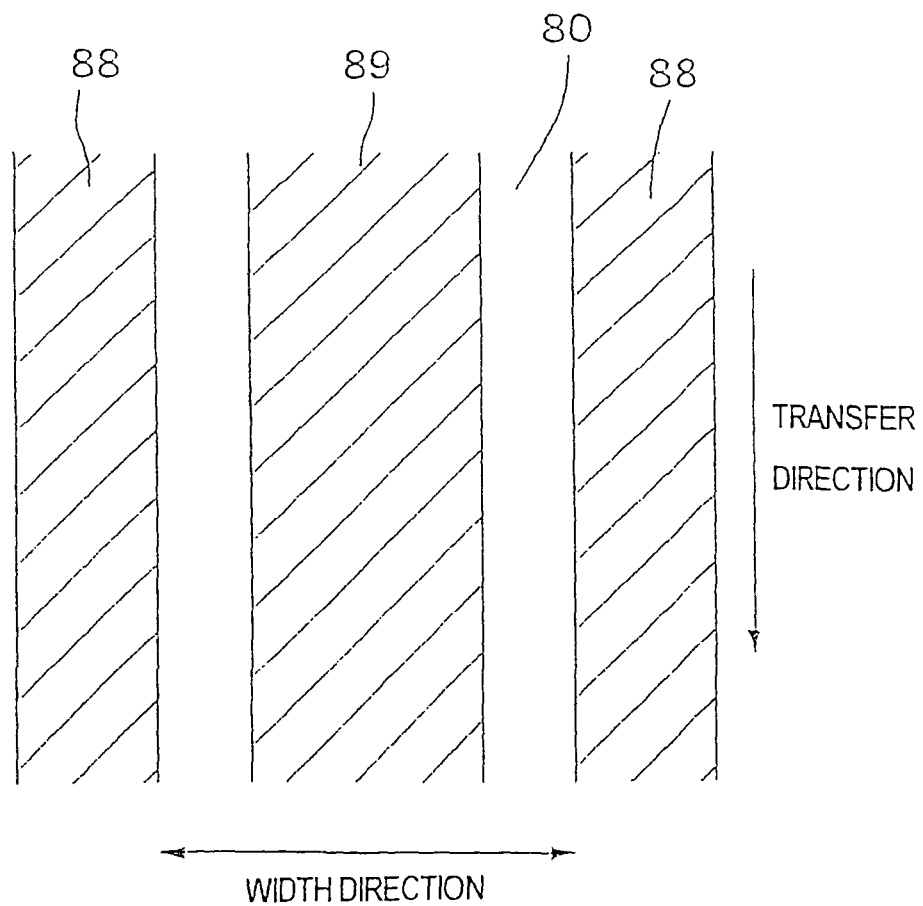

In the first place, as shown FIGS. 57A and 57B, the left end adhesive portion 88L, the central adhesive portion 89 and the right end adhesive portion 88R are continuously coated in the longitudinal direction relative to the width direction on the single side of the tape substrate 80 respectively, and the tape substrate roll in a wound state can be obtained, while the continuous-band tape substrate 80 with a predetermined width is allowed to run on the manufacturing line.

Figure 58A:
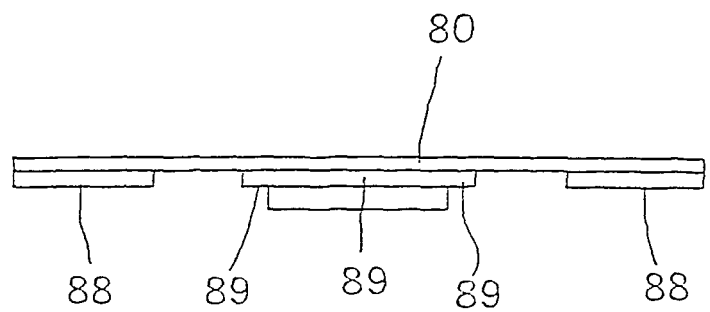
FIG. 58A and FIG. 58B are a longitudinal cross sectional view and a plan view showing the second step of the second manufacturing form.
Figure 58B:
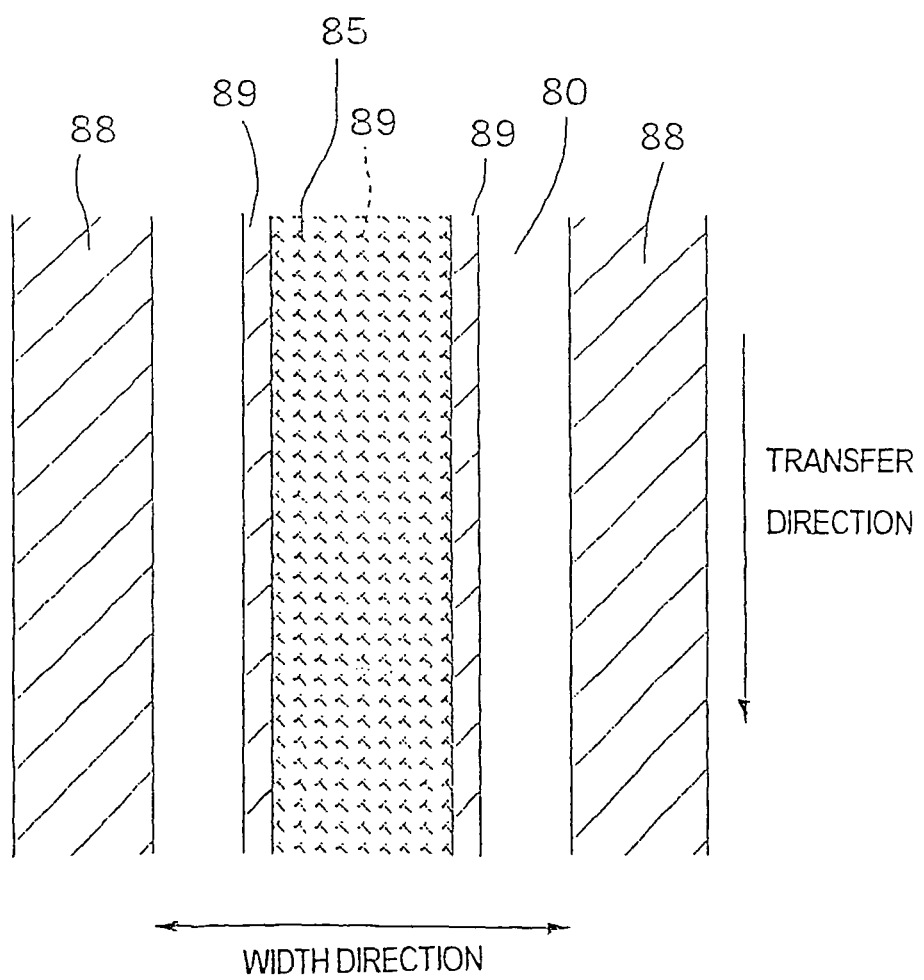
Figure 60:
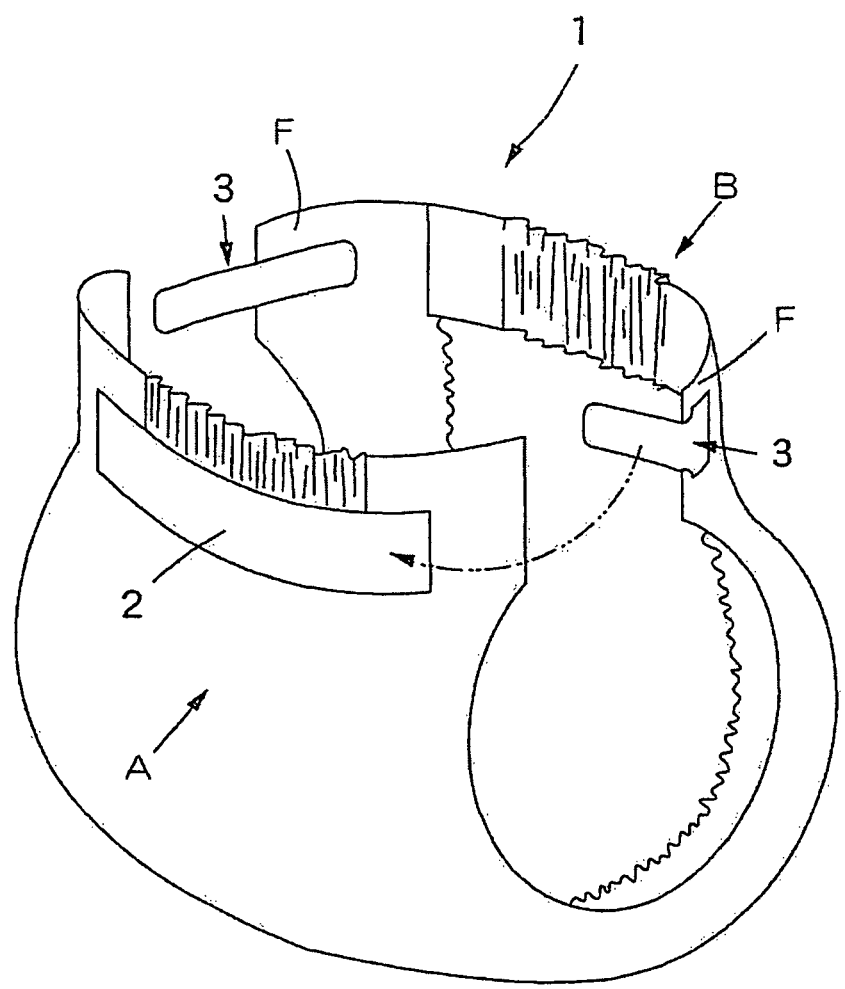
FIG. 60 is a perspective view showing an example of a disposable diaper in earlier technology.
Figure 61:
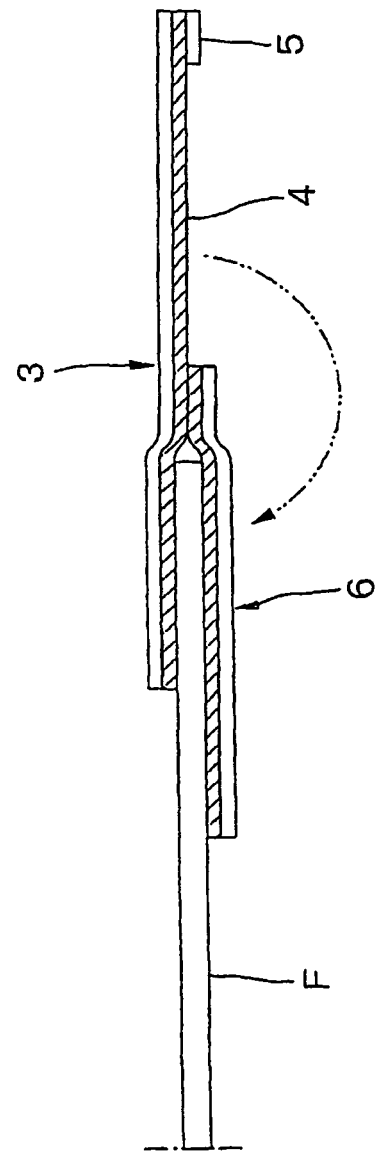
FIG. 61 is a side view of an adhesive-type fastening tape.
Figure 62:
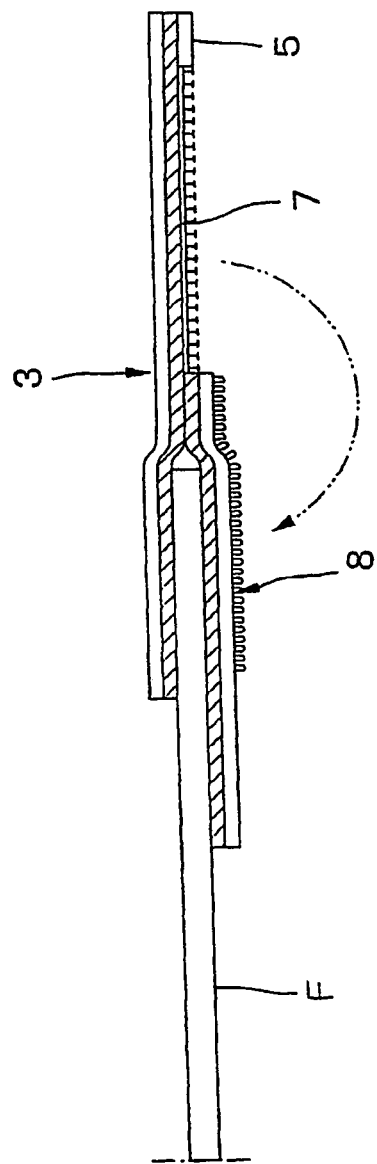
FIG. 62 is a side view of a surface fastener-type fastening tape.

Next, this tape substrate roll is let out, as shown in FIGS. 58A and 58B, the engagement portion sheet 85 showing the relation that the sheet 85 is mechanically engaged with the central adhesive portion 89 is continuously bonded to the central adhesive portion 89 in the longitudinal direction. In this case, the engagement portion sheet 85 is located at the center except for both sides of the central adhesive portion 89, and the portions 89L and 89R on which the adhesive portions are exposed are left on both sides of the engagement portion sheet 85.

Subsequently, as shown in FIG. 59, the first cutting is performed on only the area of the central adhesive portion 89 according to first cutting line 86 of the waveform which simultaneously traverses the portion of the engagement portion sheet 85.

At the same time or subsequently, the second cutting is performed according to the second cutting line 87 in the width direction which links the peak of the waveform of the first cutting line 86 to the side edge of the tape substrate 80 which is the nearest to the peak.

After performing the first cutting process according to the first cutting line 86 and the second cutting process according to the second cutting line 87, the individualized left side fastening tapes 1360A, 1360A - - - and the right side fastening tapes 1360A, 1360A - - - are obtained.

Thus, as shown in FIG. 59, for the fastening tapes 1360A obtained from the left side, the left end adhesive portion 88L used as the base side adhesive portion (1360*a* and 1360*b*) in the thirteenth embodiment is mounted on the left side portion on the back side of the semi-finished product, the central adhesive portion 89 can be used as the intermediate adhesive portion 1360*c* in the thirteenth embodiment, and the exposed portion 89R on the right side can be used as the top side adhesive portion 1360*d* in the thirteenth embodiment. On the other hand, for the fastening tape 1360A obtained from the right side, the right end adhesive portion 88R used as the base side adhesive portion (1360*a* and 1360*b*) in the thirteenth embodiment are mounted on the right side on the back of the semi-finished product, the central adhesive portion 89 can be used as the intermediate adhesive portion 1360*c* in the thirteenth embodiment, and the exposed portion 89L on the left side can be used as the top side adhesive portion 1360*d* in the thirteenth embodiment.

As is clear from the foregoing, in accordance with the disposable diaper of the present invention, a mark portion can be formed on the external surface of the belly side at a region where the engagement portion should be fastened, even though no adhered tape is used. In addition, a form where an external appearance does not deteriorate can be obtained although a distortion processed portion is formed in a large area. As a result, engagement and fixation can be performed at free positions, with no attention paid to the engagement position of the fastening tape. In addition, if an external surface is formed by a non-woven fabric, this invention has advantages that a cottony state can be prevented and the like although the engagement and fixation of the fastening tape are repeated.

INDUSTRIAL APPLICABILITY

As described above, an absorbent body according to the present invention is provided with a sufficient absorbing performance and flexibility although thinning is promoted. The absorbent body fits the motion of a human body, is excellent in wearability and is suitable for a disposable diaper, a sanitary napkin, an incontinence pad, a medical pad and the like. Particularly, this is the absorbent body mostly suitable for a disposable diaper.

What is claimed is:

1. A method for manufacturing an absorbent body of a body fluid absorbing article, the absorbent body comprising an air laid absorbent fiber having a dispersed and thin layer of a mixed absorbent fiber and super absorbent polymer, the method comprising the steps of:

(i) conveying an the absorbent fiber and a super absorbent polymer in an air flow into multiple dispersing chutes;
(ii) ejecting at the same time the absorbent fiber and the super absorbent polymer from multiple dispersing chutes onto an endless air-permeable conveyor belt;
(iii) applying an air sucking action on the absorbent fiber and the super absorbent polymer, while the absorbent fiber and the super absorbent polymer are disentangled and mixed to accumulate the absorbent fiber and the super absorbent fiber to form a web on said conveyor belt, said conveyor belt having a plurality of recess portions on the periphery thereof such that the air sucking action and accumulation are performed so as to allow only the inside of said recess portions to be of an air permeable structure;
(iv) transferring the web from said conveyor belt to opposing heating and pressing rolls;
(v) thinning the web by application of the opposing heating and pressing rolls against the web to produce an air laid absorbent body sheet; and
(vi) winding the air laid absorbent body sheet on a winding roll.

2. The method for manufacturing the absorbent body as claimed in claim 1, further comprising, before step (i), providing the super absorbent polymer in an amount of 40 to 80 wt % of a total weight of the super absorbent polymer and the absorbent fiber, wherein the super absorbent polymer comprises particles such that not more than 20% of the total number of said particles have a particle diameter of not more than 250 µm; and the absorbent body has a thickness of not more than 2 mm, a basis weight of not less than 300 gsm and not more than 550 gsm, and a density of not less than 150 kg/m$^3$ and not more than 417 kg/m$^3$.

3. The method for manufacturing the absorbent body as claimed in claim 1, further comprising, before step (i), providing the absorbent body with a plurality of holes, wherein the number of the holes is not less than 0.1 holes per 1 cm$^2$, and the holes have an area of not less than 0.03 mm$^2$.

* * * * *

UNITED STATES PATENT AND TRADEMARK OFFICE
CERTIFICATE OF CORRECTION

| | | |
|---|---|---|
| PATENT NO. | : 8,557,068 B2 | Page 1 of 1 |
| APPLICATION NO. | : 12/803996 | |
| DATED | : October 15, 2013 | |
| INVENTOR(S) | : Yosuke Mori et al. | |

It is certified that error appears in the above-identified patent and that said Letters Patent is hereby corrected as shown below:

On the Title page;

Item (62) Related U.S. Application Data:

delete "Jul. 12, 2001" and insert --Dec. 7, 2001--.

Signed and Sealed this
Twenty-fourth Day of June, 2014

Michelle K. Lee
*Deputy Director of the United States Patent and Trademark Office*